(12) United States Patent
Baur et al.

(10) Patent No.: US 11,655,267 B2
(45) Date of Patent: May 23, 2023

(54) OLIGOSACCHARIDE PREPARATIONS AND COMPOSITIONS

(71) Applicant: DSM IP Assets B.V., Heerlen (NL)

(72) Inventors: Manuela Baur, Möhlin (CH); Estel Canet-Martinez, Basel (CH); Ruediger Hainz, Binzen (DE); Ulrich Hoeller, Basel (CH); Lisa Ann Laprade, Dedham, MA (US); John Michael Geremia, Watertown, MD (US); Ghislain Schyns, Waltham, MA (US)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 17/292,119

(22) PCT Filed: Nov. 8, 2019

(86) PCT No.: PCT/US2019/060463
§ 371 (c)(1),
(2) Date: May 7, 2021

(87) PCT Pub. No.: WO2020/097458
PCT Pub. Date: May 14, 2020

(65) Prior Publication Data
US 2021/0395284 A1     Dec. 23, 2021

Related U.S. Application Data

(60) Provisional application No. 62/757,233, filed on Nov. 8, 2018, provisional application No. 62/757,486, filed on Nov. 8, 2018.

(51) Int. Cl.
*C07H 1/00*     (2006.01)
*C07H 3/06*     (2006.01)

(52) U.S. Cl.
CPC .................. *C07H 1/00* (2013.01); *C07H 3/06* (2013.01)

(58) Field of Classification Search
CPC ............ C07H 1/00; C07H 3/06; C08B 37/006
See application file for complete search history.

(56) References Cited

U.S. PATENT DOCUMENTS

| | | |
|---|---|---|
| 2016/0007642 A1 | 1/2016 | Geremia et al. |
| 2018/0000146 A1 | 1/2018 | Geremia |

FOREIGN PATENT DOCUMENTS

| | | | |
|---|---|---|---|
| JP | 2012158526 A | 1/2011 | |
| JP | 2012-158526 | 8/2012 | |
| WO | WO-2016122885 A1 * | 8/2016 | ............. A23L 33/10 |

OTHER PUBLICATIONS

International Search Report issued in International Application No. PCT/US2019/060463, dated Jan. 22, 2020 (4 pages).
Written Opinion of the International Searching Authority issued in International Application No. PCT/US2019/060463, dated Jan. 22, 2020 (6 pages).
EP Search Report and Supplementary European Search Report, EP Application 19 882 805.5 dated Jun. 30, 2022.

* cited by examiner

*Primary Examiner* — Jonathan S Lau
(74) *Attorney, Agent, or Firm* — Nixon & Vanderhye P.C.

(57) ABSTRACT

The present disclosure relates oligosaccharide preparations suitable for use in nutritional compositions such as animal feed and methods of manufacturing the described oligosaccharide preparations. The present disclosure further relates to nutritional compositions that comprise the oligosaccharide preparations. The disclosed oligosaccharide preparations can be advantageous as an animal feed due to, at least in part, their prebiotic utility and the presence of anhydrosubunit containing oligosaccharides, which can be used to detect and/or determine the presence and content of the disclosed oligosaccharide preparations in the nutritional composition.

9 Claims, 27 Drawing Sheets

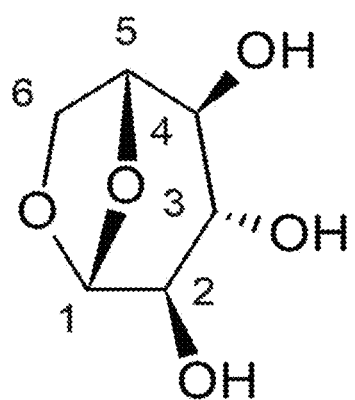
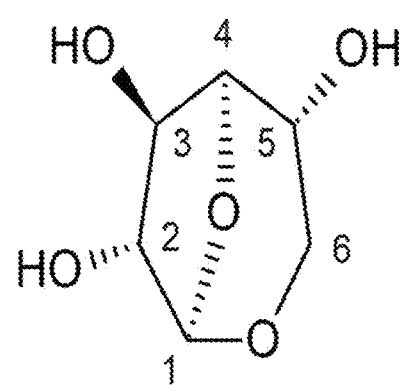
1,6-Anhydro-beta-D-glucofuranose
1,6-Anhydro-beta-D-glucopyranose
FIG. 5

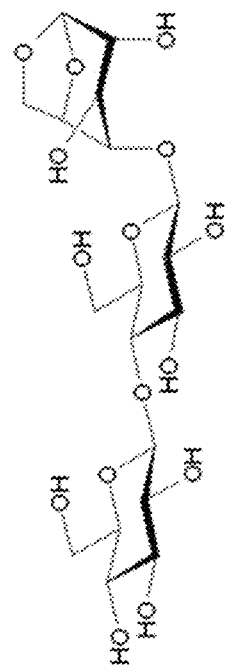
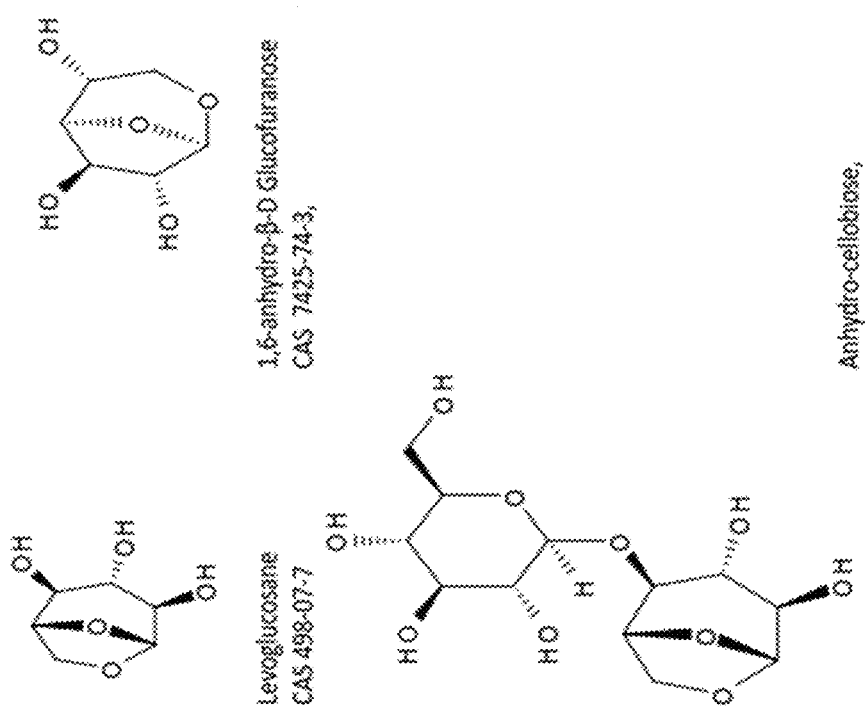
FIG. 12
FIG. 13

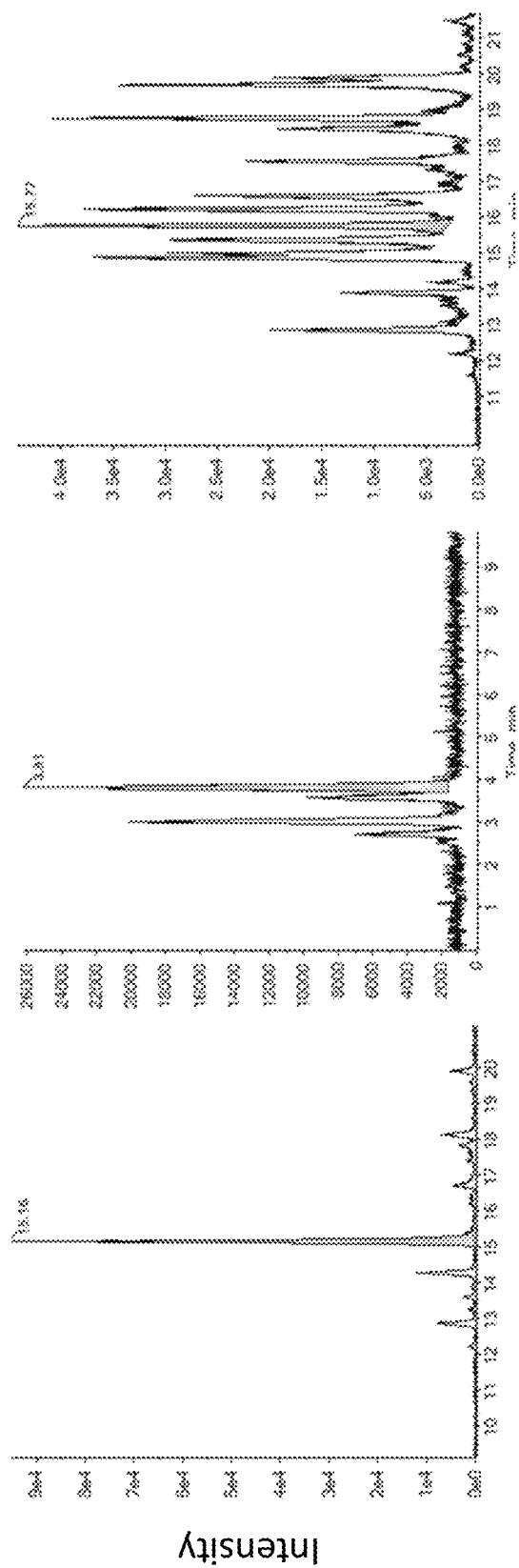
FIG. 15A Anhydro DP2
FIG. 15B Anhydro DP1
FIG. 15C DP2

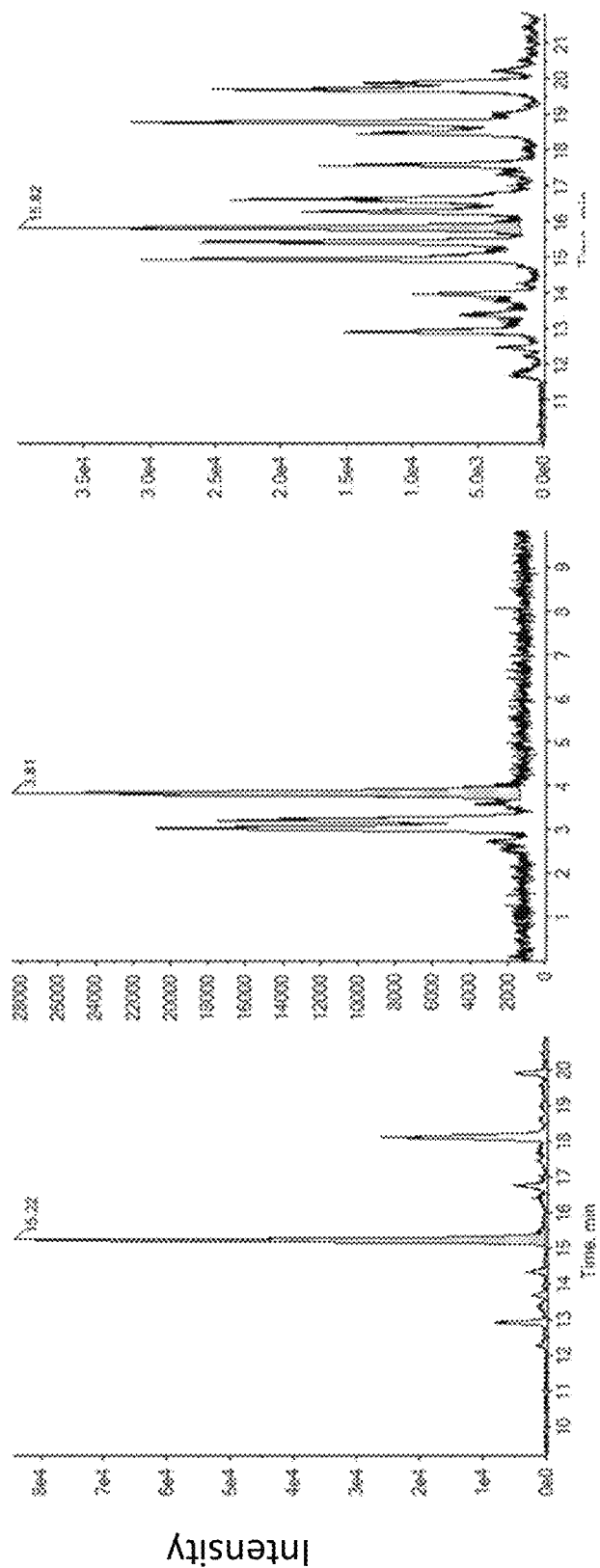
FIG. 16A Anhydro DP2
FIG. 16B Anhydro DP1
FIG. 16C DP2

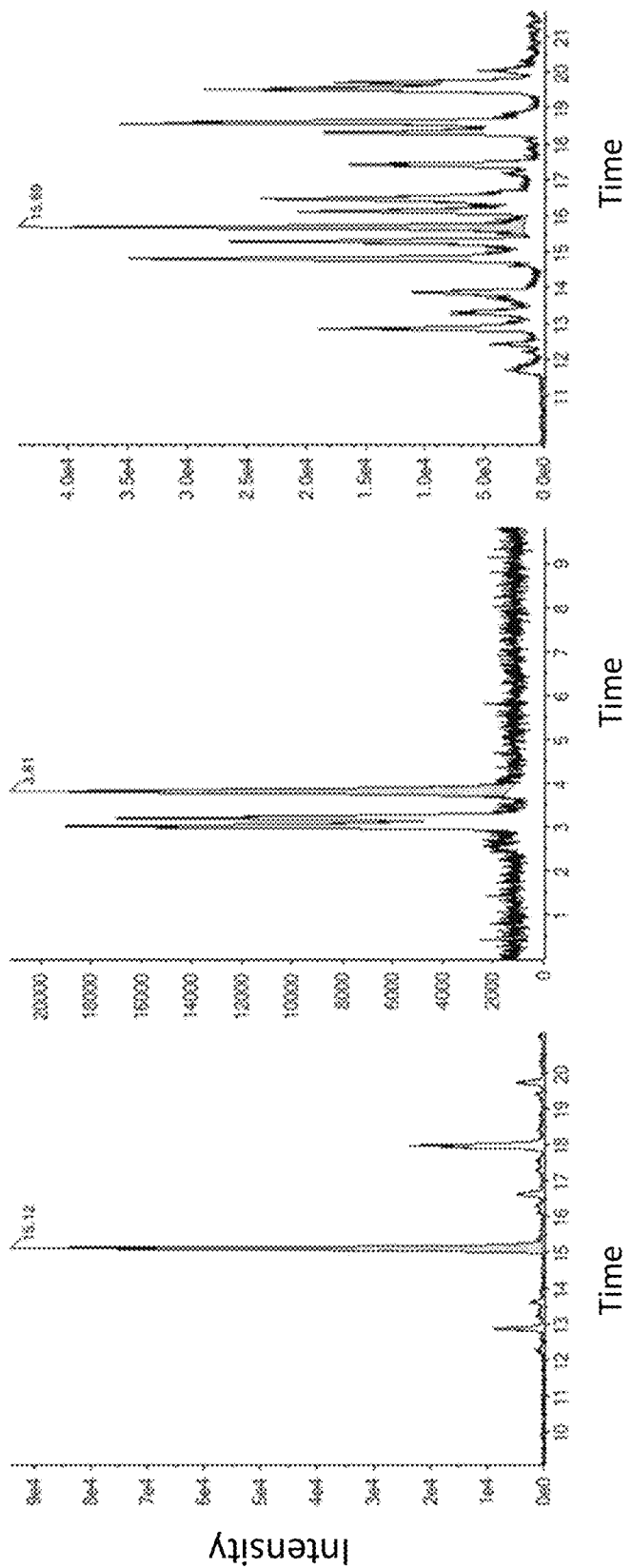
FIG. 17A Anhydro DP2
FIG. 17B Anhydro DP1
FIG. 17C DP2

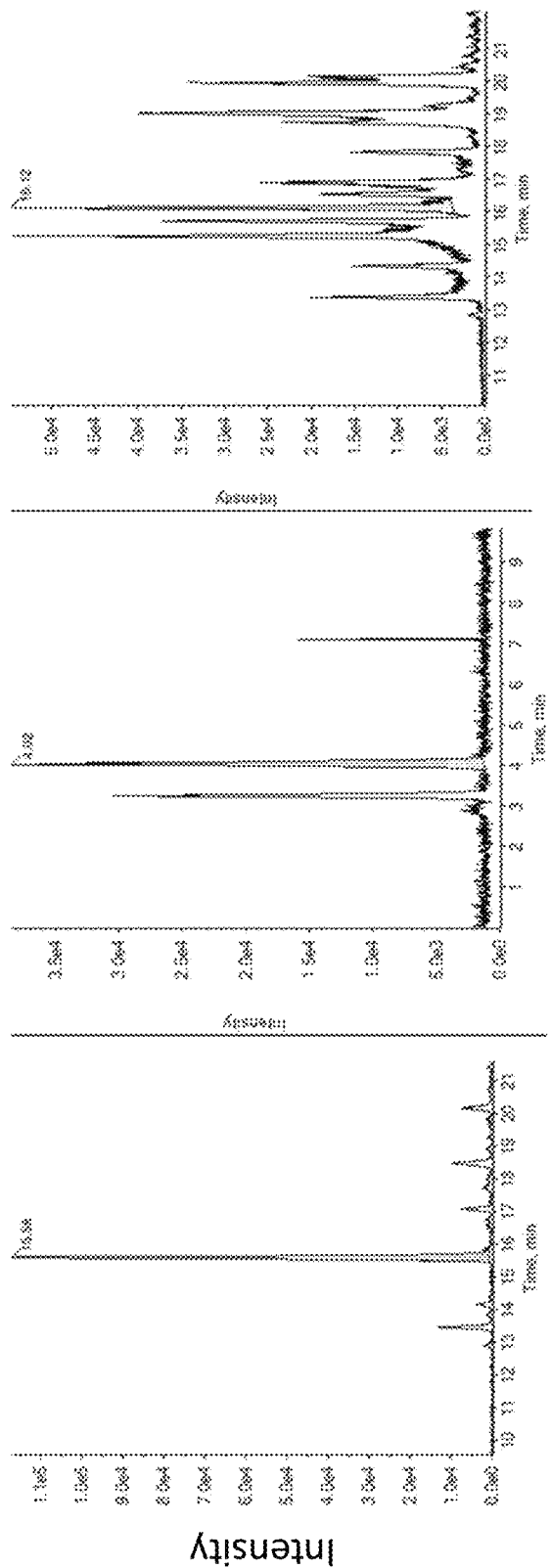

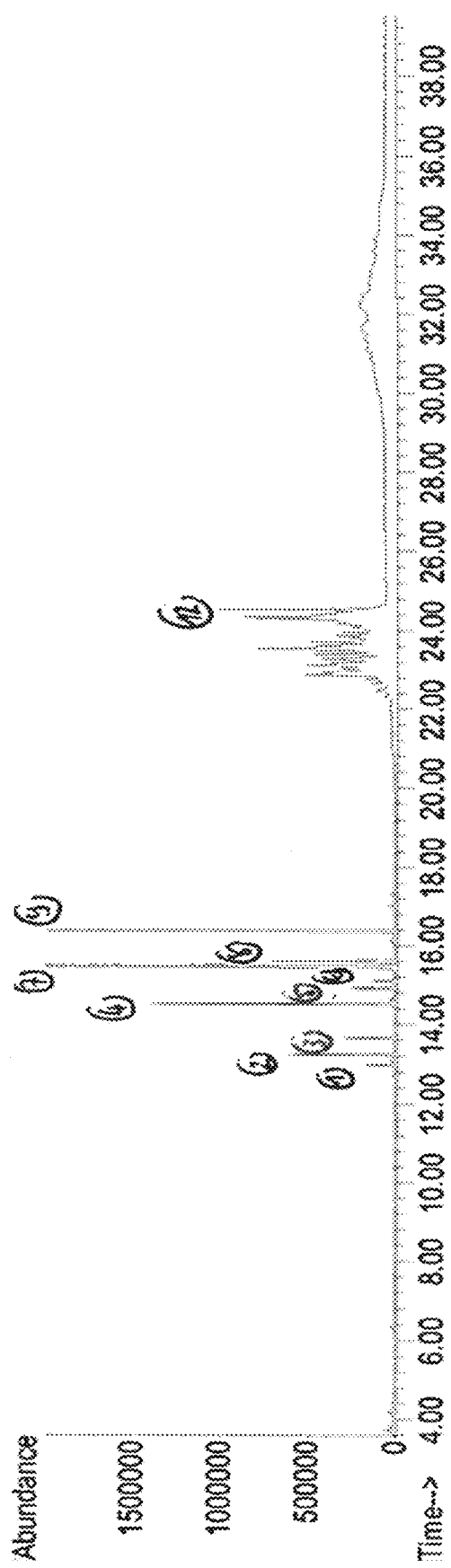
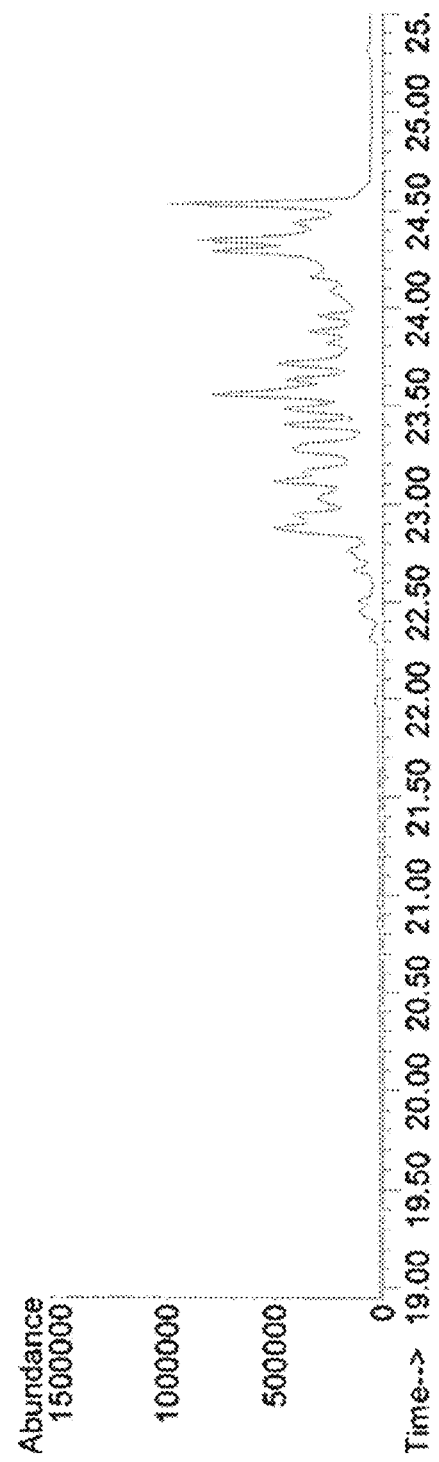
FIG. 20A
FIG. 20B

OLIGOSACCHARIDE PREPARATIONS AND COMPOSITIONS

CROSS-REFERENCE TO RELATED APPLICATIONS

This application is a National Stage of International Application No. PCT/US2019/060463, filed Nov. 8, 2019, which claims the benefit of U.S. Provisional Patent Application No. 62/757,233 and U.S. Provisional Patent Application No. 62/757,486, both filed on Nov. 8, 2018, the contents of which are hereby incorporated by reference in their entirety.

BACKGROUND

Oligosaccharides are a heterogeneous group of carbohydrates with various degrees of polymerizations. Oligosaccharides compositions may be produced naturally, e.g., in milk, or synthesized through enzymatic or chemical processes. Depending on the process of manufacture, the resultant oligosaccharide compositions may possess distinct chemical and/or physical properties. Enzymatic hydrolysis of longer chain oligosaccharides and polysaccharides may produce oligosaccharides through specific cleavages under mild reaction conditions. However, the use of enzymes in industrial process is limited by their thermostability, and enzymatic methods may generate degradation side products that cause metabolic problems when consumed by poultry, swine, and other livestock. On the other hand, chemical hydrolysis of longer chain oligosaccharides and polysaccharides may require harsh reaction conditions, and it is difficult to control the chemical and/or physical properties of oligosaccharides produced via the chemical hydrolysis process. Accordingly, there remains a need for manufacturing oligosaccharide compositions with desired properties.

Oligosaccharide preparations, which may generally include monosaccharides, oligosaccharides, polysaccharides, functionalized oligosaccharides, or their combinations, are used as additives in nutritional compositions such as animal feed. The addition of oligosaccharide preparations may improve the health and performance of the animal. However, it is challenging to detect or quantify an oligosaccharide preparation additive in a nutritional composition, because nutritional compositions usually contain other carbohydrate sources that may have structural similarities with the oligosaccharide preparations. As a result, a need exists for methods of selectively detecting or quantifying the oligosaccharide preparations in a nutritional composition.

SUMMARY

Provided herein are synthetic oligosaccharide preparations that comprise anhydro-subunit containing oligosaccharides. The disclosed oligosaccharide preparations can be advantageous as an additive in a nutritional composition for animal feed due to, e.g., their prebiotic utility and the presence of anhydro-subunit containing oligosaccharides, which can be used to detect and/or determine the presence and content of the disclosed oligosaccharide preparations in the animal nutritional composition. Accordingly, provided herein are animal nutritional compositions comprising the described oligosaccharide preparations, the presence and content of which in the nutritional composition can be detected or determined by e.g., the anhydro-subunit containing oligosaccharides such as anhydro-subunit containing monosaccharides and/or anhydro-subunit containing disaccharides. Further disclosed herein is a method of manufacturing an oligosaccharide preparation comprising anhydro-subunit containing oligosaccharides. In some embodiments, the method of manufacturing comprises controlling the water content, reaction time, and reaction temperature during the sugar polymerization and/or condensation reaction.

In one aspect, disclosed herein is a synthetic oligosaccharide preparation comprising at least n fractions of oligosaccharides each having a distinct degree of polymerization selected from 1 to n (DP1 to DPn fractions), wherein n is an integer greater than 3; wherein the DP1 and DP2 fractions each independently comprises from about 0.5% to about 15% of anhydro-subunit containing oligosaccharides by relative abundance as measured by mass spectrometry. In one aspect, disclosed herein is a synthetic oligosaccharide preparation comprising at least n fractions of oligosaccharides each having a distinct degree of polymerization selected from 1 to n (DP1 to DPn fractions), wherein n is an integer greater than 3; wherein the DP1 and DP2 fractions each independently comprises from about 0.1% to about 15% of anhydro-subunit containing oligosaccharides by relative abundance as measured by mass spectrometry. In some embodiments, the relative abundance of oligosaccharides in at least 5, 10, 20, or 30 DP fractions decreases monotonically with its degree of polymerization. In some embodiments, the relative abundance of oligosaccharides in each of the n fractions decreases monotonically with its degree of polymerization. In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, the DP2 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, the DP2 fraction comprises from about 5% to about 10% of anhydro-subunit containing oligosaccharides by relative abundance. In some embodiments, the DP2 fraction comprises from about 1% to about 10% of anhydro-subunit containing oligosaccharides by relative abundance. In some embodiments, the DP2 fraction comprises from about 0.1% to about 15% of anhydro-subunit containing oligosaccharides by relative abundance. In some embodiments, the DP2 fraction comprises from about 2% to about 12% of anhydro-subunit containing oligosaccharides by relative abundance. In some embodiments, the DP1 fraction comprises less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, the DP1 fraction comprises from about 2% to about 12% of anhydro-subunit containing oligosaccharides by relative abundance. In some embodiments, the DP1 fraction comprises from about 1% to about 10% of anhydro-subunit containing oligosaccharides by relative abundance. In some embodiments, the DP1 fraction comprises from about 0.1% to about 15% of anhydro-subunit containing oligosaccharides by relative abundance. In some embodiments, the DP1 fraction comprises from about 5% to about 10% of anhydro-subunit containing oligosaccharides by relative abundance. In some embodiments, the DP3 fraction comprises less than 15%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, the DP3 fraction comprises from about 2% to about 12% of anhydro-subunit containing oligosaccharides by relative abundance. In some embodiments, the DP3 fraction comprises from about 1% to about 10% of anhydro-subunit containing oligosaccharides by relative abundance. In some embodiments, the DP3 fraction comprises from about 0.1% to about 15% of anhydro-subunit containing oligosaccharides by relative abundance. In some embodiments, the DP3 fraction comprises from about 5% to about 10% of anhydro-subunit containing oligosaccharides by relative abundance. In some embodiments, the oligosaccharide preparation comprises less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, the oligosaccharide preparation comprises from about 1% to about 10% anhydro-subunit containing oligosaccharides by relative abundance. In some embodiments, the oligosaccharide preparation comprises from about 0.1% or 0.5% to about 10% or 15% anhydro-subunit containing oligosaccharides by relative abundance. In some embodiments, the oligosaccharide preparation comprises from about 2% to about 12% anhydro-subunit containing oligosaccharides by relative abundance. In some embodiments, the oligosaccharide preparation comprises from about 5% to about 10% anhydro-subunit containing oligosaccharides by relative abundance. In some embodiments, each fraction of the at least n fractions of oligosaccharides comprises less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% anhydro-subunit containing oligosaccharides by relative abundance. In some embodiments, the DP2 fraction comprises greater than 0.1%, greater than 0.5%, greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance. In some embodiments, the DP1 fraction comprises greater than 0.1%, greater than 0.5%, greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance. In some embodiments, the DP3 fraction comprises greater than 0.1%, greater than 0.5%, greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance. In some embodiments, the oligosaccharide preparation comprises greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance. In some embodiments, each fraction of the at least n fractions of oligosaccharides comprises greater than 0.1%, greater than 0.5%, greater than 0.6%, greater than 0.8%, greater than 1.0%, greater than 1.5%, greater than 2%, greater than 3%, greater than 4%, greater than 5%, greater than 6%, greater than 7%, greater than 8%, greater than 9%, greater than 10%, greater than 11%, or greater than 12% anhydro-subunit containing oligosaccharides by relative abundance. In some embodiments, more than 90% of the anhydro-subunit containing oligosaccharides have only one anhydro-subunit. In some embodiments, the oligosaccharide preparation has a DP1 fraction content of from about 1% to about 40% by weight as determined by liquid chromatography. In some embodiments, the oligosaccharide preparation has a DP2 fraction content of from about 1% to about 35% by weight as determined by liquid chromatography. In some embodiments, the oligosaccharide preparation has a DP3 fraction content of from about 1% to about 30% by weight as determined by liquid chromatography. In some embodiments, the oligosaccharide preparation has a DP4 fraction content of from about 0.1% to about 20% by weight as determined by liquid chromatography. In some embodiments, the oligosaccharide preparation has a DP5 fraction content of from about 0.1% to about 15% by weight as determined by liquid chromatography. In some embodiments, a ratio of the DP2 fraction to the DP1 fraction is from about 0.02 to about 0.40 by weight as determined by liquid chromatography. In some embodiments, a ratio of the DP3 fraction to the DP2 fraction is from about 0.01 to about 0.30 by weight as determined by liquid chromatography. In some embodiments, an aggregate content of the DP1 and the DP2 fractions in the oligosaccharide preparation is less than 50%, less than 40%, or less than 30% by weight as determined by liquid chromatography. In some embodiments, the oligosaccharide preparation comprises at least $10^3$, at least $10^4$, at least $10^5$, at least $10^6$ or at least $10^9$ different oligosaccharide species. In some embodiments, two or more independent oligosaccharides comprise different anhydro-subunits. In some embodiments, each of the anhydro-subunit containing oligosaccharides comprises one or more anhydro-subunits that are products of thermal dehydration of monosaccharides. In some embodiments, the oligosaccharide preparation comprises one or more anhydro-subunits selected from anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, and anhydro-xylose. In some embodiments, the oligosaccharide preparation comprises one or more anhydro-glucose, anhydro-galactose, anhydro-mannose, or anhydro-fructose subunits. In some embodiments, the DP1 fraction comprises 1,6-anhydro-β-D-glucofuranose or 1,6-anhydro-β-D-glucopyranose anhydro-subunits. In some embodiments, the DP1 fraction comprises both 1,6-anhydro-β-D-glucofuranose and 1,6-anhydro-β-D-glucopyranose anhydro-subunits. In some embodiments, a ratio of the 1,6-anhydro-β-D-glucofuranose to the 1,6-anhydro-β-D-glucopyranose is from about 10:1 to 1:10, from about 9:1 to about 1:10, from about 8:1 to about 1:10, from about 7:1 to about 1:10, from about 6:1 to about 1:10, from about 5:1 to about 1:10, from about 4:1 to about 1:10, from about 3:1 to about 1:10, from about 2:1 to about 1:10, from about 10:1 to about 1:9, from about 10:1 to about 1:8, from about 10:1 to about 1:7, from about 10:1 to about 1:6, from about 10:1 to about 1:5, from about 10:1 to about 1:4, from about 10:1 to about 1:3, from about 10:1 to about 1:2, or from about 1:1 to about 3:1 in the oligosaccharide reparation. In some embodiments, a ratio of the 1,6-anhydro-β-D-glucofuranose to the 1,6-anhydro-β-D-glucopyranose is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 in the oligosaccharide preparation. In some embodiments, a ratio of the 1,6-anhydro-β-D-glucofuranose to the 1,6-anhydro-β-D-glucopyranose is about 2:1 in the oligosaccharide preparation. In some embodiments, the DP2 fraction comprises at least 5 species of anhydro-subunit containing oligosaccharides. In some embodiments, the DP2 fraction comprises about 5 to 10 species of anhydro-subunit containing oligosaccharides. In some embodiments, the DP2 fraction comprises about 2 to 20 species of anhydro-subunit containing oligosaccharides. In some embodiments, the DP2 fraction does not comprise cellobiosan at a detectable level as determined by HPLC-MS. In some embodiments, the oligosaccharide preparation comprises one or more sugar caramelization products. In some embodiments, the sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf). In some embodiments, greater than 50%, 60%, 70%, 80%, 90%, 95%, or 99% of the anhydro-subunit containing oligosaccharides comprise a chain-end anhydro-subunit. In some embodiments, the oligosaccharide preparation has a weight average molecular weight of from about 300 to about 5000 g/mol, from about 500 to about 5000 g/mol, from about 700 to about 5000 g/mol, from about 500 to about 2000 g/mol, from about 700 to about 2000 g/mol, from about 700 to about 1500 g/mol, from about 300 to about 1500 g/mol, from about 300 to about 2000 g/mol, from about 400 to about 1300 g/mol, from about 400 to about 1200 g/mol, from about 400 to about 1100 g/mol, from about 500 to about 1300 g/mol, from about 500 to about 1200 g/mol, from about 500 to about 1100 g/mol, from about 600 to about 1300 g/mol, from about 600 to about 1200 g/mol, or from about 600 to about 1100 g/mol, as determined by high-performance liquid chromatography (HPLC). In some embodiments, the oligosaccharide preparation has a weight average molecular weight of from about 300 to about 2500 g/mol as determined by HPLC. In some embodiments, the oligosaccharide preparation has a weight average molecular weight of from about 500 to about 2000 g/mol as determined by HPLC. In some embodiments, the oligosaccharide preparation has a weight average molecular weight of from about 500 to about 1500 g/mol as determined by HPLC. In some embodiments, the oligosaccharide preparation has a number average molecular weight of from about 300 to about 5000 g/mol, from about 500 to about 5000 g/mol, from about 700 to about 5000 g/mol, from about 500 to about 2000 g/mol, from about 700 to about 2000 g/mol, from about 700 to about 1500 g/mol, from about 300 to about 1500 g/mol, from about 300 to about 2000 g/mol, from about 400 to about 1000 g/mol, from about 400 to about 900 g/mol, from about 400 to about 800 g/mol, from about 500 to about 900 g/mol, or from about 500 to about 800 g/mol, as determined by HPLC. In some embodiments, the oligosaccharide preparation has a number average molecular weight of from about 300 to about 2500 g/mol as determined by HPLC. In some embodiments, the oligosaccharide preparation has a number average molecular weight of from about 500 to about 2000 g/mol as determined by HPLC. In some embodiments, the oligosaccharide preparation has a number average molecular weight of from about 500 to about 1500 g/mol as determined by HPLC. In some embodiments, the oligosaccharide preparation has a weight average molecular weight of from about 2000 to about 2800 g/mol, from about 2100 to about 2700 g/mol, from about 2200 to about 2600 g/mol, from about 2300 to about 2500 g/mol, or from about 2320 to about 2420 g/mol. In some embodiments, the oligosaccharide preparation has a number average molecular weight of from about 1000 to about 2000 g/mol, from about 1100 to about 1900 g/mol, from about 1200 to about 1800 g/mol, from about 1300 to about 1700 g/mol, from about 1400 to about 1600 g/mol, or from about 1450 to about 1550 g/mol. In some embodiments, the oligosaccharide preparation comprises a monosaccharide subunit selected from: arabinose, lyxose, ribose, xylose, allose, altrose, mannose, gulose, idose, galactose, talose, psicose, fructose, sorbose, and tagatose. In some embodiments, the oligosaccharide preparation comprises a monosaccharide subunit selected from: xylose, mannose, galactose, and fructose In one aspect, provided herein is a nutritional composition comprising a herein disclosed oligosaccharide preparation. In some embodiments, the nutritional composition comprises a base nutritional composition. In some embodiments, the nutritional composition is an animal feed composition.

In one aspect, provided herein is a method comprising administering a nutritional composition comprising a base nutritional composition and a herein disclosed oligosaccharide preparation to an animal.

Provided herein is a synthetic oligosaccharide preparation comprising at least n fractions of oligosaccharides each having a distinct degree of polymerization selected from 1 to n (DP1 to DPn fractions), wherein n is an integer greater than 2; and wherein each fraction comprises from 1% to 90% anhydro-subunit containing oligosaccharides by relative abundance as measured by mass spectrometry. Provided herein is a synthetic oligosaccharide preparation comprising at least n fractions of oligosaccharides each having a distinct degree of polymerization selected from 1 to n (DP1 to DPn fractions), wherein n is an integer greater than 3; and wherein each fraction comprises from 0.1% to 15% anhydro-subunit containing oligosaccharides by relative abundance as measured by mass spectrometry. In some embodiments, the relative abundance of oligosaccharides in at least 5, 10, 20, or 30 DP fractions decreases monotonically with its degree of polymerization. In some embodiments, the relative abundance of oligosaccharides in each of the n fractions decreases monotonically with its degree of polymerization. In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, at least one fraction comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, the oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, each fraction comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, at least one fraction comprises less than 10%, 9%, 8%, 7%, 6%, 5%, 4%, 3%, or 2% anhydro-subunit containing oligosaccharides by relative abundance. In some embodiments, the oligosaccharide preparation comprises less than 10%, 9%, 8%, 7%, 6%, 5%, 4%, 3%, or 2% anhydro-subunit containing oligosaccharides by relative abundance. In some embodiments, each fraction comprises less than 10%, 9%, 8%, 7%, 6%, 5%, 4%, 3%, or 2% anhydro-subunit containing oligosaccharides by relative abundance. In some embodiments, at least one fraction comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, the oligosaccharide preparation comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, each fraction comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, more than 99%, 95%, 90%, 85%, 80%, 75%, 70%, 65%, 60%, 55%, 50%, 45%, 40%, 35%, or 30% of the anhydro-subunit containing oligosaccharides have only one anhydro-subunit. In some embodiments, the oligosaccharide preparation has a DP1 fraction content from 1 to 40% by relative abundance. In some embodiments, the oligosaccharide preparation has a DP2 fraction content from 1 to 35% by relative abundance. In some embodiments, the oligosaccharide preparation has a DP3 fraction content from 1 to 30% by relative abundance. In some embodiments, the oligosaccharide preparation has a DP4 fraction content from 0.1 to 20% by relative abundance. In some embodiments, the oligosaccharide preparation has a DP5 fraction content from 0.1 to 15% by relative abundance. In some embodiments, the ratio of DP2 fraction to DP1 fraction is 0.02-0.40 by relative abundance. In some embodiments, the ratio of DP3 fraction to DP2 fraction is 0.01-0.30 by relative abundance. In some embodiments, the aggregate content of DP1 and DP2 fractions in the oligosaccharide preparation is less than 50, 30, or 10% by relative abundance. In some embodiments, the oligosaccharide preparation comprises at least $10^3$, $10^4$, $10^5$, $10^6$ or $10^9$ different oligosaccharide species. In some embodiments, two or more independent oligosaccharides comprise different anhydro-subunits. In some embodiments, the oligosaccharide preparation comprises one or more anhydro-subunits that are products of thermal dehydration of monosaccharides. In some embodiments, the oligosaccharide preparation comprises one or more anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, or anhydro-xylose subunits. In some embodiments, the oligosaccharide preparation comprises one or more anhydro-glucose, anhydro-galactose, anhydro-mannose, or anhydro-fructose subunits. In some embodiments, the oligosaccharide preparation comprises one or more 1,6-anhydro-β-D-glucofuranose or 1,6-anhydro-β-D-glucopyranose subunits. In some embodiments, the oligosaccharide preparation comprises both 1,6-anhydro-β-D-glucofuranose and 1,6-anhydro-β-D-glucopyranose anhydro-subunits. In some embodiments, a ratio of 1,6-anhydro-β-D-glucofuranose to 1,6-anhydro-β-D-glucopyranose is from about 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in the oligosaccharide reparation. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 within the oligosaccharide preparation. In some embodiments, the ratio of 1,6-anhydro-β-D-glucofuranose to 1,6-anhydro-β-D-glucopyranose is about 2:1 in the oligosaccharide preparation. In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in each fraction. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in each fraction. In some embodiments, the ratio of 1,6-anhydro-β-D-glucofuranose to 1,6-anhydro-β-D-glucopyranose is about 2:1 in each fraction. In some embodiments, at least 1%, 5%, 10%, 20%, 30%, 40%, 50%, 60%, 70%, 80%, or 90% of anhydro-subunits are selected from a group consisting of 1,6-anhydro-β-D-glucofuranose and 1,6-anhydro-β-D-glucopyranose. In some embodiments, the oligosaccharide preparation comprises one or more anhydro-subunits that are sugar caramelization products. In some embodiments, the sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf). In some embodiments, from about 0.1% to 5%, 0.1% to 2%, or 0.1% to 1% of the anhydro-subunits in the preparation are caramelization products. In some embodiments, greater than 30%, 40%, 50%, 60%, 70%, 80%, 90%, 95%, or 99% of the anhydro-subunit containing oligosaccharides comprise a chain-end anhydro-subunit. In some embodiments, the weight average molecular weight of the preparation is about from 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1300 g/mol, 400 to 1200 g/mol, 400 to 1100 g/mol, 500 to 1300 g/mol, 500 to 1200 g/mol, 500 to 1100 g/mol, 600 to 1300 g/mol, 600 to 1200 g/mol, or 600 to 1100 g/mol. In some embodiments, the number average molecular weight of the preparation is about from 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1000 g/mol, 400 to 900 g/mol, 400 to 800 g/mol, 500 to 900 g/mol, or 500 to 800 g/mol. In some embodiments, the weight average molecular weight of the preparation is about from 2000 to 2800 g/mol, 2100 to 2700 g/mol, 2200 to 2600 g/mol, 2300 to 2500 g/mol, or 2320 to 2420 g/mol. In some embodiments, the number average molecular weight of the preparation is about from 1000 to 2000 g/mol, 1100 to 1900 g/mol, 1200 to 1800 g/mol, 1300 to 1700 g/mol, 1400 to 1600 g/mol, or 1450 to 1550 g/mol.

Provided herein is a nutritional composition comprising a herein described oligosaccharide preparation. In some embodiments, the nutritional composition further comprises a base nutritional composition. Further provided herein is a method comprising administering a nutritional composition comprising a base nutritional composition and the herein described oligosaccharide preparation to an animal. Provided herein is a method of manufacturing an oligosaccharide preparation comprising heating an aqueous composition comprising one or more feed sugars and a catalyst to a temperature and for a time sufficient to induce polymerization, wherein the catalyst is selected from the group consisting of: Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Palmitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; and Tryptophan, and wherein the oligosaccharide preparation comprises at least n fractions of oligosaccharides each having a distinct degree of polymerization selected from 1 (DP1 fraction) to n (DPn fraction), wherein n is an integer greater than or equal to 2. In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, the method comprises heating the aqueous composition for a time sufficient for the aqueous composition to reach equilibrium. In some embodiments, the method comprises heating the aqueous composition for a time sufficient for the aqueous composition to reach equilibrium, as determined by a relative standard deviation of a series of Km of less than 15%, 10%, or 5%, and wherein $$Km = \frac{[DP_m][H_2O]}{[DP_{m-1}][DP1]},$$

m is an integer larger than 1 and less than or equal to n, a series of Km comprises at least 5 Km numbers, [H$_2$O] represents the molar water concentration, and [DP1], [DP$_{m-1}$], and [DP$_m$] represent the molar concentrations of oligosaccharides in the DP1, DP$_{m-1}$, and DP$_m$ fractions respectively. In some embodiments, the method comprises heating the aqueous composition for a time sufficient for the aqueous composition to reach equilibrium, as determined by a change of the weight average molecular weight of the aqueous composition of less than 15% over the period of 1 hour.

Provided herein is a method of manufacturing an oligosaccharide preparation comprising heating an aqueous composition comprising one or more feed sugars and a catalyst to a temperature and for a time sufficient to induce polymerization and for the aqueous composition to reach equilibrium, wherein the oligosaccharide preparation comprises at least n fractions of oligosaccharides each having a distinct degree of polymerization selected from 1 (DP1 fraction) to n (DPn fraction), wherein n is an integer greater than or equal to 2. In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, the method comprises heating the aqueous composition for a time sufficient for the aqueous composition to reach equilibrium, as determined by a change of the weight average molecular weight of the aqueous composition of less than 15% over the period of 1 hour. In some embodiments, the catalyst is selected from the group consisting of: Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan. In some embodiments, the method comprises heating an aqueous composition comprising one or more feed sugars at a quantity of larger than 1 kg. In some embodiments, the one or more feed sugars comprise monosaccharides, disaccharides, trisaccharides, tetrasaccharides, or a combination thereof, and wherein the said monosaccharides, disaccharides, trisaccharides, or tetrasaccharides is each independently in their hydrate or de-hydrate form. In some embodiments, the one or more feed sugars comprise glucose, galactose, fructose, mannose, or any combination thereof, and wherein each of the glucose, galactose, fructose, or mannose is independently in its mono-hydrate or de-hydrate form. In some embodiments, the one or more feed sugars comprise functionalized or modified sugars. In some embodiments, the functionalized or modified sugars comprise amino sugars, sugar acids, sugar alcohols, sugar amides, sugar ethers, or any combination thereof. In some embodiments, the functionalized or modified sugars comprise glucosamine, N-acetylglucosamine, glucuronic acid, galacturonic acid, glucitol, xylitol, mannitol, sorbitol, or any combination thereof. In some embodiments, the one of more feed sugars comprise deoxysugars. In some embodiments, the deoxysugars comprise fucose, rhamnose, deoxyribose, fuculose, or any combination thereof. In some embodiments, the catalyst is present in an amount from about 0.01% to 5%, 0.02% to 4%, 0.03% to 3%, or 0.05% to 2% of the one or more feed sugars by dry weight. In some embodiments, the catalyst is present in an amount from about 1% to 2% of the one or more feed sugars by dry weight. In some embodiments, the catalyst is added into the aqueous composition in a dry or wet form. In some embodiments, the method comprises adding water to form the aqueous composition. In some embodiments, the aqueous composition comprises about from 2% to 10%, 2% to 8%, or 4% to 8% water by total weight. In some embodiments, the aqueous composition comprises about 4% to 8% water by total weight. In some embodiments, the method comprises heating the aqueous composition to a temperature from about 100° C. to 200° C., 100° C. to 180° C., 110° C. to 170° C., 120° C. to 160° C., 130° C. to 150° C., or 135° C. to 145° C. In some embodiments, the method comprises heating the aqueous composition to a temperature from about 135° C. to 145° C. In some embodiments, the method comprises maintaining the water content from about 1% to 20%, 2% to 10%, 2% to 8%, or 4% to 8% by weight while the aqueous composition is heated to the temperature and for the time sufficient to induce polymerization. In some embodiments, the method comprises maintaining the water content by distillation under atmosphere pressure. In some embodiments, the method comprises heating the aqueous composition for a time sufficient for the aqueous composition to reach a number average molecular weight of about from 500 to 2000 g/mol. In some embodiments, the method comprises heating the aqueous composition for a time sufficient for the aqueous composition to reach a weight average molecular weight of about from 700 to 3000 g/mol. In some embodiments, the polymerization is achieved by polycondensation. In some embodiments, the method further comprises removing water such that the aqueous composition comprises about 9% water by total weight. In some embodiments, the method further comprises dilution, decolorization, filtration, or any combination thereof. In some embodiments, each of the n fractions of the oligosaccharide preparation comprises from 1% to 90% anhydro-subunit containing oligosaccharides by relative abundance. In some embodiments, the relative abundance of oligosaccharides in at least 5, 10, 20, or 30 DP fractions decreases monotonically with its degree of polymerization. In some embodiments, the relative abundance of oligosaccharides in each of the n fractions decreases monotonically with its degree of polymerization. In some embodiments, the nutritional composition is an animal feed composition.

Provided herein is a synthetic oligosaccharide preparation manufactured by a method comprising, heating an aqueous composition comprising one or more feed sugars and a catalyst to a temperature and for a time sufficient to induce polymerization, wherein the catalyst is selected from the group consisting of: Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan, wherein the oligosaccharide preparation comprises at least n fractions of oligosaccharides each having a distinct degree of polymerization selected from 1 (DP1 fraction) to n (DPn fraction), wherein n is an integer greater than or equal to 2, and wherein each fraction comprises from about 0.1% to 90% anhydro-subunit containing oligosaccharides by relative abundance as measured by mass spectrometry.

Provided herein is a synthetic oligosaccharide preparation manufactured by a method comprising, heating an aqueous composition comprising one or more feed sugars and a catalyst to a temperature and for a time sufficient to induce polymerization and for the aqueous composition to reach equilibrium, wherein the oligosaccharide preparation comprises at least n fractions of oligosaccharides each having a distinct degree of polymerization selected from 1 (DP1 fraction) to n (DPn fraction), wherein n is an integer greater than or equal to 2, and wherein each fraction comprises from about 0.1% to 90% anhydro-subunit containing oligosaccharides by relative abundance as measured by mass spectrometry. In some embodiments, each fraction comprises from about 0.1% to 15% anhydro-subunit containing oligosaccharides by relative abundance. In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50.

Provided herein is a method of manufacturing a synthetic oligosaccharide composition, the method comprising: (a) heating an aqueous composition that comprises at least one feed sugar and a catalyst to a pre-determined temperature for a period of time sufficient to induce polymerization of said at least one feed sugar; to thereby produce a batch of a synthetic oligosaccharide preparation; wherein said batch comprises at least 1 kg of said synthetic oligosaccharide preparation; and wherein said synthetic oligosaccharide preparation comprises at least n fractions of oligosaccharides each having a distinct degree of polymerization selected from 1 (DP1 fraction) to n (DPn fraction), wherein n is an integer greater than or equal to 3; and wherein each fraction of said synthetic oligosaccharide preparation comprises from about 0.5% to about 15% anhydro-subunit containing oligosaccharides by relative abundance as measured by mass spectrometry; (b) measuring a level of said catalyst in said produced batch of said synthetic oligosaccharide preparation; (c) comparing said level to a pre-determined acceptance criterion; and (d) formulating at least a portion of said batch of said synthetic oligosaccharide preparation only if the level of said catalyst in said batch preparation meets said pre-determined acceptance criterion. Provided herein is a method of manufacturing a synthetic oligosaccharide composition, the method comprising: (a) heating an aqueous composition that comprises at least one feed sugar and a catalyst to a pre-determined temperature for a period of time sufficient to induce polymerization of said at least one feed sugar; to thereby produce a batch of a synthetic oligosaccharide preparation; wherein said batch comprises at least 1 kg of said synthetic oligosaccharide preparation; and wherein said synthetic oligosaccharide preparation comprises at least n fractions of oligosaccharides each having a distinct degree of polymerization selected from 1 (DP1 fraction) to n (DPn fraction), wherein n is an integer greater than or equal to 3; and wherein each fraction of said synthetic oligosaccharide preparation comprises from 0.5% to 15% anhydro-subunit containing oligosaccharides by relative abundance as measured by mass spectrometry; (b) measuring a level of said catalyst in said produced batch of said synthetic oligosaccharide preparation; and (c) formulating at least a portion of said batch of said synthetic oligosaccharide preparation only if the level of said catalyst in said batch preparation is equal to or less than 0.1 wt % of said batch; to thereby produce a synthetic oligosaccharide composition. In some embodiments, said formulating comprises adjusting the pH of said synthetic oligosaccharide preparation, producing a powder form of said synthetic oligosaccharide preparation, producing a solid form of said synthetic oligosaccharide preparation, packaging said synthetic oligosaccharide preparation, labeling said synthetic oligosaccharide preparation, releasing said synthetic oligosaccharide preparation into commerce, or offering for sale or selling said synthetic oligosaccharide preparation. In some embodiments, said formulating comprises producing a powder form of said synthetic oligosaccharide preparation. In some embodiments, said powder form is a glass powder formulation. In some embodiments, said powder form is a carrier-loaded powder formulation. In some embodiments, said formulating comprises producing a solid form of said synthetic oligosaccharide preparation. In some embodiments, said formulating comprises extrusion of said synthetic oligosaccharide preparation to thereby produce an extruded solid form of said synthetic oligosaccharide preparation. In some embodiments, said catalyst is selected from the group consisting of: (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid, 3-(1-pyridinio)-1-propanesulfonate; 2-(2-pyridinyl)ethanesulfonic acid; 3-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; poly(styrene sulfonic acid-co-divinylbenzene); lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; and Tryptophan. In some embodiments, said catalyst is selected from the group consisting of: Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; and Tryptophan.

In some embodiments, said heating comprises heating said aqueous composition for a time sufficient for said aqueous composition to reach equilibrium, wherein equilibrium is determined by a relative standard deviation of a series of Km of less than 15%, 10%, or 5%, and wherein, m is an integer larger than 1 and less than or equal to n, a series of Km comprises at least 5 Km numbers, [H2O] represents the molar water concentration, and [DP1], [DPm−1], and [DPm] represent the molar concentrations of oligosaccharides in the DP1, DPm−1, and DPm fractions respectively. In some embodiments, said heating comprises heating said aqueous composition for at least 30 minutes, 1 hour, 2 hours, 3 hours, 4 hours, 5 hours, 6 hours, 7 hour, 8 hours, 9 hours, or 10 hours. In some embodiments, said heating comprises heating said aqueous composition for at least 6 hours. In some embodiments, said heating comprises heating said aqueous composition for at least 10 hours. In some embodiments, said heating comprises heating said aqueous composition from 1 to 24 hours, 1 to 16 hours, 1 to 8 hours, 1 to 4 hours, 1 to 3 hours, 1 to 2 hours, 2 to 12 hours, 2 to 10 hours, 2 to 8 hours, 2 to 6 hours, 2 to 4 hours, 3 to 8 hours, 3 to 6 hours, 3 to 5 hours, 3 to 4 hours, 4 to 24 hours, 4 to 16 hours, 4 to 12 hours, 4 to 10 hours, 4 to 8 hours, 4 to 6 hours, 5 to 24 hours, 5 to 16 hours, 5 to 12 hours, 5 to 10 hours, 5 to 8 hours, 5 to 6 hours, 6 to 24 hours, 6 to 16 hours, 6 to 12 hours, 6 to 10 hours, or 6 to 8 hours. In some embodiments, said heating comprises heating said aqueous composition from 5-12 hours. In some embodiments, the method comprises measuring the viscosity, water content, number average molecular weight (MWn), weight average molecular weight (MWw), anhydro-subunit content, the distribution of degree of polymerization, evolved condensate water, reaction water content, total dissolved solids content, residual monomer content, pH, density, or color of said aqueous composition during said heating. In some embodiments, said measurement is used to determine said period of time sufficient to induce polymerization. In some embodiments, said anhydro subunit content is in a DP1 fraction or a DP2 fraction. In some embodiments, said anhydro subunit content is determined by LC-MS-MS. In some embodiments, said number average molecular weight (MWn) is determined by HPLC/GPC chromatography. In some embodiments, said weight average molecular weight (MWw) is determined by HPLC/GPC chromatography. In some embodiments, said total dissolved solids content is determined by Karl Fisher titration. In some embodiments, said viscosity is determined using a viscometer or rheometer. In some embodiments, said water content is determined using an evaporation method, a distillation method, or by a chemical reaction method. In some embodiments, said chemical reaction method is Karl Fischer titration. In some embodiments, said water content is determined using a moisture analyzer, IR spectroscopy, or NIR spectroscopy. In some embodiments, said batch comprises at least 10 kg, 100 kg, 1000 kg, 5,000 kg, 10,000 kg, 20,000 kg, 30,000 kg, 40,000 kg, 50,000 kg of said synthetic oligosaccharide preparation. In some embodiments, said batch comprises at least 5,000 kg of said synthetic oligosaccharide preparation. In some embodiments, said pre-determined acceptance criterion is a predetermined wt % of said catalyst in said batch. In some embodiments, said wt % is less than 1 wt %, 0.9 wt %, 0.8 wt %, 0.7 wt %, 0.6 wt %, 0.5 wt %, 0.4 wt %, 0.3 wt %, 0.2 wt %, or 0.1 wt %. In some embodiments, said pre-determined acceptance criterion is a commercial release specification. In some embodiments, said feed sugar comprises functionalized or modified sugars. In some embodiments, said functionalized or modified sugars comprise amino sugars, sugar acids, sugar amides, or sugar ethers, or any combination thereof. In some embodiments, said functionalized or modified sugars comprise glucosamine, N-acetylglucosamine, glucuronic acid, or galacturonic acid, or any combination thereof. In some embodiments, said feed sugar comprises deoxysugars. In some embodiments, the deoxysugars comprise fucose, rhamnose, deoxyribose, or fuculose, or any combination thereof. In some embodiments, said feed sugar comprises glucose, xylose, galactose, mannose, malto-dextrin, arabinose, lactose, sucrose, or trehalose, or any combination thereof. In some embodiments, said heating comprises heating said aqueous composition that comprises at least two, three, four, or five feed sugars and a catalyst to a pre-determined temperature for a period of time sufficient to induce polymerization of said at least one feed sugar. In some embodiments, said heating comprises heating said aqueous composition that comprises at least two feed sugars. In some embodiments, each of said at least two feed sugars comprise glucose, xylose, galactose, mannose, malto-dextrin, arabinose, lactose, sucrose, or trehalose, or any combination thereof. In some embodiments, each of said at least two, three, four, or five feed sugars comprise glucose, xylose, galactose, mannose, malto-dextrin, arabinose, lactose, sucrose, or trehalose, or any combination thereof. In some embodiments, the method comprises maintaining a water content by distillation under atmosphere pressure. In some embodiments, the method comprises maintaining a water content by adding water. In some embodiments, the method comprises maintaining a water content within a range of from about 2%, 3%, 4% or 5% to about 6%, 7%, 8%, or 9% as measured by an average water content before and after reaction. In some embodiments, the method comprises maintaining a water content within a range of from about 2% to about 8% as measured by an average water content before and after reaction. In some embodiments, the relative abundance of oligosaccharides in at least 5, 10, 20, or 30 DP fractions of said oligosaccharide preparation decreases monotonically with its degree of polymerization. In some embodiments, the relative abundance of oligosaccharides in each of the n fractions of said oligosaccharide preparation decreases monotonically with its degree of polymerization. In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, at least one fraction of said oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, at least one fraction of said oligosaccharide preparation comprises from about 80%-0.5%, 80%-1%, 80%-2%, 80%-3%, 80%-4%, 80%-5%, 80%-10%, 80%-20%, 80%-30%, 80%-40%, 80%-50%, 60%-1%, 60%-2%, 60%-3%, 60%-4%, 60%-5%, 60%-10%, 60%-20%, 60%-30%, 60%-40%, 60%-50%, 40%-1%, 40%-2%, 40%-3%, 40%-4%, 40%-5%, 40%-10%, 40%-20%, 40%-30%, 40%-50%, 30%-1%, 30%-2%, 30%-3%, 30%-4%, 30%-5%, 30%-10%, 30%-20%, 20%-1%, 20%-2%, 20%-3%, 20%-4%, 20%-5%, 20%-10%, 10%-1%, 10%-2%, 10%-3%, 10%-4%, 10%-5%, 5%-1%, 5%-2%, 5%-3%, or 5%-4% anhydro-subunit containing oligosaccharides by relative abundance. In some embodiments, said oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, said oligosaccharide preparation comprises from about 80%-0.5%, 80%-1%, 80%-2%, 80%-3%, 80%-4%, 80%-5%, 80%-10%, 80%-20%, 80%-30%, 80%-40%, 80%-50%, 60%-1%, 60%-2%, 60%-3%, 60%-4%, 60%-5%, 60%-10%, 60%-20%, 60%-30%, 60%-40%, 60%-50%, 40%-1%, 40%-2%, 40%-3%, 40%-4%, 40%-5%, 40%-10%, 40%-20%, 40%-30%, 40%-50%, 30%-1%, 30%-2%, 30%-3%, 30%-4%, 30%-5%, 30%-10%, 30%-20%, 20%-1%, 20%-2%, 20%-3%, 20%-4%, 20%-5%, 20%-10%, 10%-1%, 10%-2%, 10%-3%, 10%-4%, 10%-5%, 5%-1%, 5%-2%, 5%-3%, or 5%-4% anhydro-subunit containing oligosaccharides by relative abundance. In some embodiments, each fraction of said oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, each fraction of said oligosaccharide preparation comprises from about 80%-1%, 80%-2%, 80%-3%, 80%-4%, 80%-5%, 80%-10%, 80%-20%, 80%-30%, 80%-40%, 80%-50%, 60%-1%, 60%-2%, 60%-3%, 60%-4%, 60%-5%, 60%-10%, 60%-20%, 60%-30%, 60%-40%, 60%-50%, 40%-1%, 40%-2%, 40%-3%, 40%-4%, 40%-5%, 40%-10%, 40%-20%, 40%-30%, 40%-50%, 30%-1%, 30%-2%, 30%-3%, 30%-4%, 30%-5%, 30%-10%, 30%-20%, 20%-1%, 20%-2%, 20%-3%, 20%-4%, 20%-5%, 20%-10%, 10%-1%, 10%-2%, 10%-3%, 10%-4%, 10%-5%, 5%-1%, 5%-2%, 5%-3%, or 5%-4% anhydro-subunit containing oligosaccharides by relative abundance. In some embodiments, at least one fraction of said oligosaccharide preparation comprises less than 10%, 9%, 8%, 7%, 6%, 5%, 4%, 3%, or 2% anhydro-subunit containing oligosaccharides by relative abundance. In some embodiments, at least one fraction of said oligosaccharide preparation comprises from about 80%-1%, 80%-2%, 80%-3%, 80%-4%, 80%-5%, 80%-10%, 80%-20%, 80%-30%, 80%-40%, 80%-50%, 60%-1%, 60%-2%, 60%-3%, 60%-4%, 60%-5%, 60%-10%, 60%-20%, 60%-30%, 60%-40%, 60%-50%, 40%-1%, 40%-2%, 40%-3%, 40%-4%, 40%-5%, 40%-10%, 40%-20%, 40%-30%, 40%-50%, 30%-1%, 30%-2%, 30%-3%, 30%-4%, 30%-5%, 30%-10%, 30%-20%, 20%-1%, 20%-2%, 20%-3%, 20%-4%, 20%-5%, 20%-10%, 10%-1%, 10%-2%, 10%-3%, 10%-4%, 10%-5%, 5%-1%, 5%-2%, 5%-3%, or 5%-4% anhydro-subunit containing oligosaccharides by relative abundance. In some embodiments, said oligosaccharide preparation comprises less than 10%, 9%, 8%, 7%, 6%, 5%, 4%, 3%, or 2% anhydro-subunit containing oligosaccharides by relative abundance. In some embodiments, said oligosaccharide preparation comprises from about 80%-0.5%, 80%-1%, 80%-2%, 80%-3%, 80%-4%, 80%-5%, 80%-10%, 80%-20%, 80%-30%, 80%-40%, 80%-50%, 60%-1%, 60%-2%, 60%-3%, 60%-4%, 60%-5%, 60%-10%, 60%-20%, 60%-30%, 60%-40%, 60%-50%, 40%-1%, 40%-2%, 40%-3%, 40%-4%, 40%-5%, 40%-10%, 40%-20%, 40%-30%, 40%-50%, 30%-1%, 30%-2%, 30%-3%, 30%-4%, 30%-5%, 30%-10%, 30%-20%, 20%-1%, 20%-2%, 20%-3%, 20%-4%, 20%-5%, 20%-10%, 10%-1%, 10%-2%, 10%-3%, 10%-4%, 10%-5%, 5%-1%, 5%-2%, 5%-3%, or 5%-4% anhydro-subunit containing oligosaccharides by relative abundance as measured by MALDI-MS, LC-MS/MS or GC-MS. In some embodiments, each fraction of said oligosaccharide preparation comprises less than 10%, 9%, 8%, 7%, 6%, 5%, 4%, 3%, or 2% anhydro-subunit containing oligosaccharides by relative abundance. In some embodiments, each fraction of said oligosaccharide preparation comprises from about 80%-0.5%, 80%-1%, 80%-2%, 80%-3%, 80%-4%, 80%-5%, 80%-10%, 80%-20%, 80%-30%, 80%-40%, 80%-50%, 60%-1%, 60%-2%, 60%-3%, 60%-4%, 60%-5%, 60%-10%, 60%-20%, 60%-30%, 60%-40%, 60%-50%, 40%-1%, 40%-2%, 40%-3%, 40%-4%, 40%-5%, 40%-10%, 40%-20%, 40%-30%, 40%-50%, 30%-1%, 30%-2%, 30%-3%, 30%-4%, 30%-5%, 30%-10%, 30%-20%, 20%-1%, 20%-2%, 20%-3%, 20%-4%, 20%-5%, 20%-10%, 10%-1%, 10%-2%, 10%-3%, 10%-4%, 10%-5%, 5%-1%, 5%-2%, 5%-3%, or 5%-4% anhydro-subunit containing oligosaccharides by relative abundance. In some embodiments, at least one fraction of said oligosaccharide comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, said oligosaccharide preparation comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, each fraction of said oligosaccharide preparation comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, at least one fraction of said oligosaccharide preparation comprises greater than 20%, 21%, 22%, 23%, 24%, or 25% anhydro-subunit containing oligosaccharides by relative abundance. In some embodiments, said oligosaccharide preparation comprises greater than 20%, 21%, 22%, 23%, 24%, or 25% anhydro-subunit containing oligosaccharides by relative abundance. In some embodiments, each fraction of said oligosaccharide preparation comprises greater than 20%, 21%, 22%, 23%, 24%, or 25% anhydro-subunit containing oligosaccharides by relative abundance. In some embodiments, more than 99%, 95%, 90%, 85%, 80%, 75%, 70%, 65%, 60%, 55%, 50%, 45%, 40%, 35%, or 30% of the anhydro-subunit containing oligosaccharides have only one anhydro-subunit. In some embodiments, from about 80%-1%, 80%-2%, 80%-3%, 80%-4%, 80%-5%, 80%-10%, 80%-20%, 80%-30%, 80%-40%, 80%-50%, 60%-1%, 60%-2%, 60%-3%, 60%-4%, 60%-5%, 60%-10%, 60%-20%, 60%-30%, 60%-40%, 60%-50%, 40%-1%, 40%-2%, 40%-3%, 40%-4%, 40%-5%, 40%-10%, 40%-20%, 40%-30%, 40%-50%, 30%-1%, 30%-2%, 30%-3%, 30%-4%, 30%-5%, 30%-10%, 30%-20%, 20%-1%, 20%-2%, 20%-3%, 20%-4%, 20%-5%, 20%-10%, 10%-1%, 10%-2%, 10%-3%, 10%-4%, 10%-5%, 5%-1%, 5%-2%, 5%-3%, or 5%-4% of the anhydro-subunit containing oligosaccharides have only one anhydro-subunit. In some embodiments, said oligosaccharide preparation has a DP1 fraction content from 1 to 40% by relative abundance. In some embodiments, said oligosaccharide preparation has a DP2 fraction content from 1 to 35% by relative abundance. In some embodiments, said oligosaccharide preparation has a DP3 fraction content from 1 to 30% by relative abundance. In some embodiments, said oligosaccharide preparation has a DP4 fraction content from 0.1 to 20% by relative abundance. In some embodiments, said oligosaccharide preparation comprises a DP5 fraction content from 0.1 to 15% by relative abundance. In some embodiments, said oligosaccharide preparation comprises a DP2 fraction and a DP1 fraction, wherein the ratio of said DP2 fraction to said DP1 fraction is 0.02-0.40 by relative abundance. In some embodiments, said oligosaccharide preparation comprises a DP3 fraction and a DP2 fraction, wherein the ratio of said DP3 fraction to said DP2 fraction in said oligosaccharide preparation is 0.01-0.30 by relative abundance. In some embodiments, said oligosaccharide preparation comprises a DP1 fraction and a DP2 fraction, wherein the aggregate content of said DP1 and said DP2 fractions in said oligosaccharide preparation is less than 50, 30, or 10% by relative abundance. In some embodiments, said oligosaccharide preparation comprises at least 1000, 5000, 10000, 20000, 30000, 40000, 50000, or 100000 different oligosaccharide species. In some embodiments, at least two independent oligosaccharides of said oligosaccharide preparation comprise different anhydro-subunits. In some embodiments, said oligosaccharide preparation comprises at least one oligosaccharide comprising an anhydro-subunit that is a product of thermal dehydration of a monosaccharide. In some embodiments, said oligosaccharide preparation comprises at least one oligosaccharide that comprises an anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, or anhydro-xylose subunit. In some embodiments, said oligosaccharide preparation comprises at least one anhydro-glucose, anhydro-galactose, anhydro-mannose, or anhydro-fructose subunit. In some embodiments, said oligosaccharide preparation comprises at least one 1,6-anhydro-β-D-glucofuranose or 1,6-anhydro-β-D-glucopyranose subunit. In some embodiments, said oligosaccharide preparation comprises at least one 1,6-anhydro-β-D-glucofuranose subunit and at least one 1,6-anhydro-β-D-glucopyranose anhydro-subunit. In some embodiments, a ratio of 1,6-anhydro-β-D-glucofuranose to 1,6-anhydro-β-D-glucopyranose in said oligosaccharide preparation is from about 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1. In some embodiments, a ratio of 1,6-anhydro-β-D-glucofuranose to 1,6-anhydro-β-D-glucopyranose in said oligosaccharide preparation is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10. In some embodiments, a ratio of 1,6-anhydro-β-D-glucofuranose to 1,6-anhydro-β-D-glucopyranose in said oligosaccharide preparation is about 2:1. In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in each fraction. In some embodiments, a ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in each fraction of said oligosaccharide preparation. In some embodiments, a ratio of 1,6-anhydro-β-D-glucofuranose to 1,6-anhydro-β-D-glucopyranose is about 2:1 in each fraction of said oligosaccharide preparation. In some embodiments, at least 1%, 5%, 10%, 20%, 30%, 40%, 50%, 60%, 70%, 80%, or 90% of said anhydro-subunits in said oligosaccharide preparation are selected from a group consisting of 1,6-anhydro-β-D-glucofuranose and 1,6-anhydro-β-D-glucopyranose. In some embodiments, said oligosaccharide preparation comprises at least one anhydro-subunit that is a sugar caramelization product. In some embodiments, said sugar caramelization product is selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf). In some embodiments, from about 0.1% to 5%, 0.1% to 2%, or 0.1% to 1% of said anhydro-subunits in said oligosaccharide preparation are caramelization products. In some embodiments, at least 30%, 40%, 50%, 60%, 70%, 80%, 90%, 95%, or 99% of the anhydro-subunit containing oligosaccharides in said oligosaccharide preparation comprise a chain-end anhydro-subunit. In some embodiments, from about 1%-100%, 1%-99%, 1%-90%, 1%-80%, 1%-70%, 1%-60%, 1%-50%, 1%-40%, 1%-30%, 1%-20%, 1%-10%, 1%-5%, 1%-4%, 1%-3%, 1%-2%, 10%-100%, 10%-99%, 10%-90%, 10%-80%, 10%-70%, 10%-60%, 10%-50%, 10%-40%, 10%-30%, 10%-20%, 20%-100%, 20%-99%, 20%-90%, 20%-80%, 20%-70%, 20%-60%, 20%-50%, 20%-40%, or 20%-30% of the anhydro-subunit containing oligosaccharides in said oligosaccharide preparation comprise a chain-end anhydro-subunit. In some embodiments, the weight average molecular weight of said oligosaccharide preparation is from about 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1300 g/mol, 400 to 1200 g/mol, 400 to 1100 g/mol, 500 to 1300 g/mol, 500 to 1200 g/mol, 500 to 1100 g/mol, 600 to 1300 g/mol, 600 to 1200 g/mol, or 600 to 1100 g/mol. In some embodiments, the number average molecular weight of said oligosaccharide preparation is from about 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1000 g/mol, 400 to 900 g/mol, 400 to 800 g/mol, 500 to 900 g/mol, or 500 to 800 g/mol. In some embodiments, the weight average molecular weight of said oligosaccharide preparation is from about 2000 to 2800 g/mol, 2100 to 2700 g/mol, 2200 to 2600 g/mol, 2300 to 2500 g/mol, or 2320 to 2420 g/mol. In some embodiments, the number average molecular weight of said oligosaccharide preparation is from about 1000 to 2000 g/mol, 1100 to 1900 g/mol, 1200 to 1800 g/mol, 1300 to 1700 g/mol, 1400 to 1600 g/mol, or 1450 to 1550 g/mol.

Provided herein is a synthetic oligosaccharide preparation comprising at least n fractions of oligosaccharides each having a distinct degree of polymerization selected from 1 to n (DP1 to DPn fractions), wherein n is an integer greater than 2; and wherein each fraction comprises from 1% to 90% anhydro-subunit containing oligosaccharides by relative abundance as measured by mass spectrometry. In some embodiments, the relative abundance of oligosaccharides in at least 5, 10, 20, or 30 DP fractions decreases monotonically with its degree of polymerization. In some embodiments, the relative abundance of oligosaccharides in each of the n fractions decreases monotonically with its degree of polymerization. In some embodiments, n is at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, at least one fraction comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, the oligosaccharide preparation comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, each fraction comprises less than 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, or 2% anhydro-subunit containing oligosaccharides by relative abundance. In some embodiments, at least one fraction comprises less than 10%, 9%, 8%, 7%, 6%, 5%, 4%, 3%, or 2% anhydro-subunit containing oligosaccharides by relative abundance. In some embodiments, the oligosaccharide preparation comprises less than 10%, 9%, 8%, 7%, 6%, 5%, 4%, 3%, or 2% anhydro-subunit containing oligosaccharides by relative abundance. In some embodiments, each fraction comprises less than 10%, 9%, 8%, 7%, 6%, 5%, 4%, 3%, or 2% anhydro-subunit containing oligosaccharides by relative abundance. In some embodiments, at least one fraction comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, the oligosaccharide preparation comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, each fraction comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% anhydro-subunit containing oligosaccharides by relative abundance. In some embodiments, at least one fraction comprises greater than 20%, 21%, 22%, 23%, 24%, or 25% anhydro-subunit containing oligosaccharides by relative abundance. In some embodiments, the oligosaccharide preparation comprises greater than 20%, 21%, 22%, 23%, 24%, or 25% anhydro-subunit containing oligosaccharides by relative abundance. In some embodiments, each fraction comprises greater than 20%, 21%, 22%, 23%, 24%, or 25% anhydro-subunit containing oligosaccharides by relative abundance. In some embodiments, more than 99%, 95%, 90%, 85%, 80%, 75%, 70%, 65%, 60%, 55%, 50%, 45%, 40%, 35%, or 30% of the anhydro-subunit containing oligosaccharides have only one anhydro-subunit. In some embodiments, the oligosaccharide preparation has a DP1 fraction content from 1 to 40% by relative abundance. In some embodiments, the oligosaccharide preparation has a DP2 fraction content from 1 to 35% by relative abundance. In some embodiments, the oligosaccharide preparation has a DP3 fraction content from 1 to 30% by relative abundance. In some embodiments, the oligosaccharide preparation has a DP4 fraction content from 0.1 to 20% by relative abundance. In some embodiments, the oligosaccharide preparation has a DP5 fraction content from 0.1 to 15% by relative abundance. In some embodiments, the ratio of DP2 fraction to DP1 fraction is 0.02-0.40 by relative abundance. In some embodiments, the ratio of DP3 fraction to DP2 fraction is 0.01-0.30 by relative abundance. In some embodiments, the aggregate content of DP1 and DP2 fractions in the oligosaccharide preparation is less than 50, 30, or 10% by relative abundance. In some embodiments, the oligosaccharide preparation comprises at least $10^3$, $10^4$, $10^5$, $10^6$ or $10^9$ different oligosaccharide species. In some embodiments, two or more independent oligosaccharides comprise different anhydro-subunits. In some embodiments, the oligosaccharide preparation comprises one or more anhydro-subunits that are products of reversible thermal dehydration of monosaccharides. In some embodiments, the oligosaccharide preparation comprises one or more anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, or anhydro-xylose subunits. In some embodiments, the oligosaccharide preparation comprises one or more anhydro-glucose, anhydro-galactose, anhydro-mannose, or anhydro-fructose subunits. In some embodiments, the oligosaccharide preparation comprises one or more 1,6-anhydro-β-D-glucofuranose or 1,6-anhydro-β-D-glucopyranose subunits. In some embodiments, the oligosaccharide preparation comprises both 1,6-anhydro-β-D-glucofuranose and 1,6-anhydro-β-D-glucopyranose anhydro-subunits. In some embodiments, a ratio of 1,6-anhydro-β-D-glucofuranose to 1,6-anhydro-β-D-glucopyranose is from about 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in the oligosaccharide reparation. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 within the oligosaccharide preparation. In some embodiments, the ratio of 1,6-anhydro-β-D-glucofuranose to 1,6-anhydro-β-D-glucopyranose is about 2:1 in the oligosaccharide preparation. In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in each fraction. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in each fraction. In some embodiments, the ratio of 1,6-anhydro-β-D-glucofuranose to 1,6-anhydro-β-D-glucopyranose is about 2:1 in each fraction. In some embodiments, at least 1%, 5%, 10%, 20%, 30%, 40%, 50%, 60%, 70%, 80%, or 90% of anhydro-subunits are selected from a group consisting of 1,6-anhydro-β-D-glucofuranose and 1,6-anhydro-β-D-glucopyranose. In some embodiments, the oligosaccharide preparation comprises one or more anhydro-subunits that are sugar caramelization products. In some embodiments, the sugar caramelization products are selected from a group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf). In some embodiments, the oligosaccharide preparation comprises 5-hmf subunits. In some embodiments, from about 0.1% to 5%, 0.1% to 2%, or 0.1% to 1% of the anhydro-subunits in the preparation are caramelization products. In some embodiments, greater than 30%, 40%, 50%, 60%, 70%, 80%, 90%, 95%, or 99% of the anhydro-subunit containing oligosaccharides comprise a chain-end anhydro-subunit. In some embodiments, the weight average molecular weight of the preparation is about from 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1300 g/mol, 400 to 1200 g/mol, 400 to 1100 g/mol, 500 to 1300 g/mol, 500 to 1200 g/mol, 500 to 1100 g/mol, 600 to 1300 g/mol, 600 to 1200 g/mol, or 600 to 1100 g/mol. In some embodiments, the number average molecular weight of the preparation is about from 300 to 5000 g/mol, 500 to 5000 g/mol, 700 to 5000 g/mol, 500 to 2000 g/mol, 700 to 2000 g/mol, 700 to 1500 g/mol, 300 to 1500 g/mol, 300 to 2000 g/mol, 400 to 1000 g/mol, 400 to 900 g/mol, 400 to 800 g/mol, 500 to 900 g/mol, or 500 to 800 g/mol. In some embodiments, the weight average molecular weight of the preparation is about from 2000 to 2800 g/mol, 2100 to 2700 g/mol, 2200 to 2600 g/mol, 2300 to 2500 g/mol, or 2320 to 2420 g/mol. In some embodiments, the number average molecular weight of the preparation is about from 1000 to 2000 g/mol, 1100 to 1900 g/mol, 1200 to 1800 g/mol, 1300 to 1700 g/mol, 1400 to 1600 g/mol, or 1450 to 1550 g/mol. Provided herein is a nutritional composition comprising a herein described oligosaccharide preparation. In some embodiments, the nutritional composition further comprises a base nutritional composition. Further provided herein is a method comprising administering a nutritional composition comprising a base nutritional composition and the herein described oligosaccharide preparation to an animal.

Provided herein is a method of manufacturing a synthetic oligosaccharide preparation comprising heating an aqueous composition comprising one or more feed sugars and a catalyst to a temperature and for a time sufficient to induce polymerization, wherein the catalyst is selected from the group consisting of: Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Palmitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; and Tryptophan, and wherein the oligosaccharide preparation comprises at least n fractions of oligosaccharides each having a distinct degree of polymerization selected from 1 (DP1 fraction) to n (DPn fraction), wherein n is an integer greater than or equal to 2. In some embodiments, the method comprises heating the aqueous composition for a time sufficient for the aqueous composition to reach equilibrium. In some embodiments, the method comprises heating the aqueous composition for a time sufficient for the aqueous composition to reach equilibrium, as determined by a relative standard deviation of a series of Km of less than 15%, 10%, or 5%, and wherein $$Km = \frac{[DP_m][H_2O]}{[DP_{m-1}][DP1]},$$

m is an integer larger than 1 and less than or equal to n, a series of Km comprises at least 5 Km numbers, $[H_2O]$ represents the molar water concentration, and [DP1], $[DP_{m-1}]$, and $[DP_m]$ represent the molar concentrations of oligosaccharides in the DP1, $DP_{m-1}$, and $DP_m$ fractions respectively. In some embodiments, the method comprises heating the aqueous composition for a time sufficient for the aqueous composition to reach equilibrium, as determined by a change of the weight average molecular weight of the aqueous composition of less than 15% over the period of 1 hour. Provided herein is a method of manufacturing an oligosaccharide preparation comprising heating an aqueous composition comprising one or more feed sugars and a catalyst to a temperature and for a time sufficient to induce polymerization and for the aqueous composition to reach equilibrium, wherein the oligosaccharide preparation comprises at least n fractions of oligosaccharides each having a distinct degree of polymerization selected from 1 (DP1 fraction) to n (DPn fraction), wherein n is an integer greater than or equal to 2. In some embodiments, the method comprises heating the aqueous composition for a time sufficient for the aqueous composition to reach equilibrium, as determined by a change of the weight average molecular weight of the aqueous composition of less than 15% over the period of 1 hour. In some embodiments, the catalyst is selected from the group consisting of: Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan. In some embodiments, the method comprises heating an aqueous composition comprising one or more feed sugars at a quantity of larger than 1 kg. In some embodiments, the one or more feed sugars comprise monosaccharides, disaccharides, trisaccharides, tetrasaccharides, or a combination thereof, and wherein the said monosaccharides, disaccharides, trisaccharides, or tetrasaccharides is each independently in their hydrate or de-hydrate form. In some embodiments, the one or more feed sugars comprise glucose, galactose, fructose, mannose, or any combination thereof, and wherein each of the glucose, galactose, fructose, or mannose is independently in its mono-hydrate or de-hydrate form. In some embodiments, the one or more feed sugars comprise functionalized or modified sugars. In some embodiments, the functionalized or modified sugars comprise amino sugars, sugar acids, sugar alcohols, sugar amides, sugar ethers, or any combination thereof. In some embodiments, the functionalized or modified sugars comprise amino sugars, sugar acids, sugar amides, sugar ethers, or any combination thereof. In some embodiments, the functionalized or modified sugars comprise glucosamine, N-acetylglucosamine, glucuronic acid, galacturonic acid, glucitol, xylitol, mannitol, sorbitol, or any combination thereof. In some embodiments, the functionalized or modified sugars comprise glucosamine, N-acetylglucosamine, glucuronic acid, galacturonic acid, or any combination thereof. In some embodiments, the one of more feed sugars comprise deoxysugars. In some embodiments, the deoxysugars comprise fucose, rhamnose, deoxyribose, fuculose, or any combination thereof. In some embodiments, the catalyst is present in an amount from about 0.01% to 5%, 0.02% to 4%, 0.03% to 3%, or 0.05% to 2% of the one or more feed sugars by dry weight. In some embodiments, the catalyst is present in an amount from about 1% to 2% of the one or more feed sugars by dry weight. In some embodiments, the catalyst is added into the aqueous composition in a dry or wet form. In some embodiments, the method comprises adding water to form the aqueous composition. In some embodiments, the aqueous composition comprises about from 2% to 10%, 2% to 8%, or 4% to 8% water by total weight. In some embodiments, the aqueous composition comprises about 4% to 8% water by total weight. In some embodiments, the method comprises heating the aqueous composition to a temperature from about 100° C. to 200° C., 100° C. to 180° C., 110° C. to 170° C., 120° C. to 160° C., 130° C. to 150° C., or 135° C. to 145° C. In some embodiments, the method comprises heating the aqueous composition to a temperature from about 135° C. to 145° C. In some embodiments, the method comprises maintaining the water content from about 1% to 20%, 2% to 10%, 2% to 8%, or 4% to 8% by weight while the aqueous composition is heated to the temperature and for the time sufficient to induce polymerization. In some embodiments, the method comprises maintaining the water content by distillation under atmosphere pressure. In some embodiments, the method comprises maintaining the water content by adding water. In some embodiments, the method comprises heating the aqueous composition for a time sufficient for the aqueous composition to reach a number average molecular weight of about from 500 to 2000 g/mol. In some embodiments, the method comprises heating the aqueous composition for a time sufficient for the aqueous composition to reach a weight average molecular weight of about from 700 to 3000 g/mol. In some embodiments, the polymerization is achieved by polycondensation. In some embodiments, the method further comprises removing water such that the aqueous composition comprises about 9% water by total weight. In some embodiments, the method further comprises dilution, decolorization, filtration, or any combination thereof. In some embodiments, each of the n fractions of the oligosaccharide preparation comprises from 1% to 90% anhydro-subunit containing oligosaccharides by relative abundance. In some embodiments, the relative abundance of oligosaccharides in at least 5, 10, 20, or 30 DP fractions decreases monotonically with its degree of polymerization. In some embodiments, the relative abundance of oligosaccharides in each of the n fractions decreases monotonically with its degree of polymerization. In some embodiments, the nutritional composition is an animal feed composition. Provided herein is a synthetic oligosaccharide preparation manufactured by a method comprising, heating an aqueous composition comprising one or more feed sugars and a catalyst to a temperature and for a time sufficient to induce polymerization, wherein the catalyst is selected from the group consisting of: Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino) ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan, wherein the oligosaccharide preparation comprises at least n fractions of oligosaccharides each having a distinct degree of polymerization selected from 1 (DP1 fraction) to n (DPn fraction), wherein n is an integer greater than or equal to 2, and wherein each fraction comprises from 1% to 90% anhydro-subunit containing oligosaccharides by relative abundance as measured by mass spectrometry. Provided herein is a synthetic oligosaccharide preparation manufactured by a method comprising, heating an aqueous composition comprising one or more feed sugars and a catalyst to a temperature and for a time sufficient to induce polymerization and for the aqueous composition to reach equilibrium, wherein the oligosaccharide preparation comprises at least n fractions of oligosaccharides each having a distinct degree of polymerization selected from 1 (DP1 fraction) to n (DPn fraction), wherein n is an integer greater than or equal to 2, and wherein each fraction comprises from 1% to 90% anhydro-subunit containing oligosaccharides by relative abundance as measured by mass spectrometry. Provided herein is a method of manufacturing a synthetic oligosaccharide preparation comprising heating an aqueous composition comprising one or more feed sugars and a catalyst to a temperature and for a time sufficient to induce polymerization and for the aqueous composition to reach equilibrium, wherein the oligosaccharide preparation comprises at least n fractions of oligosaccharides each having a distinct degree of polymerization selected from 1 (DP1 fraction) to n (DPn fraction), wherein n is an integer greater than or equal to 2, and wherein equilibrium is determined by a relative standard deviation of a series of Km of less than 15%, 10%, or 5%, and wherein $$Km = \frac{[DP_m][H_2O]}{[DP_{m-1}][DP1]},$$

m is an integer larger than 1 and less than or equal to n, a series of Km comprises at least 5 Km numbers, [H$_2$O] represents the molar water concentration, and [DP1], [DP$_{m-1}$], and [DPm] represent the molar concentrations of oligosaccharides in the DP1, DP$_{m-1}$, and DPm fractions respectively.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing (also "figure" and "FIG." herein), of which:

FIG. 5 illustrates the NMR assignments of 1,6-anhydro-beta-D-glucofuranose and 1,6-anhydro-beta-D-glucopyranose.

FIG. 12 illustrates two DP1 and one DP2 anhydro-subunit containing oligosaccharides.

FIG. 13 illustrates an anhydro-subunit containing oligosaccharide (cellotriosan).

FIG. 15A illustrates LC-MS/MS detection of the anhydro DP2 species of an oligosaccharide preparation of Example 1; FIG. 15B illustrates LC-MS/MS detection of the anhydro DP1 species of an oligosaccharide preparation of Example 1; FIG. 15C illustrates LC-MS/MS detection of the DP2 species of an oligosaccharide preparation of Example 1.

FIG. 16A illustrates LC-MS/MS detection of the anhydro DP2 species of an oligosaccharide preparation of Example 3; FIG. 16B illustrates LC-MS/MS detection of the anhydro DP1 species of an oligosaccharide preparation of Example 3; FIG. 16C illustrates LC-MS/MS detection of the DP2 species of an oligosaccharide preparation of Example 3.

FIG. 17A illustrates LC-MS/MS detection of the anhydro DP2 species of an oligosaccharide preparation of Example 4; FIG. 17B illustrates LC-MS/MS detection of the anhydro DP1 species of an oligosaccharide preparation of Example 4; FIG. 17C illustrates LC-MS/MS detection of the DP2 species of an oligosaccharide preparation of Example 4.

FIG. 18A illustrates LC-MS/MS detection of the anhydro DP2 species of an oligosaccharide preparation of Example 7; FIG. 18B illustrates LC-MS/MS detection of the anhydro DP1 species of an oligosaccharide preparation of Example 7; FIG. 18C illustrates LC-MS/MS detection of the DP2 species of an oligosaccharide preparation of Example 7.

FIG. 20A illustrates GC-MS spectrum detection of the DP1, anhydro DP1, DP2 and anhydro DP2 fractions of an oligosaccharide preparation of Example 3; FIG. 20B illustrates an enlargement of the DP2 and anhydro DP 2 fractions as shown in FIG. 20A.

DETAILED DESCRIPTION

Figure 1:
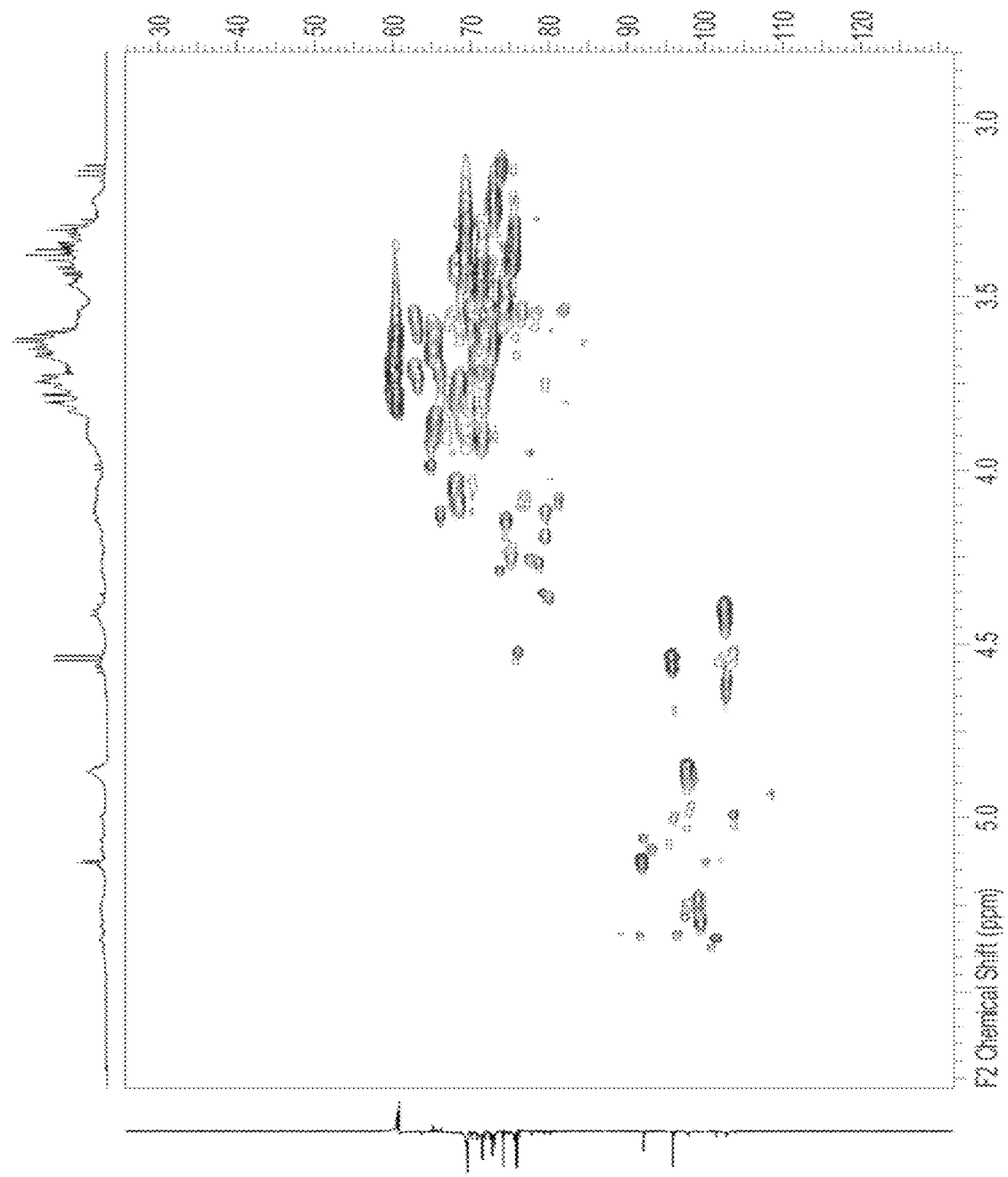
FIG. 1 illustrates part of a 2D $^1$H, $^{13}$C-HSQC NMR spectrum of the oligosaccharide preparation of Example 7.

Described herein are oligosaccharide preparations and animal nutritional compositions that comprise such oligosaccharide preparations. The described oligosaccharide preparations are advantageous in terms of prebiotic utility, quality control and manufacturing purposes; the presence and/or concentration of the oligosaccharide preparation in nutritional compositions can be selectively determined and/or detected. Further described herein are methods of producing the oligosaccharide preparations and nutritional compositions, and methods of analyzing and quantifying the same.

The following description and examples illustrate embodiments of the present disclosure in detail. It is to be understood that this present disclosure is not limited to the particular embodiments described herein and as such can vary. Those of skill in the art will recognize that there are numerous variations and modifications of this present disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

I. Definitions

As used herein the term "administering" includes providing a synthetic oligosaccharide preparation, a nutritional composition, a liquid, or an animal feed composition described herein, to an animal such that the animal may ingest the synthetic oligosaccharide preparation, the nutritional composition, the liquid, or the animal feed composition. In such embodiments, the animal ingests some portion of the synthetic oligosaccharide preparation, the nutritional composition, or the animal feed composition. In some embodiments, the animal ingests some portion of the synthetic oligosaccharide preparation, the nutritional composition, the liquid, or the animal feed composition in every 24-hour period or every other 24-hour period for at least 7 days, 14 days, 21 days, 30 days, 45 days, 60 days, 75 days, 90 days or 120 days. In some embodiments, the oligosaccharide preparation may be dissolved in water or another liquid, and the animal ingests some portion of the oligosaccharide preparation by drinking the liquid. In certain embodiments, the oligosaccharide is provided to the animal via its drinking water. In certain embodiments, the oligosaccharide preparation, nutritional composition, liquid, or animal feed composition is consumed at will.

As used herein, the term "inclusion level" or "dose" refers to the concentration of an oligosaccharide preparation in a nutritional composition, a liquid, a diet, or an animal feed composition provided to the animal. In some embodiments, the inclusion level is measured as the mass concentration of the oligosaccharide preparation in the final nutritional composition, liquid, diet, or animal feed. For example, the inclusion level may be measured in units of parts per million (ppm) of the oligosaccharide on a dry solids weight basis per the total weight of the final nutritional composition, liquid, diet, or animal feed. In certain embodiments, the dry solids mass of the oligosaccharide preparation is measured as the dry-basis mass of DP1+ species. In other embodiments, the dry solids mass of the oligosaccharide preparation is measured as the dry-basis mass of DP2+ species.

As used herein, the term "specific dose" refers to the quantity of an oligosaccharide preparation consumed by an animal per unit of time and relative to its body mass. In some embodiments, the specific dose may be measured in units of mg of oligosaccharide preparation (on a dry solids-basis) per kg of body weight of the animal per day (i.e., mg/kg/day).

As used herein, the term "anhydro-subunit" refers to a product of thermal dehydration of a monosaccharide (or monosaccharide subunit) or a sugar caramelization product. For example, an "anhydro-subunit" can be an anhydro-monosaccharide such as anhydro-glucose. As another example, an "anhydro-subunit" can be linked with one or more regular or anhydro-monosaccharide subunits via glycosidic linkage.

The term "oligosaccharide" refers to a monosaccharide or a compound containing two or more monosaccharide subunits linked by glycosidic bonds. As such, an oligosaccharide includes a regular monosaccharide; an anhydro-monosaccharide; or a compound containing two or more monosaccharide subunits, wherein one or more monosaccharide subunits are optionally, independently replaced by one or more anhydro-subunits. An oligosaccharide can be functionalized. As used herein, the term oligosaccharide encompasses all species of the oligosaccharide, wherein each of the monosaccharide subunit in the oligosaccharide is independently and optionally functionalized and/or replaced with its corresponding anhydro-monosaccharide subunit.

As used herein, the term "oligosaccharide preparation" refers to a preparation that comprises at least one oligosaccharide.

As used herein, the term "gluco-oligosaccharide" refers to a glucose or a compound containing two or more glucose monosaccharide subunits linked by glycosidic bonds. As such, a gluco-oligosaccharide includes a glucose; an anhydro-glucose; or a compound containing two or more glucose monosaccharide subunits linked by glycosidic bonds, wherein one or more of said glucose monosaccharide subunits are each optionally and independently replaced with an anhydro-glucose subunit.

As used herein, the term "galacto-oligosaccharide" refers to a galactose or a compound containing two or more galactose monosaccharide subunits linked by glycosidic bonds. As such, a galacto-oligosaccharide includes a galactose; an anhydro-galactose or a compound containing two or more galactose monosaccharide subunits linked by glycosidic bonds, wherein one or more of said galactose monosaccharide subunits are each optionally and independently replaced with an anhydro-galactose subunit.

As used herein, the term "gluco-galacto-oligosaccharide preparation" refers to a composition that is produced from a complete or incomplete sugar condensation reaction of glucose and galactose. Accordingly, in some embodiments, a gluco-galactose-oligosaccharide preparation comprises gluco-oligosaccharides, galacto-oligosaccharides, compounds containing one or more glucose monosaccharide subunits and one or more galactose monosaccharide subunits linked by glycosidic bonds, or a combination thereof. In some embodiments, a gluco-galactose-oligosaccharide preparation comprises gluco-oligosaccharides and compounds containing one or more glucose monosaccharide subunits and one or more galactose monosaccharide subunits linked by glycosidic bonds. In some embodiments, a gluco-galactose-oligosaccharide preparation comprises galacto-oligosaccharides and compounds containing one or more glucose monosaccharide subunits and one or more galactose monosaccharide subunits linked by glycosidic bonds. In some embodiments, a gluco-galactose-oligosaccharide preparation comprises compounds containing one or more glucose monosaccharide subunits and one or more galactose monosaccharide subunits linked by glycosidic bonds.

As used herein, the term "monosaccharide unit" and "monosaccharide subunit" are used interchangeably. A "monosaccharide subunit" refers to a monosaccharide monomer in an oligosaccharide. For an oligosaccharide having a degree of polymerization of 1, the oligosaccharide can be referred to as a monosaccharide subunit or monosaccharide. For an oligosaccharide having a degree of polymerization of 2 or higher, its monosaccharide subunits are linked via glycosidic bonds.

As used herein, the term "regular monosaccharide" refers to a monosaccharide that does not contain an anhydro-subunit. The term "regular disaccharide" refers to a disaccharide that does not contain an anhydro-subunit. Accordingly, the term "regular subunit" refers to a subunit that is not an anhydro-subunit.

The term "relative abundance" or "abundance," as used herein, refers to the abundance of a species in terms of how common or rare the species exists. For example, a DP1 fraction comprising 10% anhydro-subunit containing oligosaccharides by relative abundance can refer to a plurality of DP1 oligosaccharides, wherein 10% of the DP1 oligosaccharides are anhydro-monosaccharides. The relative abundance, e.g., for a certain DP fraction of oligosaccharides, can be determined by suitable analytical instrumentations, for example, mass spectrometry and liquid chromatography such as LC-MS/MS, GC-MS, HPLC-MS, and MALDI-MS. In some embodiments, the relative abundance is determined by integrating the area under the peaks of the chromatographs (e.g., LC-MS/MS, GC-MS, and HPLC-MS) that correspond to the fractions of interest. In some embodiments, the relative abundance is determined by the peak intensities (e.g., MALDI-MS). In some embodiments, the relative abundance is determined by a combination of analytical methods such as a weight determination after separation by liquid chromatography.

As used herein, the singular forms "a," "and," and "the" include plural referents unless the context clearly dictates otherwise. Thus, for example, reference to "an agent" includes a plurality of such agents, and reference to "the oligosaccharide" includes reference to one or more oligosaccharides (or to a plurality of oligosaccharides) and equivalents thereof known to those skilled in the art, and so forth.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. In some embodiments, the term "about" means within 15%, 10%, 9%, 8%, 7%, 6%, 5%, 4%, 3%, 2%, 1%, 0.5%, 0.1%, or 0.05% of a given value or range.

The term "comprising" (and related terms such as "comprise" or "comprises" or "having" or "including") is intended to include, but not necessarily be limited to the things so described.

II. Composition of Oligosaccharide Preparations

Herein disclosed is an oligosaccharide preparation suitable for use in nutritional compositions. In one aspect, describe herein is an oligosaccharide preparation comprising at least n fractions of oligosaccharides each having a distinct degree of polymerization selected from 1 to n (DP1 to DPn fractions), wherein n is an integer greater than or equal to 2. In some embodiments, n is an integer greater than 2, such as 3, 4, 5, 6, 7, 8, 9, and 10. In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, each of the 1 to n fraction in the oligosaccharide preparation independently comprises from 0.1% to 90% anhydro-subunit containing oligosaccharides by relative abundance as measured by mass spectrometry or by LC-MS/MS or GC-MS. In some embodiments, each of the 1 to n fraction in the oligosaccharide preparation independently comprises from about 0.1% to about 15% anhydro-subunit containing oligosaccharides. In some embodiments, each of the 1 to n fraction in the oligosaccharide preparation independently comprises from about 0.5% to about 15% anhydro-subunit containing oligosaccharides. In some embodiments, the DP1 and DP2 fractions each independently comprises from about 0.1% to about 15% of anhydro-subunit containing oligosaccharides by relative abundance as measured by mass spectrometry such as MALDI-MS or by LC-MS/MS or GC-MS. In some embodiments, the DP1 and DP2 fractions each independently comprises from about 0.5% to about 15% of anhydro-subunit containing oligosaccharides. In some embodiments, the DP1 and DP2 fractions each independently comprises from about 0.1%, 0.2%, 0.3%, 0.4%, 0.5%, 0.8%, 1%, 2% or 3% to about 8%, 9%, 10%, 11%, 12%, 13%, 14%, or 15% of anhydro-subunit containing oligosaccharides by relative abundance as measured by mass spectrometry, LC-MS/MS or GC-MS. In some embodiments, the relative abundance of oligosaccharides in each fraction decreases monotonically with its degree of polymerization.

In one aspect, a described oligosaccharide preparation is a synthetic oligosaccharide preparation. In some embodiments, a synthetic oligosaccharide preparation refers to a plurality of oligosaccharides produced by a process that does not require live organisms. In some embodiments, a synthetic oligosaccharide preparation refers to a plurality of oligosaccharides produced by a process that does not require enzymes. In some embodiments, a synthetic oligosaccharide preparation refers to a plurality of oligosaccharides produced by a chemical process. In certain embodiments, a synthetic oligosaccharide preparation refers to a plurality of oligosaccharides produced by the condensation of sugars.

Prebiotic Utility of Oligosaccharides

Herein disclosed are oligosaccharide preparations comprising anhydro-sugar components and/or sugar dehydration product components that exhibit complex functional modulation of a microbial community, such as the animal gut microbiome. The oligosaccharide preparations provide a utility to regulate the utilization of fermentable carbon by microflora and direct metabolic flux to beneficial species, thus providing a microbiome-mediated health or nutritional benefit.

Indigestible carbohydrates can act as prebiotics by providing a fermentable carbon source to a microbial community. For example, diets rich in soluble plant fiber have been identified for their ability to nourish the gut microflora. Additionally, bifidogenic prebiotics support the growth of bifidobacteria (e.g., members of genus *Bifidobacterium*) and lactogenic prebiotics support the growth of *Lactobacillus* species.

Prebiotic fiber may be fermented to beneficial chemical species such as short chain fatty acids (SCFAs). Prebiotic fibers include: resistant starches; cellulose; pectins such as rhamnogalactans, arabinogalactans, arabinans; hemicelluloses such as arabinoxylans, xyloglucans, glucomannans, galactomannans and b-glucans; polyfructans such as inulin and levan; and gums such as alginate. Inulin is a common bifidogenic prebiotic fiber.

In other cases, prebiotics act by hindering the ability of pathogenic bacteria to engraft and thus infect a host organism via anti-adherence mechanisms such as the competitive binding of cell surface receptor cites. Certain galacto-oligosaccharides provide effective anti-adherence of various enteropathogenic organisms, such as *Escherichia* species.

Prebiotics are typically provided to a host animal by incorporation into the diet, upon which they exhibit a dose-dependent response (at least up to a saturation threshold). For example, providing a higher dose of a bifidogenic prebiotic such as inulin tends to provide a larger increase in the population of *Bifidobacterium* species. Higher doses of inulin correspond to higher production of SCFAs through fermentation. This is because the prebiotic provides a metabolic carbon source and more carbon translates to more fermented product. Similarly, providing a higher dose of an anti-adherence prebiotic provides a likelihood of competitively binding surface receptor sites.

Certain carbohydrate species comprising modified monomeric subunits may affect the manner in which microbial systems utilize other carbohydrates otherwise available to them as a prebiotic source. For example, such carbohydrate species may be a modified carbohydrate species that modulate the bacterial starch utilization system (SUS), i.e., proteins responsible for the cell-surface recognition, glycosidic cleavage, and importation of starch metabolites.

Carbohydrate compositions capable of complex modulation of the microbiota of animals have utility as feed additives that improve animal health and nutrition via their impact on the animal microbiome. For example, modulation of butyrate production by the gut microflora confers health benefits to the animal by promoting a healthy gut mucosa, barrier function, and via anti-inflammatory effects. Modulation of propionic acid production affects the metabolic energy extracted from the animal's diet via increased gluconeogenesis. Relevant microbial communities include, for example, ileal, jejunal, and cecal and/or fecal microbiota in poultry, pigs, dogs, cats, horses, or the ruminant microbiota of cattle, cows, sheep, etc. Other microbial communities include the skin microflora, nasal microflora, etc.

Further, herein disclosed oligosaccharide preparations are advantageous in that they can be selectively analyzed and quantified in a complex nutritional composition such as complete animal feed due to the presence of anhydro-subunits. It is of commercial utility to assay for the presence and/or concentration of feed additives such as oligosaccharide preparations. Such assay may be performed for the purpose of quality control, to determine whether the additive was blended consistently with the base nutritional composition to provide a final nutritional composition comprising the additive at the intended dose or level of inclusion.

However, the nutritional compositions themselves comprise a large quantity and diversity of carbohydrate structures (e.g., starch, plant fibers and pectins). It is therefore particularly challenging to distinguish small quantities of oligosaccharide-based feed additives from the vast sea of other carbohydrates present as base of the nutritional composition. As such, the herein disclosed oligosaccharide preparation provides a means to distinguish itself from other carbohydrates sources in the nutritional composition through the anhydro-subunits.

Degree of Polymerization (DP) Distribution

In some embodiments, a herein described oligosaccharide preparation comprises at least n fractions of oligosaccharides, each fraction having a distinct degree of polymerization selected from 1 to n (DP1 to DPn fractions). In some embodiments, the oligosaccharide preparation comprises n fractions of oligosaccharides, each fraction having a distinct degree of polymerization selected from 1 to n (DP1 to DPn fractions). In some embodiments, the DP1 fraction comprises one or more monosaccharides and/or one or more anhydro-monosaccharides. For example, in some embodiments, the DP1 fraction comprises glucose, galactose, fructose, 1,6-anhydro-β-D-glucofuranose, 1,6-anhydro-β-D-glucopyranose, or any combination thereof. In some embodiments, the DP2 fraction comprises one or more regular disaccharides and one or more anhydro-subunit containing disaccharides. In some embodiments, the DP2 fraction comprises lactose.

In some embodiments, n is at least 2, at least 3, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100. In some embodiments, n is 2, 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, n is less than 10, less than 11, less than 12, less than 13, less than 14, less than 15, less than 16, less than 17, less than 18, less than 19, less than 20, less than 21, less than 22, less than 23, less than 24, less than 25, less than 26, less than 27, less than 28, less than 29, less than 30, less than 31, less than 32, less than 33, less than 34, less than 35, less than 36, less than 37, less than 38, less than 39, less than 40, less than 41, less than 42, less than 43, less than 44, less than 45, less than 46, less than 47, less than 48, less than 49, less than 50, less than 51, less than 52, less than 53, less than 54, less than 55, less than 56, less than 57, less than 58, less than 59, less than 60, less than 61, less than 62, less than 63, less than 64, less than 65, less than 66, less than 67, less than 68, less than 69, less than 70, less than 71, less than 72, less than 73, less than 74, less than 75, less than 76, less than 77, less than 78, less than 79, less than 80, less than 81, less than 82, less than 83, less than 84, less than 85, less than 86, less than 87, less than 88, less than 89, less than 90, less than 91, less than 92, less than 93, less than 94, less than 95, less than 96, less than 97, less than 98, less than 99, or less than 100. In some embodiments, n is from 2 to 100, from 5 to 90, from 10 to 90, from 10 to 80, from 10 to 70, from 10 to 60, from 10 to 50, from 10 to 40, from 10 to 30, from 15 to 60, from 15 to 50, from 15 to 45, from 15 to 40, from 15 to 35, or from 15 to 30.

Figure 2:
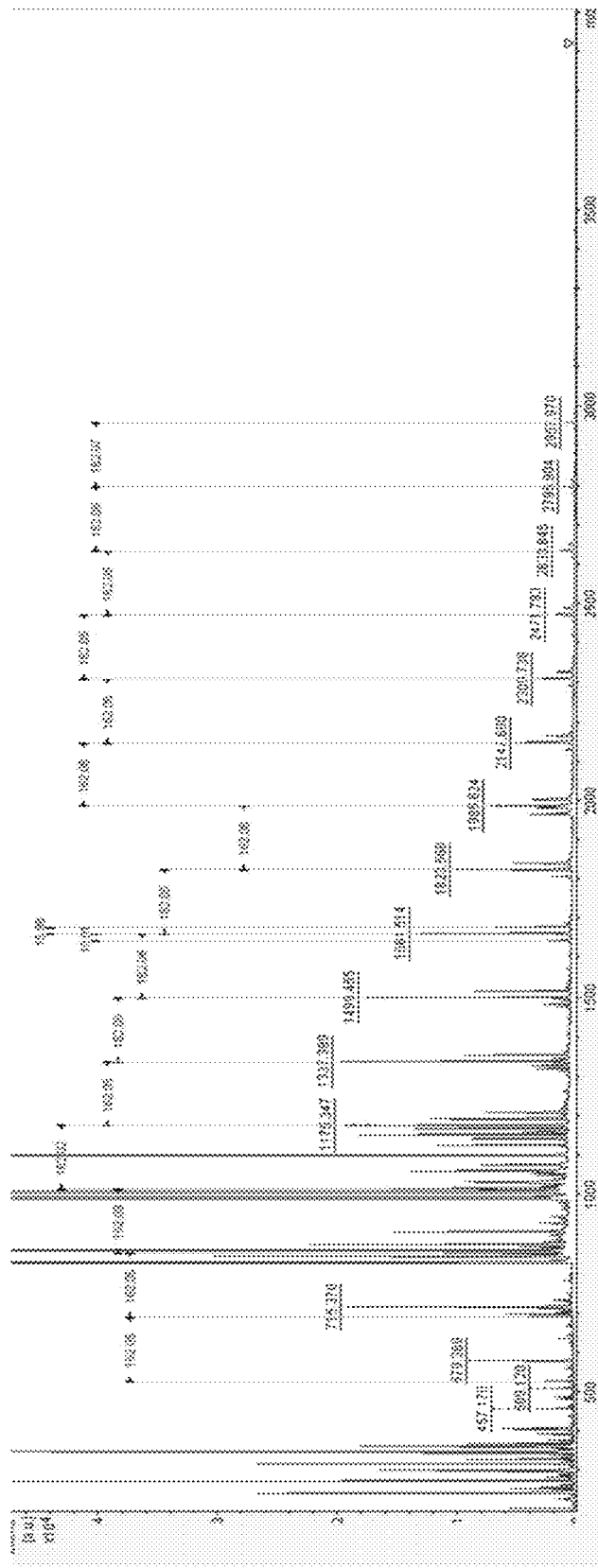
FIG. 2 illustrates a MALDI-MS spectrum of an oligosaccharide preparation from Example 9.7 that demonstrates the presence of anhydro-subunits.

A distribution of the degree of polymerization of the oligosaccharide preparation can be determined by any suitable analytical method and instrumentation, including but not limited to end group method, osmotic pressure (osmometry), ultracentrifugation, viscosity measurements, light scattering method, size exclusion chromatography (SEC), SEC-MALLS, field flow fractionation (FFF), asymmetric flow field flow fractionation (A4F), high-performance liquid chromatography (HPLC), and mass spectrometry (MS). For example, the distribution of the degree of polymerization may be determined and/or detected by mass spectrometry, such as matrix-assisted laser desorption/ionization (MALDI)-MS, liquid chromatography (LC)-MS, or gas chromatography (GC)-MS. For another example, the distribution of the degree of polymerization can be determined and/or detected by SEC, such as gel permeation chromatography (GPC). As yet another example, the distribution of the degree of polymerization can be determined and/or detected by HPLC, FFF, or A4F. In some embodiments, the distribution of the degree of polymerization is determined and/or detected by MALDI-MS. In some embodiments, the distribution of the degree of polymerization is determined and/or detected by GC-MS or LC-MS. In some embodiments, the distribution of the degree of polymerization is determined and/or detected by SEC. In some embodiments, the distribution of the degree of polymerization is determined and/or detected by HPLC. In some embodiments, the distribution of the degree of polymerization is determined and/or detected by a combination of analytical instrumentations such as MALDI-MS and SEC. In some embodiments, the degree of polymerization of the oligosaccharide preparation can be determined based on its molecular weight and molecular weight distribution. For example, FIG. 2 shows a MALDI-MS spectrum that illustrates the degrees of polymerizations of various fractions and the presence of anhydro-subunit containing oligosaccharides (the −18 g/mol MW offset peaks) in all of the observed fractions.

In some embodiments, the relative abundance of oligosaccharides in a majority of the fractions decreases monotonically with its degree of polymerization. In some embodiments, the relative abundance of oligosaccharides of less than 6, less than 5, less than 4, less than 3, or less than 2 fractions of the oligosaccharide preparation do not decrease monotonically with its degree of polymerization.

In some embodiments, the relative abundance of oligosaccharides in at least 5, at least 10, at least 15, at least 20, at least 25, at least 30, at least 35, at least 40, at least 45, or at least 50 DP fractions decreases monotonically with its degree of polymerization. In some embodiments, the relative abundance of oligosaccharides in at least 5, at least 10, at least 15, at least 20, at least 25, at least 30, at least 35, at least 40, at least 45, or at least 50 consecutive DP fractions decreases monotonically with its degree of polymerization. In some embodiments, the relative abundance of oligosaccharides in at least 5, at least 10, at least 20, or at least 30 DP fractions decreases monotonically with its degree of polymerization. In some embodiments, the relative abundance of oligosaccharides in at least 5, at least 10, at least 20, or at least 30 consecutive DP fractions decreases monotonically with its degree of polymerization.

Figure 10:
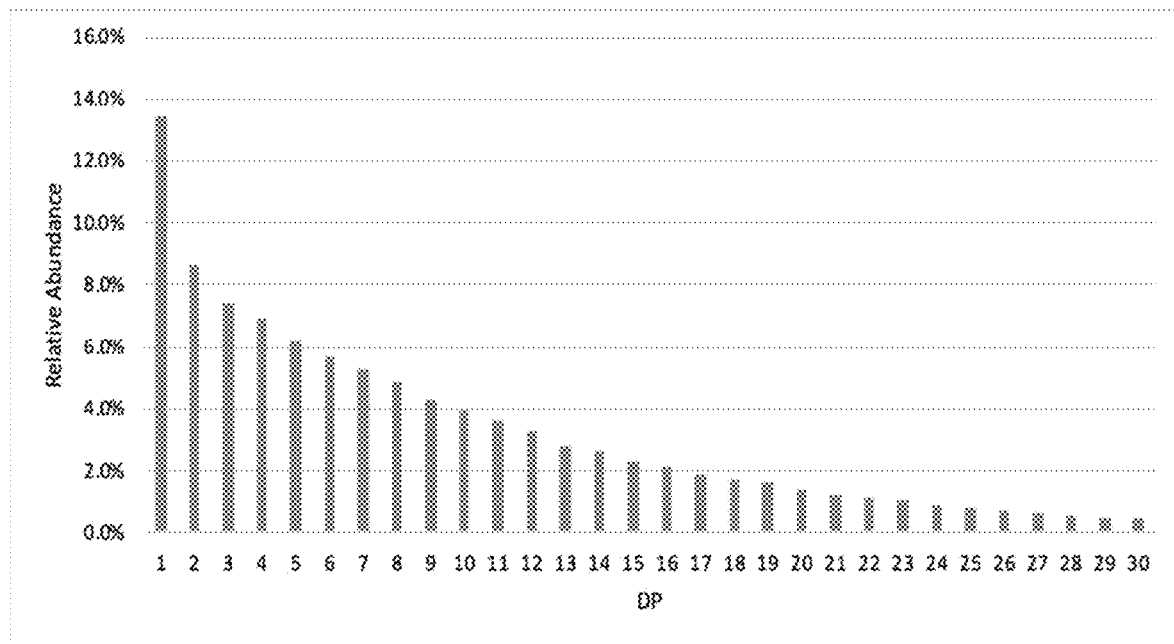
FIG. 10 illustrates an oligosaccharide preparation with a monotonically decreasing DP distribution as determined by size exclusion chromatography.
Figure 11:
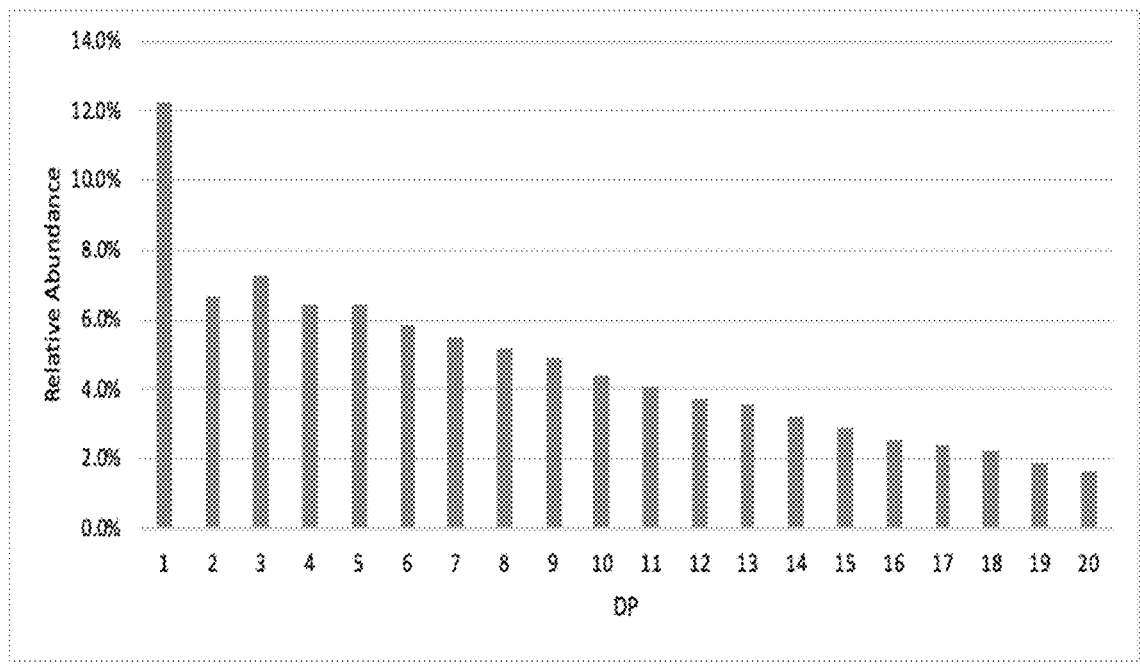
FIG. 11 illustrates an oligosaccharide preparation with a non-monotonically decreasing DP distribution as determined by size exclusion chromatography.

In some embodiments, the relative abundance of oligosaccharides in each of the n fractions decreases monotonically with its degree of polymerization. For example, FIG. 10 provides an example of a DP distribution where the relative abundance of oligosaccharides in each of the n fractions decrease monotonically with its DP. For example, in some embodiments, only the relative abundance of oligosaccharides in the DP3 fraction does not decrease monotonically with its degree of polymerization, i.e., the relative abundance of oligosaccharides in the DP3 fraction is lower than the relative abundance of oligosaccharides in the DP4 fraction. In some embodiments, the relative abundance of oligosaccharides in the DP2 fraction is lower than the relative abundance of oligosaccharides in the DP3 fraction. For example, FIG. 11 illustrates a degree of polymerization distribution wherein the relative abundance of oligosaccharides in the DP2 fraction does not decrease monotonically with its degree of polymerization.

In some embodiments, a herein described oligosaccharide preparation has a DP1 fraction content of from about 1% to about 50%, from about 1% to about 40%, from about 1% to about 35%, from about 1% to about 30%, from about 1% to about 25%, from about 1% to about 20%, from about 1% to about 15%, from about 5% to about 50%, from about 5% to about 40%, from about 5% to about 35%, from about 5% to about 30%, from about 5% to about 25%, from about 5% to about 20%, from about 5% to about 15%, from about 10% to about 50%, from about 10% to about 40%, from about 10% to about 35%, from about 10% to about 30%, from about 10% to about 25%, from about 10% to about 20%, or from about 10% to about 15% by weight or by relative abundance. In some embodiments, the oligosaccharide preparation has a DP1 fraction content of from about 10% to about 35%, from about 10% to about 20%, or from about 10% to about 15% by weight or by relative abundance. In some embodiments, the content of the DP1 fraction is determined by MALDI-MS. In some embodiments, the content of the DP1 fraction is determined by HPLC. In some embodiments, the content of the DP1 fraction is determined by LC-MS/MS or GC-MS.

In some embodiments, a herein described oligosaccharide preparation has a DP2 fraction content of from about 1% to about 35%, from about 1% to about 30%, from about 1% to about 25%, from about 1% to about 20%, from about 1% to about 15%, from about 1% to about 10%, from about 5% to about 30%, from about 5% to about 25%, from about 5% to about 20%, from about 5% to about 15%, or from about 5% to about 10% by weight or by relative abundance. In some embodiments, the oligosaccharide preparation has a DP2 fraction content of from about 5% to about 25%, from about 5% to about 20%, from about 5% to about 15%, or from about 5% to about 10% by weight or by relative abundance. In some embodiments, the content of the DP2 fraction is determined by MALDI-MS. In some embodiments, the content of the DP2 fraction is determined by HPLC. In some embodiments, the content of the DP2 fraction is determined by LC-MS/MS or GC-MS.

In some embodiments, a herein described oligosaccharide preparation has a DP3 fraction content of from about 1% to about 30%, from about 1% to about 25%, from about 1% to about 20%, from about 1% to about 15%, from about 1% to about 10%, from about 5% to about 30%, from about 5% to about 25%, from about 5% to about 20%, from about 5% to about 15%, or from about 5% to about 10% by weight or by relative abundance. In some embodiments, the oligosaccharide preparation has a DP3 fraction content of from about 1% to about 15%, from about 1% to about 10%, from about 5% to about 15%, or from about 5% to about 10% by weight or by relative abundance. In some embodiments, the content of the DP3 fraction is determined by MALDI-MS. In some embodiments, the content of the DP3 fraction is determined by HPLC. In some embodiments, the content of the DP3 fraction is determined by LC-MS/MS or GC-MS.

In some embodiments, a herein described oligosaccharide preparation has a DP4 fraction content of from about 0.1% to about 20%, from about 0.1% to about 15%, from about 0.1% to about 10%, from about 0.1% to about 5%, from about 1% to about 20%, from about 1% to about 15%, from about 1% to about 10%, or from about 1% to about 5% by weight or by relative abundance. In some embodiments, the oligosaccharide preparation has a DP4 fraction content of from about 1% to about 15%, from about 1% to about 10%, or from about 1% to about 5% by weight or by relative abundance. In some embodiments, a herein described oligosaccharide preparation has a DP5 fraction content of from about 0.1% to about 15%, from about 0.1% to about 10%, from about 0.1% to about 5%, from about 1% to about 15%, from about 1% to about 10%, or from about 1% to about 5% by weight or by relative abundance. In some embodiments, the oligosaccharide preparation has a DP5 fraction content of from about 1% to about 10% or from about 1% to about 5% by weight or by relative abundance. In some embodiments, the content of the DP4 and/or the DP5 fraction is determined by MALDI-MS. In some embodiments, the content of the DP4 and/or the DP5 fraction is determined by HPLC. In some embodiments, the content of the DP4 and/or the DP5 fraction is determined by LC-MS/MS or GC-MS.

In some embodiments, the ratio of DP2 fraction to DP1 fraction in the oligosaccharide preparation is from about 0.01 to about 0.8, from about 0.02 to about 0.7, from about 0.02 to about 0.6, from about 0.02 to about 0.5, from about 0.02 to about 0.4, from about 0.02 to about 0.3, from about 0.02 to about 0.2, from about 0.1 to about 0.6, from about 0.1 to about 0.5, from about 0.1 to about 0.4, or from about 0.1 to about 0.3 by their weight or relative abundance. In some embodiments, the ratio of DP2 fraction to DP1 fraction in the oligosaccharide preparation is from about 0.02 to about 0.4 by their weight or relative abundance.

In some embodiments, the ratio of DP3 fraction to DP2 fraction in the oligosaccharide preparation is from about 0.01 to about 0.7, from about 0.01 to about 0.6, from about 0.01 to about 0.5, from about 0.01 to about 0.4, from about 0.01 to about 0.3, or from about 0.01 to about 0.2 by their weight or relative abundance. In some embodiments, the ratio of DP3 fraction to DP2 fraction in the oligosaccharide preparation is from about 0.01 to about 0.3 by their weight or relative abundance.

In some embodiments, the aggregate content of DP1 and DP2 fractions in the oligosaccharide preparation is less than 70%, less than 60%, less than 50%, less than 40%, less than 30%, less than 20%, or less than 10% by weight or by relative abundance. In some embodiments, the aggregate content of DP1 and DP2 fractions in the oligosaccharide preparation is less than 50%, less than 30%, or less than 10% by weight or by relative abundance.

In some embodiments, an oligosaccharide preparation described herein has a mean DP value within a range of 2 to 10. In some embodiments, the oligosaccharide preparation has a mean DP value of from about 2 to about 8, from about 2 to about 5, or from about 2 to about 4. In some embodiments, the oligosaccharide preparation has a mean DP value of about 3.5. The mean DP value can be determined by SEC or by elemental analysis.

Anhydro-Subunit Level

In some embodiments, each of the n fractions of oligosaccharides in a herein described oligosaccharide preparation independently comprises an anhydro-subunit level. For instance, in some embodiments, the DP1 fraction comprises about 10% of anhydro-subunit containing oligosaccharides by relative abundance, and the DP2 fraction comprises about 15% of anhydro-subunit containing oligosaccharides by relative abundance. For another example, in some embodiments, DP1, DP2, and DP3 fractions each comprises about 5%, about 10%, and about 2% of anhydro-subunit containing oligosaccharides by relative abundance, respectively. In some embodiments, two or more fractions of oligosaccharides comprise similar levels of anhydro-subunit containing oligosaccharides. For example, in some embodiments, the DP1 and DP3 fractions each comprises about 5% of anhydro-subunit containing oligosaccharides by relative abundance.

In some embodiments, each of the 1 to n fractions in a herein described oligosaccharide preparation independently comprises from about 0.1% to 15% of anhydro-subunit containing oligosaccharides by relative abundance as measured by mass spectrometry, LC-MS/MS or GC-MS. In some embodiments, each of the 1 to n fractions in the oligosaccharide preparation independently comprises from about 0.5% to 15% of anhydro-subunit containing oligosaccharides by relative abundance as measured by mass spectrometry, LC-MS/MS or GC-MS. In some embodiments, LC-MS/MS is used to determine the relative abundance for oligosaccharides in the DP1, DP2, and/or DP3 fractions. In some embodiments, GC-MS or LC-MS/MS is used to determine the relative abundance for oligosaccharides in the DP1, DP2, and/or DP3 fractions. In some embodiments, MALDI-MS is used to determine the relative abundance for oligosaccharides in the DP3 fraction, DP4 fraction, or in a higher DP fraction. In some embodiments, the relative abundance of a certain fraction is determined by integrating the area under the peaks of the LC-MS/MS chromatogram that are designated as corresponding to that fraction. In some embodiments, the relative abundance of a certain fraction is determined by integrating the area under the peaks of the GC-MS chromatogram that are designated as corresponding to that fraction.

The level of anhydro-subunits can be determined by any suitable analytical methods, such as nuclear magnetic resonance (NMR) spectroscopy, mass spectrometry, HPLC, FFF, A4F, or any combination thereof. In some embodiments, the level of anhydro-subunits is determined, at least in part, by mass spectrometry such as MALDI-MS. In some embodiments, the level of anhydro-subunits is determined, at least in part, by NMR. In some embodiments, the level of anhydro-subunits containing oligosaccharides is determined, at least in part, by HPLC. In some embodiments, the level of anhydro-subunits containing oligosaccharides is determined by MALDI-MS, as illustrated by the −18 g/mol MW offset peaks in FIG. 2. In some embodiments, the presence and the type of species of anhydro-subunits can be determined and/or detected by NMR, as illustrated by Example 11, FIG. 3, and FIG. 4. In some embodiments, the relative abundance of anhydro-subunit containing oligosaccharides is determined by MALDI-MS. In some embodiments, the relative abundance of anhydro-subunit containing oligosaccharides is determined by LC-MS/MS, as illustrated in FIGS. 15A-15C, 16A-16C, 17A-17C and 18A-18C. In some embodiments, the relative abundance of anhydro-subunit containing oligosaccharides is determined by GC-MS, as illustrated in FIGS. 19A-19B, 20A-20B, 21A-21B and 22A-22B.

In some embodiments, at least one fraction of a herein described oligosaccharide preparation comprises less than 80%, less than 70%, less than 60%, less than 50%, less than 40%, less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, at least one fraction of a herein described oligosaccharide preparation comprises less than 10%, less than 9%, less than 8%, less than 7%, less than 6%, less than 5%, less than 4%, less than 3%, or less than 2% of anhydro-subunit containing oligosaccharides by relative abundance. In other embodiments, at least one fraction of a herein described oligosaccharide preparation comprises greater than 0.5%, greater than 0.8%, greater than 1%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%, greater than 30%, greater than 40%, greater than 50%, greater than 60%, greater than 70%, or greater than 80% of anhydro-subunit containing oligosaccharides by relative abundance. In other embodiments, at least one fraction of a herein described oligosaccharide preparation comprises greater than 20%, greater than 21%, greater than 22%, greater than 23%, greater than 24%, greater than 25%, greater than 26%, greater than 27%, greater than 28%, greater than 29%, or greater than 30% of anhydro-subunit containing oligosaccharides by relative abundance. In some embodiments, at least one fraction (such as DP1, DP2, and/or DP3) of the oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, or about 30% of anhydro-subunit containing oligosaccharides by relative abundance. In some embodiments, at least one fraction (such as DP1, DP2, and/or DP3) of the oligosaccharide preparation comprises about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, or about 10% of anhydro-subunit containing oligosaccharides by relative abundance. In some embodiments, at least one fraction (such as DP1, DP2, and/or DP3) of the oligosaccharide preparation comprises from about 0.1% to about 90%, from about 0.5% to about 90%, from about 0.5% to about 80%, from about 0.5% to about 70%, from about 0.5% to about 60%, from about 0.5% to about 50%, from about 0.5% to about 40%, from about 0.5% to about 30%, from about 0.5% to about 20%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 1% to about 10%, from about 2% to about 9%, from about 2% to about 8%, from about 2% to about 7%, from about 2% to about 6%, from about 2% to about 5%, from about 2% to about 4%, from about 2% to about 3%, or from about 5% to about 10% of anhydro-subunit containing oligosaccharides by relative abundance. In some embodiments, the DP1 and DP2 fractions of the oligosaccharide preparation each independently comprises anhydro-subunit containing oligosaccharides within a range of from about 0.1%, 0.5%, 0.6%, 0.7%, 0.8%, 0.9%, 1%, 1.1%, 1.2%, 1.3%, 1.4%, or 1.5% to about 8%, 9%, 10%, 11%, 12%, or 15% by relative abundance as measured by mass spectrometry, LC-MS/MS, or GC-MS. In some embodiments, the DP1 and DP2 fractions each independently comprises from about 0.5% to about 15% of anhydro-subunit containing oligosaccharides by relative abundance as measured by mass spectrometry or by LC-MS/MS or GC-MS.

In some embodiments, each fraction of a herein described oligosaccharide preparation comprises less than 80%, less than 70%, less than 60%, less than 50%, less than 40%, less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, or less than 2% of anhydro-subunit containing oligosaccharides by relative abundance. In some embodiments, each fraction of a herein described oligosaccharide preparation comprises less than 10%, 9%, 8%, 7%, 6%, 5%, 4%, 3%, or 2% anhydro-subunit containing oligosaccharides by relative abundance. In other embodiments, each fraction of a herein described oligosaccharide preparation comprises greater than 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, or 80% of anhydro-subunit containing oligosaccharides by relative abundance. In other embodiments, each fraction of a herein described oligosaccharide preparation comprises greater than 20%, 21%, 22%, 23%, 24%, 25%, 26%, 27%, 28%, 29%, or 30% anhydro-subunit containing oligosaccharides by relative abundance. In some embodiments, each fraction of a herein described oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, or about 30% of anhydro-subunit containing oligosaccharides by relative abundance. In some embodiments, each fraction of a herein described oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of anhydro-subunit containing oligosaccharides by relative abundance. In some embodiments, each fraction of a herein described oligosaccharide preparation comprises from about 0.1% to about 90%, from about 0.1% to about 15%, from about 0.5% to about 90%, from about 0.5% to about 80%, from about 0.5% to about 70%, from about 0.5% to about 60%, from about 0.5% to about 50%, from about 0.5% to about 40%, from about 0.5% to about 30%, from about 0.5% to about 20%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 2% to about 9%, from about 2% to about 8%, from about 2% to about 7%, from about 2% to about 6%, from about 2% to about 5%, from about 2% to about 4%, from about 2% to about 3%, or from about 5% to about 10% of anhydro-subunit containing oligosaccharides by relative abundance.

In some embodiments, a herein described oligosaccharide preparation comprises less than 80%, less than 70%, less than 60%, less than 50%, less than 40%, less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the oligosaccharide preparation comprises less than 10%, 9%, 8%, 7%, 6%, 5%, 4%, 3%, or 2% anhydro-subunit containing oligosaccharides by relative abundance. In other embodiments, the oligosaccharide preparation comprises greater than 0.5%, greater than 0.8%, greater than 1%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%, greater than 30%, greater than 40%, greater than 50%, greater than 60%, greater than 70%, or greater than 80% anhydro-subunit containing oligosaccharides by relative abundance. In other embodiments, the oligosaccharide preparation comprises greater than 20%, 21%, 22%, 23%, 24%, 25%, 26%, 27%, 28%, 29%, or 30% anhydro-subunit containing oligosaccharides by relative abundance. In some embodiments, the oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, or about 30% of anhydro-subunit containing oligosaccharides by relative abundance. In some embodiments, the oligosaccharide preparation comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of anhydro-subunit containing oligosaccharides by relative abundance. In some embodiments, the oligosaccharide preparation comprises from about 0.1% to about 90%, from about 0.1% to about 15%, from about 0.5% to about 90%, from about 0.5% to about 80%, from about 0.5% to about 70%, from about 0.5% to about 60%, from about 0.5% to about 50%, from about 0.5% to about 40%, from about 0.5% to about 30%, from about 0.5% to about 20%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 2% to about 9%, from about 2% to about 8%, from about 2% to about 7%, from about 2% to about 6%, from about 2% to about 5%, from about 2% to about 4%, from about 2% to about 3%, or from about 5% to about 10% of anhydro-subunit containing oligosaccharides by relative abundance.

In some embodiments, the DP1 fraction of a herein described oligosaccharide preparation comprises less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the DP1 fraction of a herein described oligosaccharide preparation comprises greater than 0.1%, greater than 0.5%, greater than 0.8%, greater than 1%, greater than 1.5%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, or greater than 15% of anhydro-subunit containing oligosaccharides by relative abundance. In some embodiments, the DP1 fraction of a herein described oligosaccharide preparation comprises about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of anhydro-subunit containing oligosaccharides by relative abundance. In some embodiments, the DP1 fraction of a herein described oligosaccharide preparation comprises from about 0.1% to about 15%, from about 0.1% to about 20%, from about 0.5% to about 20%, from about 0.5% to about 10%, from about 0.5% to about 15%, from about 1% to about 20%, from about 1% to about 15%, from about 1% to about 10%, from about 2% to about 14%, from about 3% to about 13%, from about 4% to about 12%, from about 5% to about 11%, from about 5% to about 10%, from about 6% to about 9%, or from about 7% to about 8% of anhydro-subunit containing oligosaccharides by relative abundance, or any ranges therebetween. In some embodiments, the DP1 fraction of a herein described oligosaccharide preparation comprises from about 0.5% to about 10% of anhydro-subunit containing oligosaccharides by relative abundance. In some embodiments, the relative abundance of anhydro-subunit containing oligosaccharides is determined by mass spectrometry such as MALDI-MS. In some embodiments, the relative abundance of anhydro-subunit containing oligosaccharides is determined by LC-MS/MS. In some embodiments, the relative abundance of anhydro-subunit containing oligosaccharides is determined by GC-MS.

In some embodiments, the DP2 fraction of a herein described oligosaccharide preparation comprises less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the DP2 fraction of a herein described oligosaccharide preparation comprises greater than 0.1%, greater than 0.5%, greater than 0.8%, greater than 1%, greater than 1.5%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, or greater than 15% of anhydro-subunit containing oligosaccharides by relative abundance. In some embodiments, the DP2 fraction of a herein described oligosaccharide preparation comprises about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of anhydro-subunit containing oligosaccharides by relative abundance. In some embodiments, the DP2 fraction of a herein described oligosaccharide preparation comprises from about 0.1% to about 15%, from about 0.1% to about 20%, from about 0.5% to about 20%, from about 0.5% to about 10%, from about 0.5% to about 15%, from about 1% to about 20%, from about 1% to about 15%, from about 1% to about 10%, from about 2% to about 14%, from about 3% to about 13%, from about 4% to about 12%, from about 5% to about 11%, from about 0.5% to about 10%, from about 6% to about 9%, or from about 7% to about 8% of anhydro-subunit containing oligosaccharides by relative abundance, or any ranges therebetween. In some embodiments, the DP2 fraction of a herein described oligosaccharide preparation comprises from about 5% to about 10% of anhydro-subunit containing oligosaccharides by relative abundance. In some embodiments, the relative abundance of anhydro-subunit containing oligosaccharides is determined by mass spectrometry such as MALDI-MS. In some embodiments, the relative abundance of anhydro-subunit containing oligosaccharides is determined by LC-MS/MS. In some embodiments, the relative abundance of anhydro-subunit containing oligosaccharides is determined by GC-MS.

In some embodiments, the DP3 fraction of a herein described oligosaccharide preparation comprises less than 30%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of anhydro-subunit containing oligosaccharides by relative abundance. In some embodiments, the DP3 fraction of a herein described oligosaccharide preparation comprises greater than 0.1%, greater than 0.5%, greater than 0.8%, greater than 1%, greater than 1.5%, greater than 2%, greater than 3%, greater than 4%, greater than 5%, greater than 6%, greater than 7%, greater than 8%, greater than 9%, greater than 10%, greater than 11%, greater than 12%, greater than 13%, greater than 14%, or greater than 15% of anhydro-subunit containing oligosaccharides by relative abundance. In some embodiments, the DP3 fraction of a herein described oligosaccharide preparation comprises about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of anhydro-subunit containing oligosaccharides by relative abundance. In some embodiments, the DP3 fraction of a herein described oligosaccharide preparation comprises from about 0.1% to about 15%, from about 0.1% to about 20%, from about 0.5% to about 20%, from about 0.5% to about 10%, from about 0.5% to about 15%, from about 1% to about 20%, from about 1% to about 15%, from about 1% to about 10%, from about 2% to about 14%, from about 3% to about 13%, from about 4% to about 12%, from about 5% to about 11%, from about 5% to about 10%, from about 6% to about 9%, or from about 7% to about 8% of anhydro-subunit containing oligosaccharides by relative abundance, or any ranges therebetween. In some embodiments, the DP3 fraction of a herein described oligosaccharide preparation comprises from about 0.5% to about 10% of anhydro-subunit containing oligosaccharides by relative abundance. In some embodiments, the relative abundance of anhydro-subunit containing oligosaccharides is determined by mass spectrometry such as MALDI-MS. In some embodiments, the relative abundance of anhydro-subunit containing oligosaccharides is determined by LC-MS/MS. In some embodiments, the relative abundance of anhydro-subunit containing oligosaccharides is determined by GC-MS.

In some embodiments, an anhydro-subunit containing oligosaccharide comprises one or more anhydro-subunits. For instance, a DP1 anhydro-subunit containing oligosaccharide comprises one anhydro-subunit. In some embodiments, a DPn anhydro-subunit containing oligosaccharide may comprise from 1 to n anhydro-subunits. For example, in some embodiments, a DP2 anhydro-subunit containing oligosaccharide comprises one or two anhydro-subunits. In some embodiments, each oligosaccharide in the oligosaccharide preparation independently comprises zero, one, or two anhydro-subunits. In some embodiments, more than 99%, 95%, 90%, 85%, 80%, 75%, 70%, 65%, 60%, 55%, 50%, 45%, 40%, 35%, or 30% of the anhydro-subunit containing oligosaccharides have only one anhydro-subunit. In some embodiments, more than 99%, 95%, 90%, 85%, or 80% of the anhydro-subunit containing oligosaccharides have only one anhydro-subunit.

In some embodiments, one or more oligosaccharides in the oligosaccharide preparation or in each fraction of the oligosaccharide preparation comprise 1, 2, 3, 4, 5, 6, 7, 8, 9, or 10 anhydro-subunits each linked via a glycosidic bond, wherein the glycosidic bonds linking each anhydro-subunit are independently chosen. In some embodiments, one or more oligosaccharides in the oligosaccharide preparation or in each fraction of the oligosaccharide preparation comprise 1, 2, or 3 anhydro-subunits each linked via a glycosidic bond, wherein the glycosidic bond linking each anhydro-subunit are independently chosen. In some embodiments, greater than 50%, 60%, 70%, 80%, 90%, or 99% of oligosaccharides in the oligosaccharide preparation or in each fraction comprise 1, 2, or 3 anhydro-subunits each linked via a glycosidic bond, wherein the glycosidic bond linking each anhydro-subunit are independently chosen. In some embodiments, one or more oligosaccharides in the oligosaccharide preparation or in each fraction comprise 1 anhydro-subunit linked via a glycosidic bond. In some embodiments, greater than 50%, greater than 60%, greater than 70%, greater than 80%, greater than 90%, or greater than 99% of oligosaccharides in the oligosaccharide preparation or in each fraction comprise 1 anhydro-subunit linked via a glycosidic bond.

Anhydro-Subunit Species

In some embodiments, the oligosaccharide preparation comprises different species of anhydro-subunits. In some embodiments, exemplary anhydro-subunit containing oligosaccharides are illustrated in FIG. 5, FIG. 12, and FIG. 13. In some embodiments, the oligosaccharide preparation comprises one or more anhydro-subunits that are products of thermal dehydration of monosaccharides, i.e., anhydro-monosaccharide subunits. In some embodiments, the oligosaccharide preparation comprises one or more anhydro-subunits that are products of reversible thermal dehydration of monosaccharides.

It is to be understood that an anhydro-monosaccharide (or an anhydro-monosaccharide subunit) refers to one or more species of the thermal dehydration products of the monosaccharide. For example, in some embodiments, an anhydro-glucose refers to 1,6-anhydro-β-D-glucopyranose (levoglucosan) or 1,6-anhydro-β-D-glucofuranose. In some embodiments, a plurality of anhydro-glucose refer to a plurality of 1,6-anhydro-β-D-glucopyranose (levoglucosan), a plurality of 1,6-anhydro-β-D-glucofuranose, a plurality of other thermal dehydration products of glucose, or any combination thereof. Similarly, in some embodiments, a plurality of anhydro-galactose refers to a plurality of any thermal dehydration products of galactose, or any combination thereof.

In some embodiments, an oligosaccharide preparation as described herein comprises one or more anhydro-glucose, anhydro-galactose, anhydro-mannose, anhydro-allose, anhydro-altrose, anhydro-gulose, anhydro-indose, anhydro-talose, anhydro-fructose, anhydro-ribose, anhydro-arabinose, anhydro-rhamnose, anhydro-lyxose, anhydro-xylose, or any combination of these subunits. In some embodiments, the oligosaccharide preparation comprises one or more anhydro-glucose, anhydro-galactose, anhydro-mannose, or anhydro-fructose subunits. In some embodiments, an oligosaccharide preparation as described herein comprises one or more of: 1,6-anhydro-3-O-β-D-glucopyranosyl-β-D-glucopyranose, 1,6-anhydro-3-O-α-D-glucopyranosyl-β-D-glucopyranose, 1,6-anhydro-2-O-β-D-glucopyranosyl-β-D-glucopyranose, 1,6-anhydro-2-O-α-D-glucopyranosyl-β-D-glucopyranose, 1,6-anhydro-β-D-cellobiose (cellobiosan), 1,6-anhydro-β-D-cellotriose (cellotriosan), 1,6-anhydro-β-D-cellotetraose (cellotetraosan), 1,6-anhydro-β-D-cellopentaose (cellopentaosan), and 1,6-anhydro-β-D-maltose (maltosan).

In some embodiments, the oligosaccharide preparation comprises one or more 1,6-anhydro-β-D-glucofuranose subunits. In some embodiments, the oligosaccharide preparation comprises one or more 1,6-anhydro-β-D-glucopyranose (levoglucosan) subunits. For example, FIG. 12 illustrates two DP1 anhydro-subunit containing oligosaccharides (levoglucosan and 1,6-anhydro-β-D-glucofuranose) and a DP2 anhydro-subunit containing oligosaccharide (anhydro-cellobiose).

The presence and the level of a species of anhydro-subunit may vary based on the feed sugars used to manufacture the oligosaccharide. For instance, in some embodiments, gluco-oligosaccharides comprise anhydro-glucose subunits, galacto-oligosaccharides comprise anhydro-galactose subunits, and gluco-galacto-oligosaccharides comprise anhydro-glucose and anhydro-galactose subunits.

In some embodiments, the oligosaccharide preparation comprises both 1,6-anhydro-β-D-glucofuranose and 1,6-anhydro-β-D-glucopyranose anhydro-subunits. In some embodiments, at least 0.1%, 1%, 5%, 10%, 20%, 30%, 40%, 50%, 60%, 70%, 80%, 90%, or 99% of anhydro-subunits are selected from a group consisting of 1,6-anhydro-β-D-glucofuranose and 1,6-anhydro-β-D-glucopyranose. In some embodiments, at least 1%, 5%, 10%, 20%, 30%, 40%, 50%, 60%, 70%, 80%, or 90% of anhydro-subunits are 1,6-anhydro-β-D-glucofuranose. In some embodiments, at least 1%, 5%, 10%, 20%, 30%, 40%, 50%, or 60% of anhydro-subunits are 1,6-anhydro-β-D-glucopyranose.

In some embodiments, the ratio of 1,6-anhydro-β-D-glucofuranose to 1,6-anhydro-β-D-glucopyranose is from about 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in the preparation. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in the preparation. In some embodiments, the ratio of 1,6-anhydro-β-D-glucofuranose to 1,6-anhydro-β-D-glucopyranose is about 2:1 in the preparation.

In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in each fraction. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in each fraction. In some embodiments, the ratio of 1,6-anhydro-β-D-glucofuranose to 1,6-anhydro-β-D-glucopyranose is about 2:1 in each fraction.

In some embodiments, the ratio of 1,6-anhydro-β-D-glucofuranose to 1,6-anhydro-β-D-glucopyranose is about from 10:1 to 1:10, 9:1 to 1:10, 8:1 to 1:10, 7:1 to 1:10, 6:1 to 1:10, 5:1 to 1:10, 4:1 to 1:10, 3:1 to 1:10, 2:1 to 1:10, 10:1 to 1:9, 10:1 to 1:8, 10:1 to 1:7, 10:1 to 1:6, 10:1 to 1:5, 10:1 to 1:4, 10:1 to 1:3, 10:1 to 1:2, or 1:1 to 3:1 in at least one fraction. In some embodiments, the ratio of 1,6-anhydro-β-D-glucofuranose to 1,6-anhydro-β-D-glucopyranose is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:8, 1:9, or 1:10 in at least one fraction. In some embodiments, the ratio of 1,6-anhydro-β-D-glucofuranose to 1,6-anhydro-β-D-glucopyranose is about 2:1 in at least one fraction.

In some embodiments, a herein described oligosaccharide preparation comprises anhydro-subunit containing DP2 oligosaccharides. In some embodiments, the oligosaccharide preparation comprises anhydro-lactose, anhydro-sucrose, anhydro-cellobiose, or a combination thereof. In some embodiment, the oligosaccharide preparation comprises from about 2 to 20, 2 to 15, 5 to 20, 5 to 15, or 5 to 10 species of DP2 anhydro-subunit containing oligosaccharides. In some embodiments, an oligosaccharide preparation described herein does not comprise cellobiosan or does not comprise a detectable level of cellobiosan.

In some embodiments, a herein described oligosaccharide preparation comprises one or more anhydro-subunits that are sugar caramelization products. In some embodiments, the oligosaccharide preparation comprises one or more anhydro-subunits are sugar caramelization products selected from the group consisting of: methanol; ethanol; furan; methyl glyoxal; 2-methyl furan; vinyl acetate; glycolaldehyde; acetic acid; acetol; furfural; 2-furanmethanol; 3-furanmethanol; 2-hydroxy cyclopent-2-en-1-one; 5-methyl furfural; 2(5H)-furanone; 2 methyl cyclopentenolone; levoglucosenone; cyclic hydroxyl lactone; 1,4,3,6-dianhydro-α-D-glucopyranose; dianhydro glucopyranose; and 5-hydroxy methyl furfural (5-hmf). In some embodiments, the oligosaccharide preparation comprises 5-hmf anhydro-subunits.

In some embodiments, in the oligosaccharide preparation or in at least one of the DP fractions, the anhydro-subunits that are caramelization products are less abundant than the anhydro-subunits that are products of thermal dehydration of a monosaccharide. In some embodiments, in the oligosaccharide preparation or in at least one of the fractions, the anhydro-subunits that are caramelization products are more abundant than the anhydro-subunits that are products of thermal dehydration of a monosaccharide. In some embodiments, in the oligosaccharide preparation or in at least one of the fractions, anhydro-subunits that are caramelization products and anhydro-subunits that are products of thermal dehydration of a monosaccharide have similar abundance.

In some embodiments, from about 0.01% to about 50%, from about 0.01% to about 40%, from about 0.01% to about 30%, from about 0.01% to about 20%, from about 0.01% to about 10%, from about 0.01% to about 5%, from about 0.01% to about 4%, from about 0.01% to about 3%, from about 0.01% to about 2%, from about 0.01% to about 1%, from about 0.01% to about 0.5%, from about 0.1% to about 50%, from about 0.1% to about 40%, from about 0.1% to about 30%, from about 0.1% to about 20%, from about 0.1% to about 10%, from about 0.1% to about 5%, from about 0.1% to about 4%, from about 0.1% to about 3%, from about 0.1% to about 2%, from about 0.1% to about 1%, or from about 0.1% to about 0.5% of the anhydro-subunits in a herein described oligosaccharide preparation are caramelization products. In some embodiments, from about 0.1% to about 5%, from about 0.1% to about 2%, or from about 0.1% to about 1% of the anhydro-subunits in the oligosaccharide preparation are caramelization products. In some embodiments, less than 50%, less than 40%, less than 30%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the anhydro-subunits in the oligosaccharide preparation are caramelization products.

In some embodiments, from about 0.01% to about 50%, from about 0.01% to about 40%, from about 0.01% to about 30%, from about 0.01% to about 20%, from about 0.01% to about 10%, from about 0.01% to about 5%, from about 0.01% to about 4%, from about 0.01% to about 3%, from about 0.01% to about 2%, from about 0.01% to about 1%, from about 0.01% to about 0.5%, from about 0.1% to about 50%, from about 0.1% to about 40%, from about 0.1% to about 30%, from about 0.1% to about 20%, from about 0.1% to about 10%, from about 0.1% to about 5%, from about 0.1% to about 4%, from about 0.1% to about 3%, from about 0.1% to about 2%, from about 0.1% to about 1%, or from about 0.1% to about 0.5% of the anhydro-subunits in at least one fraction (e.g., DP1, DP2 and/or DP3) of a herein described preparation are caramelization products. In some embodiments, from about 0.1% to about 5%, from about 0.1% to about 2%, or from about 0.1% to about 1% of the anhydro-subunits in at least one fraction (e.g., DP1, DP2 and/or DP3) of the preparation are caramelization products. In some embodiments, less than 50%, 40%, 30%, 25%, 20%, 15%, 14%, 13%, 12%, 11%, 10%, 9%, 8%, 7%, 6%, 5%, 4%, 3%, 2%, or 1% of the anhydro-subunits in at least one fraction of the preparation are caramelization products. In some embodiments, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the anhydro-subunits in the DP1, DP2, and/or DP3 fractions of a herein described oligosaccharide preparation are caramelization products.

In some embodiments, from about 0.01% to about 50%, from about 0.01% to about 40%, from about 0.01% to about 30%, from about 0.01% to about 20%, from about 0.01% to about 10%, from about 0.01% to about 5%, from about 0.01% to about 4%, from about 0.01% to about 3%, from about 0.01% to about 2%, from about 0.01% to about 1%, from about 0.01% to about 0.5%, from about 0.1% to about 50%, from about 0.1% to about 40%, from about 0.1% to about 30%, from about 0.1% to about 20%, from about 0.1% to about 10%, from about 0.1% to about 5%, from about 0.1% to about 4%, from about 0.1% to about 3%, from about 0.1% to about 2%, from about 0.1% to about 1%, or from about 0.1% to about 0.5% of the anhydro-subunits in each fraction of a herein described oligosaccharide preparation are caramelization products. In some embodiments, from about 0.1% to about 5%, from about 0.1% to about 2%, or from about 0.1% to about 1% of the anhydro-subunits in each fraction of the preparation are caramelization products. In some embodiments, less than 50%, less than 40%, less than 30%, less than 20%, less than 25%, less than 20%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the anhydro-subunits in each fraction of the preparation are caramelization products.

In some embodiments, each of the oligosaccharides in a herein described oligosaccharide preparation independently and optionally comprises an anhydro-subunit. In some embodiments, two or more independent oligosaccharides comprise the same or different anhydro-subunits. In some embodiments, two or more independent oligosaccharides comprise different anhydro-subunits. For example, in some embodiments, the oligosaccharide preparation comprise a DP1 anhydro-subunit containing oligosaccharide that comprises a 1,6-anhydro-β-D-glucopyranose and a DP2 anhydro-subunit containing oligosaccharide that comprises a 1,6-anhydro-β-D-glucofuranose subunit. In some embodiments, one or more oligosaccharides in the oligosaccharide preparation comprise two or more the same or different anhydro-subunits.

In some embodiments, in any fraction of the oligosaccharide preparation that has a degree of polymerization equal or greater than 2 (i.e., DP2 to DPn fractions), an anhydro-subunit may be linked to one or more regular or anhydro-subunits. In some embodiments, in the DP2 to DPn fractions, at least one anhydro-subunit is linked to one, two, or three other regular or anhydro-subunits. In some embodiments, in the DP2 to DPn fractions, at least one anhydro-subunit is linked to one or two regular subunits. In some embodiments, in the DP2 to DPn fractions, at least one anhydro-subunit is linked to one regular subunit. In some embodiments, in any of the DP2 to DPn fractions, more than 99%, 90%, 80%, 70%, 60%, 50%, 40%, or 30% of anhydro-subunits are linked to one regular subunit. In some embodiments, in each of the DP2 to DPn fraction, more than 99%, 90%, 80%, 70%, 60%, 50%, 40%, or 30% of anhydro-subunits are linked to one regular subunit.

In some embodiments, in any fraction of the oligosaccharide preparation that has a degree of polymerization equal or greater than 2 (i.e., DP2 to DPn fractions), an anhydro-subunit can be located at a chain-end of an oligosaccharide. In some embodiments, in any fraction of the oligosaccharide preparation that has a degree of polymerization equal or greater than 3 (i.e., DP3 to DPn fractions), an anhydro-subunit can be located at a position that is not a chain-end of an oligosaccharide. In some embodiments, in the DP2 to DPn fractions, at least one of the anhydro-subunits is located at the chain-end of an oligosaccharide. In some embodiments, greater than 99%, 95%, 90%, 85%, 80%, 75%, 70%, 65%, 60%, 55%, 50%, 45%, 40%, 35%, or 30% of the anhydro-subunits in the DP2 to DPn fractions are located at the chain-end of the oligosaccharides. In some embodiments, greater than 95%, 90%, 80%, 70%, 60%, 50%, 40%, 30%, 20%, or 10% of the anhydro-subunits in the oligosaccharide preparation are located at the chain-end of the oligosaccharides. In some embodiments, greater than 30%, 40%, 50%, 60%, 70%, 80%, 90%, 95%, or 99% of the anhydro-subunit containing oligosaccharides comprise a chain-end anhydro-subunit. In some embodiments, greater than 80%, 85%, 90%, 91%, 92%, 93%, 94%, 95%, 96%, 97%, 98%, or 99% of the anhydro-subunit containing oligosaccharides comprise a chain-end anhydro-subunit.

Glycosidic Linkages

In some embodiments, a herein described oligosaccharide preparation comprises a variety of glycosidic linkages. The type and distribution of the glycosidic linkages can depend on the source and manufacturing method of the oligosaccharide preparation. In some embodiments, the type and distribution of various glycosidic linkages can be determined and/or detected by any suitable methods known in the art such as NMR. For example, in some embodiments, the glycosidic linkages are determined and/or detected by $^1$H NMR, $^{13}$C NMR, 2D NMR such as 2D JRES, HSQC, HMBC, DOSY, COSY, ECOSY, TOCSY, NOESY, or ROESY, or any combination thereof. In some embodiments, the glycosidic linkages are determined and/or detected, at least in part, by $^1$H NMR. In some embodiments, the glycosidic linkages are determined and/or detected, at least in part, by $^{13}$C NMR. In some embodiments, the glycosidic linkages are determined and/or detected, at least in part, by 2D $^1$H, $^{13}$C-HSQC NMR.

In some embodiments, a herein described oligosaccharide preparation comprises one or more α-(1,2) glycosidic linkages, α-(1,3) glycosidic linkages, α-(1,4) glycosidic linkages, α-(1,6) glycosidic linkages, β-(1,2) glycosidic linkages, β-(1,3) glycosidic linkages, β-(1,4) glycosidic linkages, β-(1,6) glycosidic linkages, α-(1,1)-α glycosidic linkages, α-(1,1)-β glycosidic linkages, β-(1,1)-β glycosidic linkages, or any combination thereof.

In some embodiments, the oligosaccharide preparations have a glycosidic bond type distribution of from about 0 to about 60 mol %, from about 5% to about 55 mol %, from about 5% to about 50 mol %, from about 5% to about 45 mol %, from about 5% to about 40 mol %, from about 5% to about 35 mol %, from about 5% to about 30 mol %, from about 5% to about 25 mol %, from about 10% to about 60 mol %, from about 10% to about 55 mol %, from about 10% to about 50 mol %, from about 10% to about 45 mol %, from about 10% to about 40 mol %, from about 10% to about 35 mol %, from about 15% to about 60 mol %, from about 15% to about 55 mol %, from about 15% to about 50 mol %, from about 15% to about 45 mol %, from about 15% to about 40 mol %, from about 15% to about 35 mol %, from about 20% to about 60 mol %, from about 20% to about 55 mol %, from about 20% to about 50 mol %, from about 20% to about 45 mol %, from about 20% to about 40 mol %, from about 20% to about 35 mol %, from about 25% to about 60 mol %, from about 25% to about 55 mol %, from about 25% to about 50 mol %, from about 25% to about 45 mol %, from about 25% to about 40 mol %, or from about 25% to about 35 mol % of α-(1,6) glycosidic linkages.

In some embodiments, the oligosaccharide preparations have a glycosidic bond type distribution of from about 0 to about 50 mol %, from about 0 to about 40 mol %, from about 0 to about 35 mol %, from about 0 to about 30 mol %, from about 0 to about 25 mol %, from about 0 to about 20 mol %, from about 5% to about 40 mol %, from about 5% to about 35 mol %, from about 5% to about 30 mol %, from about 5% to about 25 mol %, from about 5% to about 20 mol %, from about 10% to about 40 mol %, from about 10% to about 35 mol %, from about 10% to about 20 mol %, from about 15% to about 40 mol %, from about 15% to about 35 mol %, from about 15% to about 30 mol %, from about 15% to about 25 mol %, or from about 15% to about 20 mol % of α-(1,3) glycosidic linkages.

In some embodiments, the oligosaccharide preparations have a glycosidic bond type distribution of from about 0 to about 40 mol %, from about 0 to about 35 mol %, from about 0 to about 30 mol %, from about 0 to about 25 mol %, from about 0 to about 20 mol %, from about 0 to about 15 mol %, from about 0 to about 10 mol %, from about 2% to about 30 mol %, from about 2% to about 25 mol %, from about 2% to about 20 mol %, from about 2% to about 15 mol %, from about 2% to about 10 mol %, from about 3% to about 30 mol %, from about 3% to about 25 mol %, from about 3% to about 20 mol %, from about 3% to about 15 mol %, from about 3% to about 10 mol %, from about 5% to about 30 mol %, from about 5% to about 25 mol %, from about 5% to about 20 mol %, from about 5% to about 15 mol %, or from about 5% to about 10 mol % of α-(1,2) glycosidic linkages.

In some embodiments, the oligosaccharide preparations have a glycosidic bond type distribution of from about 0 to about 40 mol %, from about 0 to about 30 mol %, from about 0 to about 25 mol %, from about 0 to about 20 mol %, from about 0 to about 15 mol %, from about 0 to about 10 mol %, or from about 0 to about 5 mol % of α-(1,4) glycosidic linkages. In some embodiments, the oligosaccharide preparations have a glycosidic bond type distribution of less than 40 mol %, less than 30 mol %, less than 20 mol %, less than 15 mol %, less than 10 mol %, less than 9 mol %, less than 8 mol %, less than 7 mol %, less than 6 mol %, less than 5 mol %, less than 4 mol %, less than 3 mol %, or less than 2 mol % of α-(1,4) glycosidic linkages.

In some embodiments, the oligosaccharide preparations have a glycosidic bond type distribution of from about 0 to about 40 mol %, from about 0 to about 35 mol %, from about 0 to about 30 mol %, from about 0 to about 25 mol %, from about 0 to about 20 mol %, from about 0 to about 15 mol %, from about 0 to about 10 mol %, from about 2% to about 30 mol %, from about 2% to about 25 mol %, from about 2% to about 20 mol %, from about 2% to about 15 mol %, from about 2% to about 10 mol %, from about 5% to about 30 mol %, from about 5% to about 25 mol %, from about 5% to about 20 mol %, from about 5% to about 15 mol %, from about 5% to about 10 mol %, from about 8% to about 30 mol %, from about 8% to about 25 mol %, from about 8% to about 20 mol %, from about 8% to about 15 mol %, or from about 10% to about 15 mol % of β-(1,6) glycosidic linkages.

In some embodiments, the oligosaccharide preparations have a glycosidic bond type distribution of from about 0 to about 40 mol %, from about 0 to about 35 mol %, from about 0 to about 30 mol %, from about 0 to about 25 mol %, from about 0 to about 20 mol %, from about 0 to about 15 mol %, from about 0 to about 10 mol %, from about 2% to about 30 mol %, from about 2% to about 25 mol %, from about 2% to about 20 mol %, from about 2% to about 15 mol %, from about 2% to about 10 mol %, from about 3% to about 30 mol %, from about 3% to about 25 mol %, from about 3% to about 20 mol %, from about 3% to about 15 mol %, from about 3% to about 10 mol %, from about 5% to about 30 mol %, from about 5% to about 25 mol %, from about 5% to about 20 mol %, from about 5% to about 15 mol %, or from about 5% to about 10 mol % of β-(1,4) glycosidic linkages.

In some embodiments, the oligosaccharide preparations have a glycosidic bond type distribution of from about 0 to about 40 mol %, from about 0 to about 30 mol %, from about 0 to about 25 mol %, from about 0 to about 20 mol %, from about 0 to about 15 mol %, from about 0 to about 10 mol %, from about 0 to about 5 mol %, from about 1% to about 20 mol %, from about 1% to about 15 mol %, from about 1% to about 10 mol %, from about 1% to about 5 mol %, from about 2% to about 20 mol %, from about 2% to about 15 mol %, from about 2% to about 10 mol %, or from about 2% to about 5 mol % of β-(1,2) glycosidic linkages. In some embodiments, the oligosaccharide preparations have a glycosidic bond type distribution of less than 40 mol %, less than 30 mol %, less than 20 mol %, less than 15 mol %, less than 10 mol %, less than 9 mol %, less than 8 mol %, less than 7 mol %, less than 6 mol %, less than 5 mol %, less than 4 mol %, less than 3 mol %, or less than 2 mol % of β-(1,2) glycosidic linkages.

In some embodiments, the oligosaccharide preparations have a glycosidic bond type distribution of from about 0 to about 40 mol %, from about 0 to about 30 mol %, from about 0 to about 25 mol %, from about 0 to about 20 mol %, from about 0 to about 15 mol %, from about 0 to about 10 mol %, from about 0 to about 5 mol %, from about 1% to about 20 mol %, from about 1% to about 15 mol %, from about 1% to about 10 mol %, from about 1% to about 5 mol %, from about 2% to about 20 mol %, from about 2% to about 15 mol %, from about 2% to about 10 mol %, or from about 2% to about 5 mol % of β-(1,3) glycosidic linkages. In some embodiments, the oligosaccharide preparations have a glycosidic bond type distribution of less than 40 mol %, less than 30 mol %, less than 20 mol %, less than 15 mol %, less than 10 mol %, less than 9 mol %, less than 8 mol %, less than 7 mol %, less than 6 mol %, less than 5 mol %, less than 4 mol %, less than 3 mol %, or less than 2 mol % of β-(1,3) glycosidic linkages.

In some embodiments, the oligosaccharide preparations have a glycosidic bond type distribution that is different from a glycosidic bond type distribution of non-synthetic oligosaccharide preparations. For example, in some embodiments, the oligosaccharide preparations have a glycosidic bond type distribution that is different from that of the base nutritional compositions. In some embodiments, the base nutritional compositions comprise a natural carbohydrate source, such as starch and plant fibers. Some of the natural carbohydrate sources have a high percentage of α-(1,4), α-(1,6), and/or β-(1,6) glycosidic linkages. Accordingly, in some embodiments, the oligosaccharide preparations have a lower percentage of α-(1,4) glycosidic linkages than the base nutritional composition. In some embodiments, the oligosaccharide preparations have a lower percentage of α-(1,6) glycosidic linkages than the base nutritional composition. In other embodiments, the oligosaccharide preparations have a higher percentage of α-(1,6) glycosidic linkages than the base nutritional composition. In some embodiments, the oligosaccharide preparations have a lower percentage of β-(1,6) glycosidic linkages than the base nutritional composition. In some embodiments, the oligosaccharide preparation comprises glycosidic linkages that are not readily digestible or hydrolysable by enzymes.

Specifically, in some embodiments, the α-(1,2), α-(1,3), α-(1,4), α-(1,6), β-(1,2), β-(1,3), β-(1,4), and/or β-(1,6) glycosidic linkages in the glycosidic bond type distribution of a herein described oligosaccharide preparations is at least 50 mol %, at least 40 mol %, at least 30 mol %, at least 20 mol %, at least 15 mol %, at least 10 mol %, at least 5 mol %, at least 2 mol %, or at least 1 mol % lower than that of the base nutritional composition. In some embodiments, the α-(1,2), α-(1,3), α-(1,4), α-(1,6), β-(1,2), β-(1,3), β-(1,4), and/or β-(1,6) glycosidic linkages in the glycosidic bond type distribution of the oligosaccharide preparations is at least 50 mol %, at least 40 mol %, at least 30 mol %, at least 20 mol %, at least 15 mol %, at least 10 mol %, at least 5 mol %, at least 2 mol %, or at least 1 mol % higher than that of the base nutritional composition.

It should be understood by one of skill in the art that certain types of glycosidic linkages may not be applicable to oligosaccharides comprising certain type of monosaccharides. For example, in some embodiments, the oligosaccharide preparation comprises α-(1,2) glycosidic linkages and α-(1,6) glycosidic linkages. In other embodiments, the oligosaccharide preparation comprises α-(1,2) glycosidic linkages and β-(1,3) glycosidic linkages. In some embodiments, the oligosaccharide preparation comprises α-(1,2) glycosidic linkages, α-(1,3) glycosidic linkages, and β-(1,6) glycosidic linkages. In some embodiments, the oligosaccharide preparation comprises α-(1,2) glycosidic linkages, α-(1,3) glycosidic linkages, α-(1,4) glycosidic linkages, α-(1,6) glycosidic linkages, β-(1,2) glycosidic linkages, β-(1,3) glycosidic linkages, β-(1,4) glycosidic linkages, and β-(1,6) glycosidic linkages.

Molecular Weight

The molecular weight and molecular weight distribution of the herein described oligosaccharide preparations can be determined by any suitable analytical means and instrumentation, such as end group method, osmotic pressure (osmometry), ultracentrifugation, viscosity measurements, light scattering method, SEC, SEC-MALLS, FFF, A4F, HPLC, and mass spectrometry. In some embodiments, the molecular weight and molecular weight distribution are determined by mass spectrometry, such as MALDI-MS, LC-MS, or GC-MS. In some embodiments, the molecular weight and molecular weight distribution are determined by size exclusion chromatography (SEC), such as gel permeation chromatography (GPC). In other embodiments, the molecular weight and molecular weight distribution are determined by HPLC. In some embodiments, the molecular weight and molecular weight distribution are determined by MALDI-MS.

In some embodiments, a herein described oligosaccharide preparation has a weight average molecular weight of from about 100 to about 10000 g/mol, from about 200 to about 8000 g/mol, from about 300 to about 5000 g/mol, from about 500 to about 5000 g/mol, from about 700 to about 5000 g/mol, from about 900 to about 5000 g/mol, from about 1100 to about 5000 g/mol, from about 1300 to about 5000 g/mol, from about 1500 to about 5000 g/mol, from about 1700 to about 5000 g/mol, from about 300 to about 4500 g/mol, from about 500 to about 4500 g/mol, from about 700 to about 4500 g/mol, from about 900 to about 4500 g/mol, from about 1100 to about 4500 g/mol, from about 1300 to about 4500 g/mol, from about 1500 to about 4500 g/mol, from about 1700 to about 4500 g/mol, from about 1900 to about 4500 g/mol, from about 300 to about 4000 g/mol, from about 500 to about 4000 g/mol, from about 700 to about 4000 g/mol, from about 900 to about 4000 g/mol, from about 1100 to about 4000 g/mol, from about 1300 to about 4000 g/mol, from about 1500 to about 4000 g/mol, from about 1700 to about 4000 g/mol, from about 1900 to about 4000 g/mol, from about 300 to about 3000 g/mol, from about 500 to about 3000 g/mol, from about 700 to about 3000 g/mol, from about 900 to about 3000 g/mol, from about 1100 to about 3000 g/mol, from about 1300 to about 3000 g/mol, from about 1500 to about 3000 g/mol, from about 1700 to about 3000 g/mol, from about 1900 to about 3000 g/mol, from about 2100 to about 3000 g/mol, from about 300 to about 2500 g/mol, from about 500 to about 2500 g/mol, from about 700 to about 2500 g/mol, from about 900 to about 2500 g/mol, from about 1100 to about 2500 g/mol, from about 1300 to about 2500 g/mol, from about 1500 to about 2500 g/mol, from about 1700 to about 2500 g/mol, from about 1900 to about 2500 g/mol, from about 2100 to about 2500 g/mol, from about 300 to about 1500 g/mol, from about 500 to about 1500 g/mol, from about 700 to about 1500 g/mol, from about 900 to about 1500 g/mol, from about 1100 to about 1500 g/mol, from about 1300 to about 1500 g/mol, from about 2000 to about 2800 g/mol, from about 2100 to about 2700 g/mol, from about 2200 to about 2600 g/mol, from about 2300 to about 2500 g/mol, or from about 2320 to about 2420 g/mol. In some embodiments, the weight average molecular weight of the oligosaccharide preparation is from about 2000 to about 2800 g/mol, from about 2100 to about 2700 g/mol, from about 2200 to about 2600 g/mol, from about 2300 to about 2500 g/mol, or from about 2320 to about 2420 g/mol. In some embodiments, the oligosaccharide preparation has a weight average molecular weight in a range from at least 500 g/mol, 750 g/mol, 1000 g/mol, or 1500 g/mol to at most 1750 g/mol, 2000 g/mol, 2250 g/mol, 2500 g/mol, or 3000 g/mol. In some embodiments, the weight average molecular weight of a herein described oligosaccharide preparation is determined by HPLC according to Example 9.

In some embodiments, a herein described oligosaccharide preparation has a number average molecular weight of from about 100 to about 10000 g/mol, from about 200 to about 8000 g/mol, from about 300 to about 5000 g/mol, from about 500 to about 5000 g/mol, from about 700 to about 5000 g/mol, from about 900 to about 5000 g/mol, from about 1100 to about 5000 g/mol, from about 1300 to about 5000 g/mol, from about 1500 to about 5000 g/mol, from about 1700 to about 5000 g/mol, from about 300 to about 4500 g/mol, from about 500 to about 4500 g/mol, from about 700 to about 4500 g/mol, from about 900 to about 4500 g/mol, from about 1100 to about 4500 g/mol, from about 1300 to about 4500 g/mol, from about 1500 to about 4500 g/mol, from about 1700 to about 4500 g/mol, from about 1900 to about 4500 g/mol, from about 300 to about 4000 g/mol, from about 500 to about 4000 g/mol, from about 700 to about 4000 g/mol, from about 900 to about 4000 g/mol, from about 1100 to about 4000 g/mol, from about 1300 to about 4000 g/mol, from about 1500 to about 4000 g/mol, from about 1700 to about 4000 g/mol, from about 1900 to about 4000 g/mol, from about 300 to about 3000 g/mol, from about 500 to about 3000 g/mol, from about 700 to about 3000 g/mol, from about 900 to about 3000 g/mol, from about 1100 to about 3000 g/mol, from about 1300 to about 3000 g/mol, from about 1500 to about 3000 g/mol, from about 1700 to about 3000 g/mol, from about 1900 to about 3000 g/mol, from about 2100 to about 3000 g/mol, from about 300 to about 2500 g/mol, from about 500 to about 2500 g/mol, from about 700 to about 2500 g/mol, from about 900 to about 2500 g/mol, from about 1100 to about 2500 g/mol, from about 1300 to about 2500 g/mol, from about 1500 to about 2500 g/mol, from about 1700 to about 2500 g/mol, from about 1900 to about 2500 g/mol, from about 2100 to about 2500 g/mol, from about 300 to about 2000 g/mol, from about 500 to about 2000 g/mol, from about 700 to about 2000 g/mol, from about 900 to about 2000 g/mol, from about 1100 to about 2000 g/mol, from about 300 to about 1500 g/mol, from about 500 to about 1500 g/mol, from about 700 to about 1500 g/mol, from about 900 to about 1500 g/mol, from about 1100 to about 1500 g/mol, from about 1300 to about 1500 g/mol, from about 1000 to about 2000 g/mol, from about 1100 to about 1900 g/mol, from about 1200 to about 1800 g/mol, from about 1300 to about 1700 g/mol, from about 1400 to about 1600 g/mol, or from about 1450 to about 1550 g/mol. In some embodiments, the number average molecular weight of the oligosaccharide preparation is from about 1000 to about 2000 g/mol, from about 1100 to about 1900 g/mol, from about 1200 to about 1800 g/mol, from about 1300 to about 1700 g/mol, 1400 to 1600 g/mol, or 1450-1550 g/mol. In some embodiments, the oligosaccharide preparation has a number average molecular weight in a range from at least 500 g/mol, 750 g/mol, 1000 g/mol, or 1500 g/mol to at most 1750 g/mol, 2000 g/mol, 2250 g/mol, 2500 g/mol, or 3000 g/mol. In some embodiments, the number average molecular weight of a herein described oligosaccharide preparation is determined by HPLC according to Example 9.

Types of Oligosaccharides

The species of oligosaccharides present in an oligosaccharide preparation can depend on the type of the one or more feed sugars. For example, in some embodiments, the oligosaccharide preparations comprise a gluco-oligosaccharide when the feed sugars comprise glucose. For example, in some embodiments, the oligosaccharide preparations comprise a galacto-oligosaccharide when the feed sugars comprise galactose. For another example, in some embodiments, the oligosaccharide preparations comprise gluco-galacto-oligosaccharides when the feed sugars comprise galactose and glucose.

In some embodiments, a herein described oligosaccharide preparation comprises one or more species of monosaccharide subunits. In some embodiments, the oligosaccharide preparation comprises oligosaccharides with 1, 2, 3, 4, 5, 6, 7, 8, 9, 10, 11, 12, 13, 14, 15, 16, 17, 18, 19, 20, or more different species of monosaccharides subunits.

In some embodiments, the oligosaccharide preparation comprises oligosaccharides with 1, 2, 3, or 4 different species of monosaccharides subunits. In some embodiments, the oligosaccharide preparation comprises oligosaccharides with 1, 2, or 3 different species of monosaccharides subunits. In some embodiments, the oligosaccharide preparation comprises oligosaccharides with 3 different species of monosaccharides subunits. In some embodiments, the oligosaccharide preparation comprises oligosaccharides with 2 different species of monosaccharides subunits. In some embodiments, the oligosaccharide preparation comprises one species of monosaccharides subunits.

In some embodiments, the oligosaccharide preparation comprises different species of oligosaccharides that each oligosaccharide molecule independently comprises 1, 2, 3, 4, 5, 6, 7, 8, 9, or 10 different species of monosaccharides subunits. In some embodiments, a herein described oligosaccharide preparation comprises $10^2$, $10^3$, $10^4$, $10^5$, or more different species of oligosaccharides. In some embodiments, some of the oligosaccharides in the preparation comprise one species of monosaccharide subunits and some other oligosaccharides in the same preparation comprise two or more species of monosaccharides subunits. For instance, in some embodiments, when the feed sugars are glucose and galactose, the oligosaccharide preparation can comprise oligosaccharides that comprise only glucose subunits, oligosaccharides that comprise only galactose subunits, oligosaccharides that comprise both glucose and galactose subunits at various ratios, or any combination thereof.

In some embodiments, any or all of the n fractions of the oligosaccharide preparation comprises different species of oligosaccharides subunits that each oligosaccharide independently comprises 1, 2, 3, 4, 5, 6, 7, 8, 9, or 10 different species of monosaccharides subunits. In some embodiments, some of the oligosaccharides in a fraction of the preparation comprise one species of monosaccharide subunits and some other oligosaccharides in the same fraction of the preparation comprise two or more species of monosaccharides subunits.

In some embodiments, a herein described oligosaccharide preparation comprises one or more monosaccharide subunits selected from a group consisting of: triose, tetrose, pentose, hexose, heptose, and any combination thereof, wherein each of the said triose, tetrose, pentose, hexose, or heptose subunit is independently and optionally functionalized and/or replaced with one of its corresponding anhydro-subunits. In some embodiments, the corresponding anhydro-subunit is a product of thermal dehydration of the monosaccharide subunit. In some embodiments, the corresponding anhydro-subunit is a caramelization product of the monosaccharide subunit.

In some embodiments, a herein described oligosaccharide preparation comprises pentose subunits, hexose subunits, or any combination thereof, wherein each of the said pentose or hexose subunit is independently and optionally functionalized and/or replaced with one of its corresponding anhydro-subunits. In some embodiments, the oligosaccharide preparation comprises hexose subunits, wherein each of the said hexose subunits is independently and optionally replaced with one of its corresponding anhydro-subunits.

As used herein, a tetrose refers to a monosaccharide with four carbon atoms, such as erythrose, threose, and erythrulose. As used herein, a pentose refers to a monosaccharide with five carbon atoms, such as arabinose, lyxose, ribose, and xylose. As used herein, a hexose refers to a monosaccharide with six carbon atoms, such as allose, altrose, glucose, mannose, gulose, idose, galactose, talose, psicose, fructose, sorbose, and tagatose. As used herein, a heptose refers to a monosaccharide with seven carbon atoms, such as sedoheptulose and mannoheptulose.

In some embodiments, a herein described oligosaccharide preparation comprises glucose subunit, wherein at least one glucose subunit is optionally replaced with an anhydro-glucose subunit. In some embodiments, a herein described oligosaccharide preparation comprises galactose subunit, wherein at least one galactose subunit is optionally replaced with anhydro-galactose subunit. In some embodiments, a herein described oligosaccharide preparation comprises galactose and glucose subunits, wherein at least one galactose subunit or at least one glucose subunit is optionally replaced with one of its corresponding anhydro-subunits. In some embodiments, a herein described oligosaccharide preparation comprises fructose and glucose subunits, wherein at least one fructose subunit or at least one glucose subunit is optionally replaced with one of its corresponding anhydro-subunits. In some embodiments, a herein described oligosaccharide preparation comprises mannose and glucose subunit, wherein at least one mannose subunit or at least one glucose subunit is optionally replaced with one of its corresponding anhydro-subunits.

In some embodiments, a herein described oligosaccharide preparation comprises a gluco-galactose-oligosaccharide preparation, a gluco-oligosaccharide preparation, a galacto-oligosaccharide preparation, a fructo-oligosaccharide preparation, a manno-oligosaccharide preparation, an arabino-oligosaccharide preparation, a xylo-oligosaccharide preparation, a gluco-fructo-oligosaccharide preparation, a gluco-manno-oligosaccharide preparation, a gluco-arabino-oligosaccharide preparation, a gluco-xylo-oligosaccharide preparation, a galacto-fructo-oligosaccharide preparation, a galacto-manno-oligosaccharide preparation, a galacto-arabino-oligosaccharide preparation, a galacto-xylo-oligosaccharide preparation, a fructo-manno-oligosaccharide preparation, a fructo-arabino-oligosaccharide preparation, a fructo-xylo-oligosaccharide preparation, a manno-arabino-oligosaccharide preparation, a manno-xylo-oligosaccharide preparation, an arabino-xylo-oligosaccharide preparation, a galacto-arabino-xylo-oligosaccharide preparation, a fructo-galacto-xylo-oligosaccharide preparation, an arabino-fructo-manno-xylo-oligosaccharide preparation, a gluco-fructo-galacto-arabino-oligosaccharide preparation, a fructo-gluco-arabino-manno-xylo oligosaccharide preparation, a gluco-galacto-fructo-manno-arabinoxylo-oligosaccharide preparation, or any combinations thereof; wherein each of the monosaccharide subunit within the preparation is independently and optionally functionalized and/or replaced with one of its corresponding anhydro-subunits.

In certain embodiments, a herein described oligosaccharide preparation comprises more than 99% of glucose subunits by weight. In some embodiments, the oligosaccharide preparation comprises only glucose subunits.

In some embodiments, a herein described oligosaccharide preparation comprises about 45% to 55% of glucose subunits and about 55% to 45% of galactose subunits by weight. In some specific embodiments, the oligosaccharide preparation comprises about 50% glucose and 50% galactose subunits by weight.

In some embodiments, a herein described oligosaccharide preparation comprises about 80% to 95% of glucose subunits and about 20% to 5% of mannose subunits by weight. In some embodiments, the oligosaccharide preparation comprises about 85% to 90% of glucose subunits and about 15% to 10% of mannose subunits by weight.

In some embodiments, a herein described oligosaccharide preparation comprises about 80% to 95% of glucose subunits and about 20% to 5% of galactose subunits by weight. In some embodiments, the oligosaccharide preparation comprises about 85% to 90% of glucose subunits and about 15% to 10% of galactose subunits by weight.

In some embodiments, a herein described oligosaccharide preparation comprises about 80% to 95% of glucose subunits, 0% to 8% of galactose subunits, and 5% to 20% of mannose subunits by weight. In some embodiments, the oligosaccharide preparation comprises about 80% to 90% of glucose subunits, 1% to 5% of galactose subunits, and 10% to 15% of mannose subunits by weight.

In some embodiments, an oligosaccharide preparation described herein comprises from about 1 wt % to about 100 wt %, from about 50 wt % to about 100 wt %, from about 80 wt % to about 98 wt %, or from about 85 wt % to about 95 wt % of glucose subunits, or any ranges therebetween. In some embodiments, galactose subunits are present in an oligosaccharide preparation described herein at an amount of from about 0 wt % to about 90 wt %, from about 1 wt % to about 50 wt %, from about 2 wt % to about 20 wt %, or from about 5 wt % to about 15 wt %, or any ranges therebetween. In some embodiments, mannose subunits are present in an oligosaccharide preparation described herein at an amount of from about 0 wt % to about 90 wt %, from about 1 wt % to about 50 wt %, from about 2 wt % to about 20 wt %, or from about 5 wt % to about 15 wt %, or any ranges therebetween.

In some embodiments, a herein described oligosaccharide preparation has a composition of monosaccharide subunits as shown in Table 1.

TABLE 1

Exemplary Compositions of Oligosaccharide Preparations

| Oligo Composition No. | Glucose and anhydro-glucose subunits (wt %) | Galactose and anhydro-galactose subunits (wt %) | Mannose and anhydro-mannose subunits (wt %) | Fructose and anhydro-fructose subunits (wt %) |
|---|---|---|---|---|
| 1 | 87.5 | 12.5 | 0 | 0 |
| 2 | 100 | 0 | 0 | 0 |
| 3 | 85 | 2.5 | 12.5 | 0 |
| 4 | 87.5 | 0 | 12.5 | 0 |
| 5 | 50 | 50 | 0 | 0 |
| 6 | 75 | 0 | 25 | 0 |
| 7 | 9 | 6 | 0 | 0 |
| 8 | 90 | 0 | 10 | 0 |
| 9 | 95 | 5 | 0 | 0 |
| 10 | 97.5 | 2.5 | 0 | 0 |
| 11 | 85 | 5 | 10 | 0 |
| 12 | 85 | 1.5 | 13.5 | 0 |
| 13 | 80 | 10 | 10 | 0 |
| 14 | 85 | 0 | 15 | 0 |
| 15 | 85 | 15 | 0 | 0 |
| 16 | 87.5 | 0 | 0 | 12.5 |

D- Vs. L-Form

In some embodiments, at least one monosaccharide subunit in an oligosaccharide is in L-form. In some embodiments, at least one monosaccharides subunit in an oligosaccharide is in D-form. In some embodiments, the monosaccharide subunits in a herein described oligosaccharide preparation are in their naturally-abundant form, for example, D-glucose, D-xylose, and L-arabinose.

In some embodiments, a herein described oligosaccharide preparation comprises a mixture of L- and D-forms of monosaccharide subunits. In some embodiments, the ratio of monosaccharide subunits in L- to D- or in D- to L-form is about 1:1, about 1:2, about 1:3, about 1:4, about 1:5, about 1:6, about 1:7, about 1:8, about 1:9, about 1:10, about 1:12, about 1:14, about 1:16, about 1:18, about 1:20, about 1:25, about 1:30, about 1:35, about 1:40, about 1:45, about 1:50, about 1:55, about 1:60, about 1:65, about 1:70, about 1:75, about 1:80, about 1:85, about 1:90, about 1:100 or about 1:150.

Functionalized Oligosaccharides

In some embodiments, one or more oligosaccharides in a herein described oligosaccharide preparation are independently functionalized. Functionalized oligosaccharides can be produced by, for example, combining one or more sugars with one or more functionalizing compounds in the presence of a catalyst. Methods of producing functionalized oligosaccharides are described in WO 2012/118767, WO 2014/031956, and WO/2016/122887, which are hereby incorporated by reference in their entirety and for their disclosure.

In some embodiments, the functionalizing compound comprises one or more acid groups (e.g., —COOH), hydroxyl groups, or N-containing groups (e.g., —CN, —NO$_2$, and —N(R$_a$)$_2$, wherein R$_a$ is hydrogen, alkyl, alkenyl, alkynyl, haloalkyl, heteroalkyl, cycloalkyl, aryl, heterocycloalkyl, or heteroaryl groups), S-containing groups (e.g., thiol and sulfates), halides (e.g., —Cl), P-containing groups (e.g., phosphate), or any combination thereof. In some embodiments, the functionalizing compound is linked to at least one monosaccharide subunit via an ether, ester, oxygen-sulfur, amine, or oxygen-phosphorous bond. In some embodiments, one or more functionalizing compounds are linked to a monosaccharide subunit via a single linkage. In some embodiments, at least one functionalizing compound is linked to one or two oligosaccharides via two or more linkages.

It is to be understood that for each oligosaccharide in the oligosaccharide preparation, each of the described embodiments is independent and can be combined as if each and every combination were listed separately; thus, any combination of the embodiments are encompassed by the present disclosure. For instance, the various embodiments can be grouped into several categories that include but are not limited to (i) the presence or absence of anhydro-subunit; (ii) the number and level of anhydro-subunit, (iii) the type of species of anhydro-subunit, (iv) the location of anhydro-subunit, (v) the degree of polymerization, (vi) the molecular weight, (vii) the presence or absence of any functional groups, (viii) the type of the oligosaccharide, (ix) the type of glycosidic linkage, and (x) the L-versus D-form. Accordingly, the described oligosaccharide preparation comprises a plurality of oligosaccharides of different species. In some embodiments, a herein described oligosaccharide preparation comprises at least 10, $10^2$, $10^3$, $10^4$, $10^5$, $10^6$, $10^7$, $10^8$, $10^9$, or $10^{10}$ different oligosaccharide species. In some embodiments, the preparation comprises at least $10^3$, $10^4$, $10^5$, $10^6$, or $10^9$ different oligosaccharide species. In some embodiments, the preparation comprises at least $10^3$ different oligosaccharide species.

III. Methods of Manufacturing Oligosaccharide Preparations

In one aspect, provided herein are methods of manufacturing oligosaccharide preparations. In some embodiments, provided herein are methods of manufacturing oligosaccharide preparations suitable for use in a nutritional composition, such as an animal feed composition, or being fed directly to an animal. In one aspect, provided herein are methods of manufacturing an oligosaccharide preparation, the method comprising heating an aqueous composition comprising one or more feed sugars and a catalyst to a temperature and for a time sufficient to induce polymerization, wherein the catalyst is selected from the group consisting of: (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid, 3-(1-pyridinio)-1-propanesulfonate; 2-(2-pyridinyl)ethanesulfonic acid; 3-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; poly(styrene sulfonic acid-co-divinylbenzene); lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan, and wherein the oligosaccharide preparation comprises at least n fractions of oligosaccharides each having a distinct degree of polymerization selected from 1 (DP1 fraction) to n (DPn fraction), wherein n is an integer greater than or equal to 2. In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, the polymerization of the feed sugars is achieved by a step-growth polymerization. In some embodiments, the polymerization of the feed sugars is achieved by poly condensation.

Feed Sugar

In some embodiments, a method of manufacturing oligosaccharide preparations described herein comprises heating one or more types of feed sugars. In some embodiments, the one or more types of feed sugars comprise monosaccharides, disaccharides, trisaccharides, tetrasaccharides, or any mixtures thereof.

In some embodiments, the one or more feed sugars comprise glucose. In some embodiments, the one or more feed sugars comprise glucose and galactose. In some embodiments, the one or more feed sugars comprise glucose, xylose, and galactose. In some embodiments, the one or more feed sugars comprise glucose and mannose. In some embodiments, the one or more feed sugars comprise glucose and fructose. In some embodiments, the one or more feed sugars comprise glucose, fructose, and galactose. In some embodiments, the one or more feed sugars comprise glucose, galactose, and mannose.

In some embodiments, the one or more feed sugars comprise disaccharides such as lactose, sucrose and cellobiose. In some embodiments, the one or more feed sugars comprise trisaccharides, such as maltotriose or raffinose. In certain embodiments, the one or more feed sugar comprise glucose, mannose, galactose, xylose, malto-dextrin, arabinose, or any combinations thereof. In certain embodiments, the one or more feed sugars comprise sugar syrup such as corn syrup. In some embodiments, the one or more feed sugars comprise glucose and lactose. In some embodiments, the one or more feed sugars comprise glucose and sucrose.

In some embodiments, the type of feed sugars can impact the resulting manufactured oligosaccharide preparations. For example, in some variations where the one or more feed sugars are all glucose, the resulting oligosaccharide preparations comprise gluco-oligosaccharides preparations. In other embodiments, where the one or more feed sugars are all mannose, the resulting oligosaccharide preparations comprise manno-oligosaccharide preparations. In some embodiments, wherein the one or more feed sugars comprise glucose and galactose, the resulting oligosaccharide preparations comprise gluco-galacto-oligosaccharide preparations. In yet other embodiments, where the one or more feed sugars comprise xylose, glucose and galactose, the resulting oligosaccharide preparations comprise gluco-galacto-xylo-oligosaccharide preparations.

In some embodiments, each of the one or more feed sugars can be independently in its de-hydrate or hydrate form. In some embodiments, the one or more feed sugars comprise glucose, galactose, fructose, mannose, or any combination thereof, and wherein each of the glucose, galactose, fructose, or mannose is independently in its mono-hydrate or de-hydrate form. In some embodiments, the one or more feed sugars comprise a monosaccharide mono-hydrate such as glucose monohydrate. In some embodiments, the one or more feed sugars comprise a saccharide di-hydrate such as trehalose di-hydrate. In some embodiments, the one or more feed sugars comprise at least one sugar in its de-hydrate form and at least one sugar in its hydrate form.

In some embodiments, the one or more feed sugars can be provided as a sugar solution, in which the sugars are combined with water and fed into the reactor. In some embodiments, the sugars can be fed into the reactor in a solid form and combined with water in the reactor. In some embodiments, the one or more feed sugars are combined and mixed before the addition of water. In other embodiments, the one or more feed sugars are combined into water and mixed thereafter.

In some embodiments, the method comprises combining two or more feed sugars with the catalyst to produce an oligosaccharide preparation. In some embodiments, the two or more feed sugars comprise from glucose, galactose, fructose, mannose, lactose, or any combination thereof. In some embodiments, the method comprises combining a mixture of sugars (e.g., monosaccharides, disaccharides, and/or trisaccharides) with the catalyst to produce an oligosaccharide preparation. In other embodiments, the method comprises combining a mixture of sugars and sugar alcohols with the catalyst to produce an oligosaccharide preparation.

In some embodiments, the one or more feed sugars comprise functionalized or modified sugars. Functionalized or modified sugars may comprise amino sugars, sugar acids, sugar alcohols, sugar amides, sugar ethers, or any combination thereof. In some embodiments, amino sugars refer to sugar molecules in which a hydroxyl group is replaced with an amine group. Exemplary amino sugars include, but are not limited to, N-Acetyl-d-glucosamine, mannosamine, neuraminic acid, muramic acid, N-acetyl-neuramin, N-acetyl-muramic, N-acetyl-galactosamine, N-acetyl-mannosa, N-glycolylneuram, acarviosin, D-glucosamine, and D-galactosamine.

In embodiments, sugar acids refer to sugars with a carboxyl group. Exemplary sugar acids include, but are not limited to, aldonic acids (such as glyceric acid, xylonic acid, gluconic acid, and ascorbic acid), ulosonic acids (such as neuraminic acid and ketodeoxyoctulosonic acid), uronic acids (such as glucuronic acid, galacturonic acid, and iduronic acid), and aldaric acids (such as tartaric acid, mucic acid, and saccharic acid).

In some embodiments, sugar alcohols refer to sugar-derived polyols. Exemplary sugar alcohols include, but are not limited to, ethylene glycol, arabitol, glycerol, erythritol, threitol, xylitol, ribitol, mannitol, sorbitol, galactitol, fucitol, iditol, inositol, and volemitol.

In some embodiments, sugar amides refer to sugar molecules that contain a —C(=O)—N— group. In embodiments, sugar ethers refer to sugar molecules that contain an ether bond, such as glucosides.

In some embodiments, the functionalized or modified sugars comprise glucosamine, N-acetylglucosamine, glucuronic acid, galacturonic acid, glucitol, xylitol, mannitol, sorbitol. In some embodiments, the one of more feed sugars comprise deoxysugars, such as fucose, rhamnose, deoxyribose, or fuculose.

In some embodiments, a herein described method of manufacturing oligosaccharide preparation is performed at gram scale. In some embodiments, a herein described method of manufacturing oligosaccharide preparation is performed at kilogram or higher scale. Accordingly, in some embodiments, the method comprises heating an aqueous composition comprising one or more feed sugars at a quantity of more than 0.5, more than 1, more than 2, more than 3, more than 4, more than 5, more than 6, more than 7, more than 9, more than 10, more than 100, or more than 1000 kg. In some embodiments, the method comprises heating an aqueous composition comprising one or more feed sugars at a quantity of no more than 0.5, 1, 2, 3, 4, 5, 6, 7, 9, 10, 100, 1000, or 1500 kg. In some embodiments, the method comprises heating an aqueous composition comprising one or more feed sugars at a quantity of more than 1 kg.

Catalyst

In some embodiments, a herein described method of manufacturing oligosaccharide preparation comprises the addition of one or more catalysts. In some embodiments, the catalyst provided herein comprises one or more acids. In some embodiments, the catalyst provided herein comprises mineral acid, carboxylic acid; amino acid; sulfonic acid; boronic acid; phosphonic acid; phosphinic acid; sulfuric acid; phosphoric acid; poly(styrene sulfonic acid-co-vinyl-benzyl-imidazolium sulfate-co-divinylbenzene); poly(styrene sulfonic acid-co-divinylbenzene); (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid; 3-(1-pyridinio)-1-propanesulfonate; 2-(2-pyridinyl)ethanesulfonic acid; 3-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; acetic acid; propionic acid; butanoic acid; glutamic acid; lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan; polymeric acid; carbon-supported acid; or any combination thereof.

In some embodiments, the catalyst provided herein comprises: (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid, 3-(1-pyridinio)-1-propane sulfonate; 2-(2-pyridinyl)ethanesulfonic acid; 3-(2-pyridyl)-5,6-diphenyl-1,2,4-triazine-p,p'-disulfonic acid monosodium salt hydrate; 1,1'-binaphthyl-2,2'-diyl-hydrogenphosphate; bis(4-methoxyphenyl)phosphinic acid; phenyl(3,5-xylyl)phosphinic acid; L-cysteic acid monohydrate; poly(styrene sulfonic acid-co-divinylbenzene); lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; Tryptophan; or any combination thereof.

In some embodiments, the catalyst provided herein is (+)-camphor-10-sulfonic acid. In some embodiments, the catalyst provided herein is 2-pyridinesulfonic acid. In some embodiments, the catalyst provided herein is 3-pyridinesulfonic acid. In some embodiments, the catalyst provided herein is 8-hydroxy-5-quinolinesulfonic acid hydrate. In some embodiments, the catalyst provided herein is α-hydroxy-2-pyridinemethanesulfonic acid. In some embodiments, the catalyst provided herein is (β)-camphor-10-sulfonic acid. In some embodiments, the catalyst provided herein is butylphosphonic acid. In some embodiments, the catalyst provided herein is diphenylphosphinic acid. In some embodiments, the catalyst provided herein is hexylphosphonic acid. In some embodiments, the catalyst provided herein is methylphosphonic acid. In some embodiments, the catalyst provided herein is phenylphosphinic acid. In some embodiments, the catalyst provided herein is phenylphosphonic acid. In some embodiments, the catalyst provided herein is tert-butylphosphonic acid. In some embodiments, the catalyst provided herein is SS)-VAPOL hydrogenphosphate. In some embodiments, the catalyst provided herein is 6-quinolinesulfonic acid. In some embodiments, the catalyst provided herein is 3-(1-pyridinio)-1-propanesulfonate. In some embodiments, the catalyst provided herein is 2-(2-pyridinyl)ethanesulfonic acid. In some embodiments, the catalyst provided herein is 3-(2-pyridyl)-5,6-diphenyl-1,2,4-triazine-p,p'-disulfonic acid monosodium salt hydrate. In some embodiments, the catalyst provided herein is 1,1'-binaphthyl-2,2'-diyl-hydrogenphosphate. In some embodiments, the catalyst provided herein is bis(4-methoxyphenyl) phosphinic acid. In some embodiments, the catalyst provided herein is phenyl(3,5-xylyl)phosphinic acid. In some embodiments, the catalyst provided herein is L-cysteic acid monohydrate. In some embodiments, the catalyst provided herein is poly(styrene sulfonic acid-co-divinylbenzene). In some embodiments, the catalyst provided herein is lysine.

In some embodiments, the catalyst is Ethanedisulfonic acid. In some embodiments, the catalyst is Ethanesulfonic acid. In some embodiments, the catalyst is Isethionic acid. In some embodiments, the catalyst is Homocysteic acid. In some embodiments, the catalyst is HEPBS (N-(2-Hydroxyethyl)piperazine-N'-(4-butanesulfonic acid)). In some embodiments, the catalyst is HEPES (4-(2-hydroxyethyl)-1-piperazineethanesulfonic acid). In some embodiments, the catalyst is 2-Hydroxy-3-morpholinopropanesulfonic acid. In some embodiments, the catalyst is 2-(N-morpholino) ethanesulfonic acid. In some embodiments, the catalyst is Methanesulfonic acid. In embodiments, the catalyst is Naphthalene-1-sulfonic acid. In some embodiments, the catalyst is some embodiments, the catalyst is Methaniazide. In some Naphthalene-2-sulfonic acid. In some embodiments, the catalyst is Perfluorobutanesulfonic acid. In some embodiments, the catalyst is 6-sulfoquinovose. In some embodiments, the catalyst is Triflic acid. In some embodiments, the catalyst is 2-aminoethanesulfonic acid. In some embodiments, the catalyst is Benzoic acid. In some embodiments, the catalyst is Chloroacetic acid. In some embodiments, the catalyst is Trifluoroacetic acid. In some embodiments, the catalyst is Caproic acid. In some embodiments, the catalyst is Enanthic acid. In some embodiments, the catalyst is Caprylic acid. In some embodiments, the catalyst is Pelargonic acid. In some embodiments, the catalyst is Lauric acid. In some embodiments, the catalyst is Pamitic acid. In some embodiments, the catalyst is Stearic acid. In some embodiments, the catalyst is Arachidic acid. In some embodiments, the catalyst is Aspartic acid. In some embodiments, the catalyst is Glutamic acid. In some embodiments, the catalyst is Serine. In some embodiments, the catalyst is Threonine. In some embodiments, the catalyst is Glutamine. In some embodiments, the catalyst is Cysteine. In some embodiments, the catalyst is Glycine. In some embodiments, the catalyst is Proline. In some embodiments, the catalyst is Alanine. In some embodiments, the catalyst is Valine. In some embodiments, the catalyst is Isoleucine. In some embodiments, the catalyst is Leucine. In some embodiments, the catalyst is Methionine. In some embodiments, the catalyst is Phenylalanine. In some embodiments, the catalyst is Tyrosine. In some embodiments, the catalyst is Tryptophan. In some embodiments, the catalyst provided herein is a polymeric catalyst or a carbon-supported catalyst disclosed in WO 2016122887, which is hereby incorporated by reference in its entirety and for its disclosure.

In some embodiments, the catalyst provided herein is present in an amount of from about 0.01% to about 5%, from about 0.02% to about 4%, from about 0.03% to about 3%, or from about 0.05% to about 2% of the one or more feed sugars by dry weight. In some embodiments, the catalyst provided herein is present in an amount of from about 1% to 2% of the one or more feed sugars by dry weight. In some embodiments, the catalyst provided herein is present in an amount of about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% of the one or more feed sugars by dry weight.

In some embodiments, the catalyst provided herein is present in an amount of from about 0.01% to about 5%, from about 0.02% to about 4%, from about 0.03% to about 3%, or from about 0.05% to about 2% of the aqueous composition by dry weight. In some embodiments, the catalyst provided herein is present in an amount of from about 1% to 2% of the aqueous composition by dry weight. In some embodiments, the catalyst provided herein is present in an amount of about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% of the aqueous composition by dry weight.

In some embodiments, the catalyst provided herein is a combination of two or more different catalysts. In some embodiments, the catalyst comprises a recyclable catalyst such as resins and polymeric catalysts and a non-recyclable catalyst. In some embodiments, where the catalyst comprises at least two different catalysts, each of the catalyst is present in an amount provided herein. In other embodiments, where the catalyst comprises at least two different catalysts, the at least two different catalysts are present in aggregate in an amount provided herein.

In some embodiments, the catalyst is added into the aqueous composition in a dry form. In other embodiments, the catalyst is added into the aqueous composition in a wet form such as in an aqueous solution. In some embodiment, the catalyst is combined with the one or more feed sugars before the addition of water. In other embodiments, the catalyst is dissolved into water before its combining with the one or more feed sugars. In some embodiments, the method provided herein comprises producing an aqueous composition by combining the one or more feed sugars in the de-hydrate form and the catalyst in a wet form (e.g., as an aqueous solution).

Addition of Water

In some embodiments, a herein described method of manufacturing oligosaccharide preparations comprises adding water to form an aqueous composition. In some embodiments, all or part of the water in the aqueous composition is added as free water. In other embodiments, all of the water in the aqueous composition is added as bonded water, for example, in saccharide mono- or di-hydrate. In some embodiments, all of the water in the aqueous composition is added as bonded water in monosaccharide mono-hydrate, such as glucose mono-hydrate. In certain embodiments, all or part of the water in the aqueous composition is added with the catalyst, i.e., via a catalyst solution.

Water Content

As the methods of manufacturing the oligosaccharide preparations proceed, water can be produced through reaction. For example, in some embodiments, water is produced (i) with the formation of a glycosidic bond, (ii) with the formation of an anhydro-subunit, or (iii) through other mechanisms or sources. As the sugar condensation and dehydration reactions both involve water, in some embodiments, the water content influences the composition of the oligosaccharide preparation.

Further, in some embodiments, water content influences the viscosity of the aqueous composition, which in turn may affect the effectiveness of mixing of the aqueous composition. For example, in some embodiments, an overly viscous aqueous composition can lead to an undesirable heterogeneous catalyst distribution in the aqueous composition.

Moreover, in some embodiments, very low water content may lead to the solidification of the aqueous composition, which prevents effective mixing. On the other hand, in some other embodiments, exceedingly high water content may impede sugar condensation reaction and lower the level of the anhydro-subunits. Accordingly, the present disclosure describes suitable water content for the manufacturing of oligosaccharide preparations.

In some embodiments, a herein described method of manufacturing oligosaccharide preparation comprises forming and/or heating an aqueous composition. In some embodiments, the aqueous composition comprises from about 0% to about 80%, from about 0% to about 70%, from about 0% to about 60%, from about 0% to about 50%, from about 0% to about 40%, from about 0% to about 35%, from about 0% to about 30%, from about 0% to about 25%, from about 0% to about 20%, from about 0% to about 19%, from about 0% to about 18%, from about 0% to about 17%, from about 0% to about 16%, from about 0% to about 15%, from about 0% to about 14%, from about 0% to about 13%, from about 0% to about 12%, from about 0% to about 11%, from about 0% to about 10%, from about 0% to about 9%, from about 0% to about 8%, from about 0% to about 7%, from about 0% to about 6%, from about 0% to about 5%, from about 0% to about 4%, from about 0% to about 3%, from about 0% to about 2%, or from about 0% to about 1% of water by total weight. In some embodiments, the aqueous composition comprises from about 1% to about 20%, from about 1% to about 18%, from about 1% to about 16%, from about 1% to about 14%, from about 1% to about 12%, from about 1% to about 10%, from about 1% to about 8%, from about 1% to about 6%, or from about 1% to about 4% of water by total weight. In some embodiments, the aqueous composition comprises from about 3% to about 16%, from about 3% to about 14%, from about 3% to about 12%, from about 3% to about 10%, from about 3% to about 8%, from about 3% to about 6%, from about 5% to about 16%, from about 5% to about 14%, from about 5% to about 12%, from about 5% to about 10%, from about 7% to about 16%, from about 7% to about 14%, from about 7% to about 12%, from about 7% to about 10%, or from about 8% to about 10% of water by total weight. In some embodiments, the aqueous composition comprises about 1%, about 2%, about 3%, about 4%, about 5%, about 6%, about 7%, about 8%, about 9%, about 10%, about 11%, about 12%, about 13%, about 14%, or about 15% of water by total weight. In some embodiments, the aqueous composition comprises about 9% water by total weight. It should be understood, however, that the amount of water in the aqueous composition can be adjusted based on the reaction conditions and specific catalyst used. In some embodiments, the water content in the aqueous composition as disclosed above is measured at the beginning of the reaction, for example, before heating the feed sugars. In some embodiments, the water content in the aqueous composition as disclosed above is measured at the end of the polymerization or condensation reaction. In some embodiments, the water content in the aqueous composition as disclosed above is measured as an average water content of the beginning of the reaction and at the end of the reaction.

In certain embodiments, a method described herein can further comprise monitoring the content of water present in the aqueous composition and/or the ratio of water to sugars or catalyst over a period of time. In some embodiments, the method further comprises removing at least a portion of water in the aqueous composition, for example, by distillation. Any method known in the art can be used to remove water from the aqueous composition, including, for example, by vacuum filtration, vacuum distillation, heating, steam, hot air, and/or evaporation.

In some embodiments, herein described oligosaccharide preparations are hygroscopic. Thus, in some embodiments, the hygroscopicity of the feed sugars and the oligosaccharides formed in the polymerization can affect the rate by which the water can be removed from the aqueous composition.

In some embodiments, a herein described method comprises removing at least a portion of water in the aqueous composition such that the water content in the aqueous composition is from about 1% to about 20%, from about 1% to about 18%, from about 1% to about 16%, from about 1% to about 14%, from about 1% to about 12%, from about 1% to about 10%, from about 1% to about 8%, from about 2% to about 16%, from about 2% to about 14%, from about 2% to about 12%, from about 2% to about 10%, from about 2% to about 8%, from about 2% to about 6%, from about 4% to about 16%, from about 4% to about 14%, from about 4% to about 12%, from about 4% to about 10%, from about 4% to about 8%, from about 6% to about 16%, from about 6% to about 12%, from about 6% to about 10%, or from about 6% to about 8% by total weight. In some embodiments, the method comprises removing at least a portion of water in the aqueous composition such that the water content in the aqueous composition is from about 2% to about 10%, from about 2% to about 8%, or from about 4% to about 8% by total weight. In some embodiments, the method comprises removing at least a portion of water in the aqueous composition such that the water content in the aqueous composition is about 2%, about 3%, about 4%, about 5%, about 6%, about 7%, about 8%, about 9%, or about 10% by total weight. In some embodiments, the method comprises removing at least a portion of water in the aqueous composition such that the water content in the aqueous composition is from about 4% to about 8% by total weight. In some embodiments, the method comprises removing at least a portion of water in the aqueous composition such that, at the end of the polymerization and/or condensation reaction, the water content in the aqueous composition is a water content as disclosed above. In some embodiments, the method comprises removing at least a portion of water in the aqueous composition such that, at the beginning of the polymerization and/or condensation reaction, the water content in the aqueous composition is a water content as disclosed above. In some embodiments, the method comprises removing at least a portion of water in the aqueous composition such that, the average water content in the aqueous composition at the beginning and the end of the polymerization and/or condensation reaction is within a range as disclosed above. In some embodiments, the method comprises removing at least a portion of water in the aqueous composition such that, throughout the polymerization and/or condensation reaction, the water content in the aqueous composition remains within a range as disclosed above.

In some embodiments, a herein described method comprises adding at least a portion of water in the aqueous composition such that the water content in the aqueous composition is from about 1% to about 20%, from about 1% to about 18%, from about 1% to about 16%, from about 1% to about 14%, from about 1% to about 12%, from about 1% to about 10%, from about 1% to about 8%, from about 2% to about 16%, from about 2% to about 14%, from about 2% to about 12%, from about 2% to about 10%, from about 2% to about 8%, from about 2% to about 6%, from about 4% to about 16%, from about 4% to about 14%, from about 4% to about 12%, from about 4% to about 10%, from about 4% to about 8%, from about 6% to about 16%, from about 6% to about 12%, from about 6% to about 10%, or from about 6% to about 8% by total weight. In some embodiments, the method comprises adding at least a portion of water in the aqueous composition such that the water content in the aqueous composition is from about 2% to about 10%, from about 2% to about 8%, or from about 4% to about 8% by total weight. In some embodiments, the method comprises adding at least a portion of water in the aqueous composition such that the water content in the aqueous is about 2%, about 3%, about 4%, about 5%, about 6%, about 7%, about 8%, about 9%, or about 10% by total weight. In some embodiments, the method comprises adding at least a portion of water in the aqueous composition such that the water content in the aqueous composition is from about 4% to about 8% by total weight. In some embodiments, the method comprises adding at least a portion of water in the aqueous composition such that, at the end of the polymerization and/or condensation reaction, the water content in the aqueous composition is a water content as disclosed above. In some embodiments, the method comprises adding at least a portion of water in the aqueous composition such that, at the beginning of the polymerization and/or condensation reaction, the water content in the aqueous composition is a water content as disclosed above. In some embodiments, the method comprises adding at least a portion of water in the aqueous composition such that, the average water content in the aqueous composition at the beginning and the end of the polymerization and/or condensation reaction is within a range as disclosed above. In some embodiments, the method comprises adding at least a portion of water in the aqueous composition such that, throughout the polymerization and/or condensation reaction, the water content in the aqueous composition remains within a range as disclosed above.

In some embodiments, the degrees of polymerization of the oligosaccharides and/or the amount and type of the anhydro-subunits within the oligosaccharide preparation can be regulated by adjusting or controlling the content of water present in the aqueous composition throughout the manufacturing process. For example, in some embodiments, the degrees of polymerization of the oligosaccharides and the amount of the anhydro-subunits are increased by decreasing the water content.

Accordingly, in some embodiments, a herein described method comprises in-process control (IPC) of the water content, which can comprise monitoring water content, maintaining water content, increasing water content, decreasing water content, or any combination thereof. In some embodiments, an IPC process comprises maintaining the water content while the aqueous composition is heated to a temperature described herein. In some embodiments, the method comprises maintaining the water content for the time sufficient to induce polymerization. In some embodiments, the method comprises maintaining the water content within a disclosed range by either adding water or removing water from the aqueous composition, or both. In some embodiments, the method comprises maintaining the water content within a disclosed range by distillation. In some embodiments, the method comprises maintaining the water content within a disclosed range by vacuum distillation. In some embodiments, the method comprises maintaining the water content within a disclosed range by distillation under atmosphere pressure.

In some embodiments, the water content of the aqueous composition is maintained within a range of from about 1% to about 20%, from about 1% to about 18%, from about 1% to about 16%, from about 1% to about 14%, from about 1% to about 12%, from about 1% to about 10%, from about 1% to about 8%, from about 2% to about 16%, from about 2% to about 14%, from about 2% to about 12%, from about 2% to about 10%, from about 2% to about 8%, from about 2% to about 6%, from about 4% to about 16%, from about 4% to about 14%, from about 4% to about 12%, from about 4% to about 10%, from about 4% to about 8%, from about 6% to about 16%, from about 6% to about 12%, from about 6% to about 10%, or from about 6% to about 8% by total weight. In some embodiments, the water content of the aqueous composition is maintained within a range of from about 2% to about 10%, from about 2% to about 8%, or from about 4% to about 8% by total weight. In some embodiments, the water content of the aqueous composition is maintained within a range of from about 2% to about 8% by total weight.

In some embodiments, a suitable water content varies depending on the reaction temperature and the type of feed sugars. In some embodiments, the water content is from about 8% to about 9% at 120° C. In some embodiments, the water content is from about 5% to about 7% at 130° C. In some embodiments, the water content for manufacturing a gluco-oligosaccharide preparation is from about 5% to about 7% at 130° C. In some embodiments, the water content for manufacturing a gluco-galacto-oligosaccharide preparation is from about 5% to about 6% at 130° C.

The water content of the aqueous composition can be determined by a variety of analytical methods and instruments. In some embodiments, the water content is determined by an evaporation method (e.g., loss on drying technique), a distillation method, or a chemical reaction method (e.g., Karl Fischer titration). In some embodiments, the water content is determined by an analytical instrument such as a moisture analyzer. In some embodiments, the water content is determined by Karl Fischer titration.

In some embodiments, the water content of the aqueous composition is measured during the reaction and is used to implement in-process control (IPC) of the water content. In certain embodiments, the water content of the reaction is measured by Karl-Fisher titration, IR spectroscopy, NIR spectroscopy, conductivity, viscosity, density, mixing torque, or mixing energy. In some embodiments, the measurement of the water content of the reaction is used to control an apparatus that actively adjusts the water content of the reaction, such as a water addition pump or flow valve.

Figure 23:
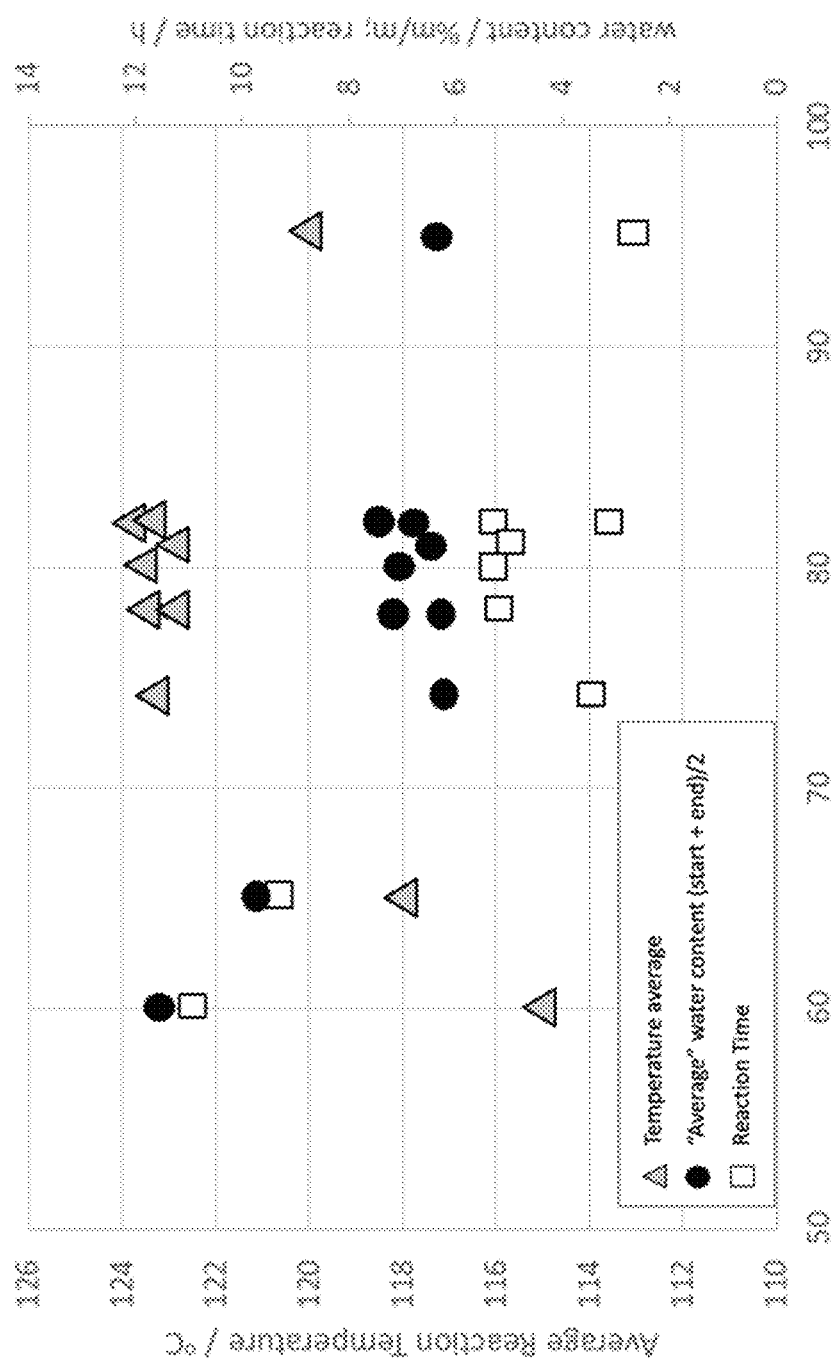
FIG. 23 illustrates the effect of reaction temperature, water content, and reaction time on the content of DP2 anhydro-subunit containing oligosaccharides in the oligosaccharide preparations, as compared to an oligosaccharide preparation according to Example 2.

Without being bound by theory, it is believed that water content during the sugar polymerization and/or condensation reaction can affect the level of the anhydro-subunits in a herein described oligosaccharide preparation. For example, as illustrated in FIG. 23, in some embodiments, a higher water content correlates with a lower level of anhydro-subunits. In some embodiments, a lower reaction temperature can correlate with a lower level of anhydro-subunits content.

Temperature

In some embodiments, the degrees of polymerization of the oligosaccharides and/or the amount and type of the anhydro-subunits within the oligosaccharide preparation can be regulated by adjusting the temperature, to which the aqueous composition is heated. In some embodiments, a herein described method of manufacturing an oligosaccharide preparation comprises heating the aqueous composition to a temperature of from about 80° C. to about 250° C., from about 90° C. to about 200° C., from about 100° C. to about 200° C., from about 100° C. to about 180° C., from about 110° C. to about 170° C., from about 120° C. to about 160° C., from about 130° C. to about 150° C., or from about 135° C. to about 145° C. In some embodiments, the method of manufacturing an oligosaccharide preparation comprises heating the aqueous composition to a temperature of from about 100° C. to about 200° C., from about 100° C. to about 180° C., from about 110° C. to about 170° C., from about 120° C. to about 160° C., from about 130° C. to about 150° C., or from about 135° C. to about 145° C. In some embodiments, the method of manufacturing an oligosaccharide preparation comprises heating the aqueous composition to a temperature of from about 135° C. to about 145° C. In other embodiments, the method of manufacturing an oligosaccharide preparation comprises heating the aqueous composition to a temperature of from about 125° C. to about 135° C.

Reaction Time

In some embodiments, a herein described method of manufacturing an oligosaccharide preparation comprises heating the aqueous composition for a sufficient time. In some embodiments, the degrees of polymerization of the oligosaccharides manufactured according to the methods described herein can be regulated by the reaction time.

In some embodiments, the sufficient time is prescribed by a number of hours. For example, in some embodiments, the sufficient time is at least 30 minutes, at least 1 hour, at least 2 hours, at least 3 hours, at least 4 hours, at least 5 hours, at least 6 hours, at least 7 hour, at least 8 hours, at least 9 hours, or at least 10 hours. In some embodiments, the sufficient time is from about 1 to about 24 hours, from about 1 to about 16 hours, from about 1 to about 8 hours, from about 1 to about 4 hours, from about 1 to about 3 hours, from about 1 to about 2 hours, from about 2 to about 12 hours, from about 2 to about 10 hours, from about 2 to about 8 hours, from about 2 to about 6 hours, from about 2 to about 4 hours, from about 3 to about 8 hours, from about 3 to about 6 hours, from about 3 to about 5 hours, or from about 3 to about 4 hours.

In other embodiments, the sufficient time is determined by measuring one or more chemical or physical properties of the oligosaccharide preparation, for example, water content, viscosity, molecular weight, anhydro-subunit content, the distribution of degree of polymerization, evolved condensate water, reaction water content, density, or color.

In some embodiments, the reaction stopping time is determined by at least one in process control (IPC) measured in real time. In some embodiments, the IPC measures water content, viscosity, molecular weight, anhydro-subunit content, the distribution of degree of polymerization, evolved condensate water, reaction water content, density, or color.

In some embodiments, embodiments, the in-process control measures the continuous viscosity. In some embodiments, the in-process control measures the evolved condensate water. In some embodiments, the in-process control is an in-situ IR measurement (e.g., Karl-Fisher). In some embodiments, the in-process control is a real time HPLC measurement. In some embodiments, the in-process control is a GC measurement. In some embodiments, the in-process control measures density. In some embodiments, the in-process control measures color (e.g., as measured by UV/Vis).

In some embodiments, the in-process control measurement is compared to a pre-determined criterion; and in some embodiments, when said pre-determined criterion is reached the reaction is stopped. In some embodiments, the in-process control measurement is compared to a pre-determined criterion; and in some embodiments, when said in process control measurement is within 0.1%, 0.2%, 0.3%, 0.4%, 0.5%, 0.6%, 0.7%, 0.8%, 0.9%, or 1% of said pre-determined criterion the reaction is stopped.

In some embodiments, the molecular weight of the oligosaccharide preparation is monitored during polymerization. In some embodiments, the method comprises heating the aqueous composition for a time sufficient for the aqueous composition to reach a number average molecular weight or weight average molecular weight as described herein. In certain embodiments, the method comprises heating the aqueous composition for a time sufficient for the aqueous composition to reach a number average molecular weight within a range of from about 300 to about 5000 g/mol, from about 500 to about 5000 g/mol, from about 700 to about 5000 g/mol, from about 500 to about 2000 g/mol, from about 700 to about 2000 g/mol, from about 700 to about 1500 g/mol, from about 300 to about 1500 g/mol, from about 300 to about 2000 g/mol, from about 400 to about 1000 g/mol, from about 400 to about 900 g/mol, from about 400 to about 800 g/mol, from about 500 to about 900 g/mol, or from about 500 to about 800 g/mol. In certain embodiments, the method comprises heating the aqueous composition for a time sufficient for the aqueous composition to reach a number average molecular weight of from about 500 to about 2000 g/mol. In certain embodiments, the method comprises heating the aqueous composition for a time sufficient for the aqueous composition to reach a weight average molecular weight within a range of from about 300 to about 5000 g/mol, from about 500 to about 5000 g/mol, from about 700 to about 5000 g/mol, from about 500 to about 2000 g/mol, from about 700 to about 2000 g/mol, from about 700 to about 1500 g/mol, from about 300 to about 1500 g/mol, from about 300 to about 2000 g/mol, from about 400 to about 1300 g/mol, from about 400 to about 1200 g/mol, from about 400 to about 1100 g/mol, from about 500 to about 1300 g/mol, from about 500 to about 1200 g/mol, from about 500 to about 1100 g/mol, from about 600 to about 1300 g/mol, from about 600 to about 1200 g/mol, or from about 600 to about 1100 g/mol. In certain embodiments, the method comprises heating the aqueous composition for a time sufficient for the aqueous composition to reach a weight average molecular weight of from about 700 to about 3000 g/mol.

In some embodiments, the sufficient time is the time required for the aqueous composition to reach reaction equilibrium at the respective reaction temperature. Accordingly, in some embodiments, the method comprises heating the aqueous composition for a time sufficient for the aqueous composition to reach equilibrium. For example, in some embodiments, the equilibrium is determined by measuring the molecular weight, viscosity, or DP distribution of the aqueous composition.

In certain embodiments, the equilibrium is determined by measuring the number average or weight average molecular weight of the aqueous composition. In some embodiments, the equilibrium is determined by the number or weight average molecular weight of the aqueous composition that remains essentially unchanged over time. In some embodiments, the equilibrium is determined by a change of the number or weight average molecular weight of the aqueous composition that is less than certain percentage over a period of time. In some embodiments, the molecular weight of the aqueous composition is measured by HPLC or SEC.

In some embodiments, the equilibrium is determined by a change of the number or weight average molecular weight of the aqueous composition of less than 25%, less than 20%, less than 15%, less than 10%, or less than 5% over a period of time. In some embodiments, the equilibrium is determined by a change of the number or weight average molecular weight of the aqueous composition over a period of 3 hours, 2 hours, 1 hour, 30 minutes, 20 minutes, or 10 minutes. In some embodiments, the equilibrium is determined by a change of the weight average molecular weight of the aqueous composition of less than 15% over the period of 1 hour.

In certain embodiments, the equilibrium is determined by measuring the viscosity of the aqueous composition. In some embodiments, the equilibrium is determined by the viscosity of the aqueous composition that remains essentially unchanged over time. In some embodiments, the equilibrium is determined by a change of the viscosity of the aqueous composition that is less than certain percentage over a period of time. In some embodiments, the viscosity of the aqueous composition is measured by a viscometer or rheometer.

In some embodiments, the equilibrium is determined by a change of the viscosity of the aqueous composition of less than 25%, less than 20%, less than 15%, less than 10%, or less than 5% over a period of time. In some embodiments, the equilibrium is determined by a change of the viscosity of the aqueous composition over a period of 3 hours, 2 hours, 1 hour, 30 minutes, 20 minutes, or 10 minutes. In some embodiments, the equilibrium is determined by a change of the viscosity of the aqueous composition of less than 15% over the period of 1 hour.

In certain embodiments, the equilibrium is determined by measuring the DP distribution of the aqueous composition. In some embodiments, the equilibrium is determined by the DP distribution of the aqueous composition that remains essentially unchanged over time. In some embodiments, a change of the DP distribution of the aqueous composition is determined by calculating a series of Km, wherein $$Km = \frac{[DP_m][H_2O]}{[DP_{m-1}][DP1]},$$

wherein [H$_2$O] represents the molar water concentration (mol/L), and [DP1], [DPm$_{-1}$], and [DPm] represent the molar concentrations of oligosaccharides (mol/L) in the DP1, DPm$_{-1}$, and DPm fraction, respectively. For example, K2 equals [DP2][H$_2$O]/[DP1][DP1] according to the above formula. In some embodiments, m is an integer larger than 1 and less than n. In some embodiments, m is an integer larger than 1 and less than or equal to n. In some embodiments, m equals n. In some embodiments, m is 2, 3, 4, 5, 6, 7, 8, 9, or 10.

In some embodiments, the concentration of the oligosaccharides in the DP1, DPm-1, and DPm fractions are determined by SEC, HPLC, FFF, A4F, mass spectrometry, or any other suitable method. In some embodiments, the concentration of the oligosaccharides in the DP1, DPm-1, and DPm fractions are determined by SEC such as GPC. In some embodiments, the concentration of the oligosaccharides in the DP1, DPm-1, and DPm fractions are determined by mass spectrometry such as GC-MS, LC-MS/MS, and MALDI-MS. In some embodiments, the concentration of the oligosaccharides in the DP1, DPm−1, and DPm fractions are determined by HPLC. In some embodiments, the water concentration is determined by an evaporation method (e.g., loss on drying technique), a distillation method, or by a chemical reaction method (e.g., Karl Fischer titration). In some embodiments, the water concentration is determined by any suitable analytical instrument such as a moisture analyzer.

In some embodiments, the method comprises calculating a series of at least 3, at least 4, at least 5, at least 6, at least 7, at least 8, at least 9, at least 10, at least 15, at least 20, at least 30, at least 40, or at least 50 Km numbers. In some embodiments, the method comprises calculating a series of at least 3, at least 4, at least 5, at least 6, at least 7, at least 8, at least 9, at least 10, or at least 15 Km numbers. In some embodiments, the method comprises calculating about 3, 4, 5, 6, 7, 8, 9, 10, or 15 Km numbers. In some embodiments, the method comprises calculating K2 to K4, K2 to K5, K2 to K6, K2 to K7, K2 to K8, K2 to K9, K2 to K10, K2 to K11, K2 to K12, K2 to K13, K2 to K14, K2 to K15, K3 to K5, K3 to K6, K3 to K7, K3 to K8, K3 to K9, K3 to K10, K3 to K11, K3 to K12, K3 to K13, K3 to K14, or K3 to K15. In certain embodiments, the method comprises calculating K2 to K4 or K3 to K5.

In some embodiments, the value of Km depends on the temperature, water concentration, and/or the amount and type of the feed sugars. In some embodiments, Km is from about 0.1 to about 100, from about 0.1 to about 90, from about 0.1 to about 80, from about 0.1 to about 70, from about 0.1 to about 60, from about 0.1 to about 50, from about 0.1 to about 40, from about 0.1 to about 30, from about 0.1 to about 25, from about 0.1 to about 20, or from about 0.1 to about 15. In some embodiments, Km is from about 1 to about 100, from about 1 to about 90, from about 1 to about 80, from about 1 to about 70, from about 1 to about 60, from about 1 to about 50, from about 1 to about 40, from about 1 to about 30, from about 1 to about 25, from about 1 to about 20, from about 1 to about 15, from about 1 to about 10, from about 5 to about 50, from about 5 to about 40, from about 5 to about 30, from about 5 to about 20, from about 5 to about 15, or from about 5 to about 10. In some specific embodiments, Km is from about 1 to about 15 or from about 5 to about 15.

In some embodiments, an average, a standard deviation, and/or a relative standard deviation are determined for the series of Km calculated. As used herein, a relative standard deviation is expressed in percentage, and is obtained by multiplying the standard deviation by 100 and dividing this product by the average.

In some embodiments, the equilibrium is determined by the relative standard deviation of the series of Km of less than 30%, less than 25%, less than 20%, less than 15%, less than 10%, less than 9%, less than 8%, less than 7%, less than 6%, less than 5%, less than 4%, less than 3%, less than 2%, or less than 1%. In some embodiments, the equilibrium is determined by the relative standard deviation of the series of Km of less than 15%, less than 10%, or less than 5%.

Post-Reaction Steps

In some embodiments, a herein described method of manufacturing oligosaccharide preparations further comprises one or more additional processing steps after heating the aqueous composition at a temperature and for a sufficient time. In some embodiments, the additional processing steps comprise, for example, separation (such as chromatographic separation), dilution, concentration, drying, filtration, demineralization, extraction, decolorization, or any combination thereof. For example, in some embodiments, the method comprises a dilution step and a decolorization step. In some embodiments, the method comprises a filtration step and a drying step.

In some embodiments, the method comprises a dilution step, where water is added into the oligosaccharide preparation to make a syrup of oligosaccharide preparation. In some embodiments, the concentration of oligosaccharide preparation in the syrup is from about 5% to about 80%, from about 10% to about 70%, from about 10% to about 60%, from about 10% to about 50%, from about 10% to about 40%, from about 10% to about 30%, or from about 15% to about 25%. In other embodiments, the method does not comprise a dilution step, but rather, the oligosaccharide preparation is allowed to solidify. In some embodiments, the method comprises a filtration step. In some embodiments, the method comprises recycling the catalyst by filtration.

In some embodiments, the method described herein further comprises a decolorization step. In some embodiments, the oligosaccharide preparation may undergo a decolorization step using any method known in the art, including, for example, treatment with an absorbent, activated carbon, chromatography (e.g., using ion exchange resin), hydrogenation, and/or filtration (e.g., microfiltration).

In some embodiments, the oligosaccharide preparation is contacted with a material to remove salts, minerals, and/or other ionic species. In certain embodiments, the oligosaccharide preparation is flowed through an anionic/cationic exchange column pair. In one embodiment, the anionic exchange column contains a weak base exchange resin in a hydroxide form and the cationic exchange column contains a strong acid exchange resin in a protonated form.

In some embodiments, the method comprises a concentration step. In some embodiments, the centration step produces an oligosaccharide preparation with increased concentration. For example, in some embodiments, the concentration step comprises evaporation (e.g., vacuum evaporation), drying (e.g., freeze-drying and spray drying) or any combination thereof.

In some embodiments, the method comprises an isolation step, wherein at least a portion of the oligosaccharide preparation is separated. In some embodiments, the isolation step comprises crystallization, precipitation, filtration (e.g., vacuum filtration), and centrifugation, or any combination thereof.

In some embodiments, the method comprises a separation step. In some embodiments, the separation step comprises separating at least a portion of the oligosaccharide preparation from at least a portion of the catalyst, from at least a portion of the unreacted feed sugars, or from both. In some embodiments, the separation step comprises filtration, chromatography, differential solubility, precipitation, extraction, or centrifugation.

Reactors

The methods described herein can comprise the use of one or more reactors suitable for sugar condensation, considering the reaction temperature, pH, pressure, and other factors. In some embodiments, the one or more suitable reactors comprise a fed-batch stirred reactor, a batch stirred reactor, a continuous flow stirred reactor, a continuous plug-flow column reactor, an attrition reactor, or a reactor with stirring induced by an electromagnetic field. In some embodiments, the one or more suitable reactors comprise a reactor described in Ryu, S. K., and Lee, J. M., Bioconversion of waste cellulose by using an attrition bioreactor, Biotechnol. Bioeng. 25: 53-65(1983); Gusakov, A. V., and Sinitsyn, A. P., Kinetics of the enzymatic hydrolysis of cellulose: 1. A mathematical model for a batch reactor process, Enz. Microb. TechnoL, 7: 346-352 (1985); Gusakov, A. V., Sinitsyn, A. P., Davydkin, I. Y., Davydkin, V. Y., Protas, O. V., Enhancement of enzymatic cellulose hydrolysis using a novel type of bioreactor with intensive stirring induced by electromagnetic field, Appl. Biochem. Biotechnol., 56: 141-153(1996); or Fernanda de Castilhos Corazza, Flavio Faria de Moraes, Gisella Maria Zanin and Ivo Neitzel, Optimal control in fed-batch reactor for the cellobiose hydrolysis, Acta Scientiarum. Technology, 25: 33-38 (2003).

In some embodiments, the one or more suitable reactors comprise fluidized bed, upflow blanket, immobilized, or extruder type reactors for hydrolysis and/or fermentation. In some embodiments, the one or more suitable reactors comprise an open reactor, a closed reactor, or both. In some embodiments, where the method comprises a continuous process, the one or more suitable reactors can include a continuous mixer such as a screw mixer.

Process

In some embodiments, a herein described method of manufacturing oligosaccharide preparations comprises a batch process, a continuous process, or both. In some embodiments, the method of manufacturing the oligosaccharide preparation comprises a batch process. For example, in some embodiments of the batch process, manufacturing of subsequent batches of the oligosaccharide preparation does not start until the completion of the current batch. In some embodiments, during the batch process, all or a substantial amount of oligosaccharide preparation is removed from the reactor. In some embodiments, during the batch process, all the feed sugars and the catalyst are combined in a reactor before the aqueous composition is heated to the described temperature or before the polymerization is induced. In some embodiments, during the batch process, the feed sugars are added before, after, or simultaneous with the addition of the catalyst.

In some embodiments, the batch process is a fed-batch process, wherein all the feed sugars are not added into the reactor at the same time. In some embodiments of the fed-batch process, at least a portion of the feed sugars are added into the reactor during polymerization or after the aqueous composition is heated to the described temperature. In some embodiments of the fed-batch process, at least 10%, 20%, 30%, 40%, 50%, or 60% by weight of the feed sugars are added into the reactor during polymerization or after the aqueous composition is heated to the described temperature.

In some embodiments, the method of manufacturing the oligosaccharide preparation comprises a continuous process. For example, in some embodiments of the continuous process, the contents of the reactor continuously flow through the reactor. In some embodiments, the combination of the feed sugars with the catalyst and the removal of at least a portion of the oligosaccharide preparation are performed concurrently.

In some embodiments, the method of manufacturing the oligosaccharide preparation comprises a single-pot or multi-pot process. For example, in some embodiments of the single-pot process, the polymerization is performed in a single reactor. For another example, in some embodiments of the multi-pot process, the polymerization is performed in more than one reactor. In some embodiments of the multi-pot process, the method comprises 2, 3, or more reactors. In some embodiments of the multi-pot process, the method comprises a combination step, where the polymerization products from two or more reactors are combined.

IV. Nutritional Composition Comprising Oligosaccharide Preparations

Provided herein are nutritional compositions comprising an oligosaccharide preparation. In certain embodiments, provided herein are nutritional compositions comprising a described oligosaccharide preparation, wherein the presence and/or concentration of the oligosaccharide preparation within the nutritional compositions can be selectively determined and/or detected. Oligosaccharide preparations, which exhibit complex functional modulation of a microbial community, can be important components of nutritional compositions. Thus, the presence and/or concentration of an oligosaccharide preparation within nutritional compositions can be one of the factors that need to be measured in the quality control and manufacturing process of the nutritional compositions. Accordingly, the provided nutritional compositions are advantageous in terms of quality control and manufacturing purposes as the presence and/or concentration of the oligosaccharide preparation can be selectively determined and/or detected. For example, in some embodiments, the presence and concentration of the oligosaccharide preparation can be determined and/or detected by measuring a signal associated with the anhydro-subunit containing oligosaccharides.

In some embodiments, the nutritional composition is an animal feed composition. In some embodiments, the nutritional composition comprises a base nutritional composition.

Base Nutritional Compositions

In some embodiments, a herein described nutritional composition comprises a base nutritional composition and a disclosed oligosaccharide preparation. In some embodiments, the base nutritional composition comprises a carbohydrate source that is different from the oligosaccharide preparation. For example, in some embodiments, the base nutritional composition comprises a naturally occurring carbohydrate source such as starch and plant fibers. In some embodiments, the base nutritional composition comprises starch. In some embodiments, the base nutritional composition comprises plant fibers.

In some embodiments, the base nutritional composition comprises one or more carbohydrate sources that are derived from: seeds, roots, tubers, corn, tapioca, arrowroot, wheat, rice, potatoes, sweet potato, sago, beans (e.g., favas, lentils, mung beans, peas, and chickpeas), maize, cassava, or other starchy foods (e.g., acorns, arrowroot, arracacha, bananas, barley, breadfruit, buckwheat, *canna*, colacasia, katakuri, kudzu, malanga, millet, oats, oca, polynesian arrowroot, sorghum, rye, taro, chestnuts, water chestnuts, and yams).

In some embodiments, the base nutritional composition comprises one or more carbohydrate sources that are derived from: legumes (e.g., peas, soybeans, lupins, green beans, and other beans), oats, rye, chia, barley, fruits (e.g., figs, avocados, plums, prunes, berries, bananas, apple skin, quinces, and pears), vegetables (e.g., broccoli, carrots, cauliflower, zucchini, celery, nopal, and Jerusalem artichokes), root tubers, root vegetables (e.g., sweet potatoes and onions), *psyllium* seed husks, seeds (e.g., flax seeds), nuts (e.g., almonds), whole grain foods, wheat, corn bran, lignans, or any combination thereof. In some embodiments, the base nutritional composition comprises one or more plant fibers derived from wheat bran, sugar beet pulp, fuzzy cottonseeds, soy hulls, or any combination thereof.

In some embodiments, the base nutritional composition comprises less than 500 ppm, less than 400 ppm, less than 300 ppm, less than 200 ppm, less than 100 ppm, less than 50 ppm, less than 10 ppm, less than 5 ppm, or less than 1 ppm anhydro-subunits or anhydro-subunit containing oligosaccharides. In some embodiments, the base nutritional composition comprises less than 50 ppm, less than 10 ppm, less than 5 ppm, or less than 1 ppm anhydro-subunits or anhydro-subunit containing oligosaccharides. In some embodiments, the base nutritional composition is essentially free of anhydro-subunits.

In some embodiments, the base nutritional composition lacks a detectable level of anhydro-subunits. Depending on the methods of detecting or determination, an anhydro-subunit level below a certain threshold can be undetectable. For example, in some embodiments, a detectable level of anhydro-subunit can refer to at least 1000 ppm, at least 500 ppm, at least 400 ppm, at least 300 ppm, at least 200 ppm, at least 100 ppm, at least 50 ppm, at least 10 ppm, at least 5 ppm, or at least 1 ppm of anhydro-subunit or anhydro-subunit containing oligosaccharides in the base nutritional composition.

In some embodiments, the base nutritional composition comprises a plurality of oligosaccharides. In some embodiments, the base nutritional composition comprises a glycosidic bond type distribution that is different from the oligosaccharide preparation. For example, in some embodiments, the base nutritional composition comprises a higher percentage of α-(1,4) glycosidic linkages than the oligosaccharide preparation. In some embodiments, the glycosidic linkages such as the α-(1,4) glycosidic linkages in the base nutritional compositions are digestible by one or more enzymes. In some embodiments, the glycosidic linkages in the base nutritional composition are more readily digestible and/or hydrolysable than the glycosidic linkages in the oligosaccharide preparation.

In some embodiments, the level of α-(1,2) glycosidic linkage, α-(1,3) glycosidic linkage, α-(1,6) glycosidic linkage, β-(1,2) glycosidic linkage, β-(1,3) glycosidic linkage, β-(1,4) glycosidic linkage, or β-(1,6) glycosidic linkage in the base nutritional composition is at least 2%, at least 3%, at least 4%, at least 5%, at least 6%, at least 7%, at least 8%, at least 9%, at least 10%, at least 11%, at least 12%, at least 13%, at least 14%, or at least 15% lower than the level of the respective glycosidic linkage in the oligosaccharide preparation. In some embodiments, the level of α-(1,2) glycosidic linkage, α-(1,3) glycosidic linkage, α-(1,6) glycosidic linkage, β-(1,2) glycosidic linkage, β-(1,3) glycosidic linkage, β-(1,4) glycosidic linkage, or β-(1,6) glycosidic linkage in the base nutritional composition is at least 10% lower than the level of the respective glycosidic linkage in the oligosaccharide preparation.

In some embodiments, the level of α-(1,4) glycosidic linkage in the base nutritional composition is at least 50%, at least 40%, at least 35%, at least 30%, at least 25%, at least 20%, at least 15%, at least 10%, at least 5%, or at least 2% higher than the level of α-(1,4) glycosidic linkage in the oligosaccharide preparation. In some embodiments, the level of α-(1,4) glycosidic linkage in the base nutritional composition is at least 10% higher than the level of α-(1,4) glycosidic linkage in the oligosaccharide preparation.

Animal Feed Composition

Depending on the type and age of an animal, a nutritional composition can comprise the oligosaccharide preparation and the base nutritional composition at different ratio. For example, the oligosaccharide preparation may be combined with the base nutritional composition at various ratios suitable for the type and age of an animal. In some embodiments, the oligosaccharide preparation is present in the nutritional composition at a concentration of from about 1 to about 10000 ppm, from about 1 to about 5000 ppm, from about 1 to about 3000 ppm, from about 1 to about 2000 ppm, from about 1 to about 1500 ppm, from about 1 to about 1000 ppm, from about 1 to about 500 ppm, from about 1 to about 250 ppm, from about 1 to about 100 ppm, from about 10 to about 5000 ppm, from about 10 to about 3000 ppm, from about 10 to about 2000 ppm, from about 10 to about 1500 ppm, from about 10 to about 1000 ppm, from about 10 to about 500 ppm, from about 10 to about 250 ppm, from about 10 to about 100 ppm, from about 50 to about 5000 ppm, from about 50 to about 3000 ppm, from about 50 to about 2000 ppm, from about 50 to about 1500 ppm, from about 50 to about 1000 ppm, from about 50 to about 500 ppm, from about 50 to about 250 ppm, from about 50 to about 100 ppm, from about 100 to about 5000 ppm, from about 100 to about 3000 ppm, from about 100 to about 2000 ppm, from about 100 to about 1500 ppm, from about 100 to about 1000 ppm, from about 100 to about 500 ppm, from about 100 to about 400 ppm, from about 100 to about 300 ppm, from about 100 to about 200 ppm, from about 200 to about 5000 ppm, from about 200 to about 3000 ppm, from about 200 to about 2500 ppm, from about 200 to about 2000 ppm, from about 200 to about 1500 ppm, from about 200 to about 1000 ppm, from about 200 to about 500 ppm, from about 500 to about 5000 ppm, from about 500 to about 3000 ppm, from about 500 to about 2500 ppm, from about 500 to about 2000 ppm, from about 500 to about 1500 ppm, or from about 500 to about 1000 ppm. In some embodiments, the oligosaccharide preparation is present in the nutritional composition at a concentration of from about 1 to about 5000 ppm, from about 1 to about 1000 ppm, from about 1 to about 500 ppm, from about 10 to about 5000 ppm, from about 10 to about 2000 ppm, from about 10 to about 1000 ppm, from about 10 to about 500 ppm, from about 10 to about 250 ppm, from about 10 to about 100 ppm, from about 50 to about 5000 ppm, from about 50 to about 2000 ppm, from about 50 to about 1000 ppm, from about 50 to about 500 ppm, from about 50 to about 250 ppm, or from about 50 to about 100 ppm. In some embodiments, the oligosaccharide preparation is present in the nutritional composition at a concentration of from about 1 to about 5000 ppm, from about 10 to about 1000 ppm, from about 10 to about 500 ppm, or from about 50 to about 500 ppm.

In some embodiments, the oligosaccharide preparation is present in the nutritional composition at a concentration of greater than 10 ppm, greater than 50 ppm, greater than 100 ppm, greater than 200 ppm, greater than 300 ppm, greater than 400 ppm, greater than 500 ppm, greater than 600 ppm, greater than 1000 ppm, or greater than 2000 ppm. In some embodiments, the oligosaccharide preparation is present in the nutritional composition at a concentration of greater than 10 ppm, greater than 50 ppm, greater than 100 ppm, greater than 200 ppm, or greater than 500 ppm.

In some embodiments, depending on the type and age of an animal, the nutritional composition can further comprise proteins, minerals (such as copper, calcium, and zinc), salts, essential amino acids, vitamins, and/or antibiotics.

Also provided herein is a method of administering a nutritional composition comprising a base nutritional composition and the disclosed oligosaccharide preparation to an animal. In some embodiments, the animal is selected from cattle (e.g., beef cattle and dairy cattle), swine, aquatic animal, poultry, and human. In some embodiments, the animal is swine, such as sows, piglets, and hogs. In other embodiments, the animal is poultry such as chicken, duck, turkey, goose, quail, and hen. In embodiments, the poultry is a broiler, a breeder, or a layer. In some embodiments, the animal is an aquatic animal such salmon, catfish, bass, eel, tilapia, flounder, shrimp, and crab. In some embodiments, the nutritional composition is administered to an animal in a dry form, a liquid form, a paste, or a combination thereof. In some embodiments, the form of administration, the feeding rate, and the feeding schedule can vary depending on the type and age of the animal.

Methods of Producing Nutritional Compositions

Provided herein are methods of manufacturing a nutritional composition comprising: combining an oligosaccharide preparation with a base nutritional composition. In some embodiments, the oligosaccharide preparation comprises anhydro-subunit containing oligosaccharides. In some embodiments, the oligosaccharide preparation comprises a glycosidic bond type distribution that is different from that of the base nutritional composition.

In some embodiments, the oligosaccharide preparation is a synthetic oligosaccharide preparation. In some embodiments, the synthetic oligosaccharide preparation comprises at least n fractions of oligosaccharides each having a distinct degree of polymerization selected from 1 to n (DP1 to DPn fractions). In some embodiments, n is an integer greater than or equal to 2. In some embodiments, n is an integer greater than 2. In some embodiments, n is an integer greater than or equal to 3. In some embodiments, n is an integer within a range of 1 to 100, such as 4, 5, 6, 7, 8, 9, 10, 11, 12, 13, 14, 15, 16, 17, 18, 19, 20, 21, 22, 23, 24, 25, 26, 27, 28, 29, 30, 40, or 50. In some embodiments, each of the DP1 to DPn fraction comprises from 0.1% to 90% anhydro-subunit containing oligosaccharides by relative abundance as measured by mass spectrometry. In some embodiments, the DP1 and DP2 fractions of the oligosaccharide preparation each independently comprises from about 0.1% to about 15% or from about 0.5% to about 10% of anhydro-subunit containing oligosaccharides by relative abundance as measured by mass spectrometry. In some embodiments, the DP1 and DP2 fractions of the oligosaccharide preparation each independently comprises anhydro-subunit containing oligosaccharides within a range of from about 0.1%, 0.5%, 0.6%, 0.7%, 0.8%, 0.9%, 1%, 1.1%, 1.2%, 1.3%, 1.4%, or 1.5% to about 8%, 9%, 10%, 11%, 12%, 15% or 20% by relative abundance as measured by mass spectrometry. In some embodiments, the relative abundance of oligosaccharides in each of the n fractions decreases monotonically with its degree of polymerization. In some embodiments, the relative abundance of oligosaccharides in at least 5, 10, 20, or 30 DP fractions decreases monotonically with its degree of polymerization.

In some embodiments, the method of manufacturing a nutritional composition comprises mixing the oligosaccharide preparation with the base nutritional composition. For example, in some embodiments, the mixing may be performed by an industrial blender and/or mixer such as drum blender, double cone blender, ribbon blender, V blender, shear mixer, and paddle mixer.

In some embodiments, the method of manufacturing a nutritional composition further comprises a herein described quality control step. In some embodiments, the herein described quality control step comprises determining a level of a signal in a sample of the nutritional composition and calculating a concentration of the oligosaccharide preparation in the nutritional composition based on the level of the signal. In some embodiments, the herein described quality control step comprises detecting a signal in a sample of the nutritional composition through analytical instrumentation, and accepting or rejecting a batch of the nutritional composition based on the presence or absence of the signal. In some embodiments, the herein described quality control step comprises detecting, through analytical instrumentation, the presence or absence of a first signal in a first sample of the nutritional composition, and a second signal in a second sample of the nutritional composition, and comparing the first signal and the second signal. In some embodiments, the signal, the first signal, and/or the second signal is/are (i) indicative of one or more anhydro-subunit containing oligosaccharides, (ii) associated with a degree of polymerization (DP) distribution of oligosaccharides, or (iii) associated with α-(1,2) glycosidic linkage, α-(1,3) glycosidic linkage, α-(1,6) glycosidic linkage, β-(1,2) glycosidic linkage, β-(1,3) glycosidic linkage, β-(1,4) glycosidic linkage, or β-(1,6) glycosidic linkage of oligosaccharides.

Additionally, in some embodiments, the method of manufacturing a nutritional composition comprises, after performing the quality control step, further mixing the oligosaccharide preparation with the base nutritional composition, adjusting the level of the oligosaccharide preparation, or a combination thereof. In some embodiments, adjusting the level of the oligosaccharide preparation comprises adding additional oligosaccharide preparation into the nutritional composition or removing a portion of the oligosaccharide preparation from the nutritional composition. In some embodiments, adjusting the level of the oligosaccharide preparation comprises adding additional base nutritional composition into the nutritional composition or removing a portion of the base nutritional composition from the nutritional composition. In some particular embodiments, adjusting the level of the oligosaccharide preparation comprises adding additional oligosaccharide preparation into the nutritional composition.

EXAMPLES

Example 1: Synthesis of a Gluco-Galacto-Oligosaccharide Preparation

Synthesis of a gluco-galacto-oligosaccharide preparation was performed in a three-liter reaction vessel using catalyst loadings, reaction times, and reaction temperatures that were selected to enable suitable production at the kg scale.

D-glucose monohydrate (825.16 g), D-lactose monohydrate (263.48 g) and 2-pyridinesulfonic acid (1.0079 g, Sigma-Aldrich, St. Louis, US) were added to a three-liter, three-neck round bottom flask with a center 29/42 ground glass joint and two 24/40 side ground glass joints. A 133 mm Teflon stirring blade was affixed to a glass stir shaft using PTFE tape. The stir rod was secured through the center point using a Teflon bearing adapter and attached to an overhead high-torque mechanical mixer via flexible coupler. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction mixture reached 120° C., the reflux condenser was repositioned into a distillation configuration, with the distillated collected in a 250 mL round bottom flask placed in an ice bath. The mixture was maintained at 130° C. with continuous mixing for 6 hours, after which the thermocouple box was powered off. The distillation apparatus was removed and 390 g of 60° C. distilled water was gradually added into the three-neck flask. The resulting mixture was left to stir at 40 RPM for 10 hours. Approximately 1,250 g of a viscous, light-amber material was collected and measured by refractive index to have a concentration of 71.6 Brix.

Example 2: Synthesis of a Gluco-Oligosaccharide Preparation

Synthesis of a gluco-oligosaccharide preparation was performed in a three-liter reaction vessel using catalyst loadings, reaction times, and reaction temperatures that were selected to enable suitable production at the kg scale.

D-glucose monohydrate (1,150 g) was added to a three-liter, three-neck round bottom flask with one center 29/42 ground glass joint and two side 24/40 ground glass joints. A 133 mm Teflon stirring blade was affixed to glass stir shaft using PTFE tape. The stir rod was secured through the center port of the flask using a Teflon bearing adapter and attached to an overhead high-torque mechanical mixer via flex coupling. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction temperature increased to between 120° C. and 130° C., (+)-Camphor-10-sulfonic acid (1.16 g, Sigma-Aldrich, St. Louis) was added to the three-neck flask and the apparatus was switched from a reflux condenser to a distillation configuration with a round bottom collection flask placed in an ice bath. This setup was maintained for 1 and a half hours, after which the thermocouple box was powered off, the distillation apparatus was removed, and 390 g of 23° C. distilled water was gradually added into the three-neck flask. The resulting mixture was left to stir at 40 rpm for 10 hours until the moment of collection. Approximately 1300 g of a viscous, dark-amber material was collected and measured to have a concentration of 72.6 brix.

Example 3: Synthesis of a Gluco-Galacto-Manno-Oligosaccharide Preparation

Synthesis of a gluco-galacto-manno-oligosaccharide preparation was performed in a three-liter reaction vessel using catalyst loadings, reaction times, and reaction temperatures that were selected to enable suitable production at the kg scale. MH47-32-A/MH46-35-B: 8/10/18

The gluco-galacto-manno-oligosaccharide preparation was prepared as two separate components synthesized in separate reaction vessels that were independently collected. Each synthesis used different starting reactants but followed the same procedure and methods to completion. The final gluco-galacto-manno-oligosaccharide preparation was a homogeneous syrup formed from the mixing of both synthesis products.

For the synthesis of the first component, 990.54 g of glucose monohydrate, 105.58 g of lactose monohydrate and 1.00 g of 2-pyridinesulfonic acid were added to a three-liter, three-neck round bottom flask with one center 29/42 ground joint flanked by two 24/40 ground joints. A 133 mm Teflon stirring blade was affixed to a 440 mm glass stir shaft using PTFE tape. The stir rod was secured through the center point using a Teflon bearing adapter and attached to an overhead high-torque mechanical mixer via flexible coupler. The flask was placed inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120 C and 130 C was observed, the apparatus was switched from a reflux condenser to a distillation configuration with a round bottom collection flask placed in an ice bath. This setup was maintained for approximately 6 hours and 10 minutes, after which the heating mantle was powered off, the distillation apparatus was removed, and 390 g of 60° C. distilled water was gradually added into the three-neck flask. The resulting mixture was left to stir at 40 rpm for 10 hours until the moment of collection. Approximately 1250 g of a viscous, light-amber material was collected and measured by refractive index to have a concentration of 73.1 Brix.

For the synthesis of the second component, 825.04 g of glucose monohydrate, 251.16 g of pure mannose from wood, 25.10 g distilled water, and 1.00 g of 2-pyridinesulfonic acid were added to a three-liter, three-neck round bottom flask with one center 29/42 ground joint flanked by two 24/40 ground joints. The remainder of the second component's synthesis followed the same procedure and methods as those of the first, until the moment of collection. Approximately 1250 g of a viscous, dark-amber material was collected and measured to have a concentration of 72.3 brix.

The entirety of the first and second components were transferred into a suitably sized HDPE container and mixed thoroughly by hand until homogenous. The final syrup mixture was approximately 2.5 kg, dark-amber in color, viscous and was measured to have a concentration of approximately 72 brix.

Example 4: Synthesis of a Gluco-Manno-Oligosaccharide Preparation

Synthesis of a gluco-oligosaccharide preparation was performed in a three-liter reaction vessel using catalyst loadings, reaction times, and reaction temperatures that were selected to enable suitable production at the kg scale.

A gluco-manno-oligosaccharide preparation was prepared as two separate components synthesized in separate reaction vessels that were independently collected. Each synthesis used different starting reactants but followed the same procedure and methods to completion. The final gluco-manno-oligosaccharide preparation was a homogeneous syrup formed from the mixing of both synthesis products.

For the synthesis of the first component, 1264.80 g of glucose monohydrate was added to a three-liter, three-neck round bottom flask with one center 29/42 ground joint flanked by two 24/40 ground joints. A 133 mm Teflon stirring blade was affixed to a 440 mm glass stir shaft using PTFE tape. The stir rod was secured through the center point using a Teflon bearing adapter and attached to an overhead high-torque mechanical mixer via flexible coupler. The flask was placed inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120° C. and 130° C. was observed, 1.15 g of (+)-camphor-10-sulfonic acid was added to the three-neck flask and the apparatus was switched from a reflux condenser to a distillation configuration with a round bottom collection flask placed in an ice bath. This setup was maintained for approximately 1 hour, after which the thermocouple box was powered off, the distillation apparatus was removed, and 390 g of 23° C. distilled water was gradually added into the three-neck flask. The resulting mixture was left to stir at 40 rpm for 10 hours until the moment of collection. Approximately 1350 g of a viscous, light-amber material was collected and measured to have a concentration of 71.8 brix.

For the synthesis of the second component, 949.00 g of glucose monohydrate, 288.00 g of pure mannose from wood, 27.94 g distilled water, and 1.15 g of 2-pyridinesulfonic acid were added to a three-liter, three-neck round bottom flask with one center 29/42 ground joint flanked by two 24/40 ground joints. The remainder of the second component's synthesis followed the same procedure and methods as those of the first until the moment of collection, except (+)-camphor-10-sulfonic acid was not added as the reflux condenser was switched to a distillation configuration and the resulting setup was maintained for approximately 6 hours. Approximately 1350 g of a viscous, dark-amber material was collected and measured to have a concentration of 72.0 brix.

The entirety of the first and second components were transferred into a suitably sized HDPE container and mixed thoroughly by hand until homogenous. The final syrup mixture was approximately 2.7 kg, dark-amber in color, viscous and was measured by refractive index to have a concentration of approximately 72 Brix.

Example 5: Synthesis of a Gluco-Manno-Oligosaccharide Preparation

Kilogram scale production of the oligosaccharide preparation was performed in a three-liter reaction vessel using catalyst loadings, reaction times, and reaction temperatures found to be suitable for production at the 1 kg scale.

A gluco-manno-oligosaccharide preparation was prepared as two separate components synthesized in separate reaction vessels that were independently collected. Each synthesis used different starting reactants but followed the same procedure and methods to completion. The final gluco-manno-oligosaccharide preparation was a homogeneous syrup formed from the mixing of both synthesis products.

For the synthesis of the first component, 1261.00 g of glucose monohydrate and 1.15 g of 2-pyridinesulfonic acid were added to a three-liter, three-neck round bottom flask with one center 29/42 ground joint flanked by two 24/40 ground joints. A 133 mm Teflon stirring blade was affixed to a 440 mm glass stir shaft using PTFE tape. The stir rod was secured through the center point using a Teflon bearing adapter and attached to an overhead high-torque mechanical mixer via flexible coupler. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120° C. and 130° C. was observed, the apparatus was switched from a reflux condenser to a distillation configuration with a round bottom collection flask placed in an ice bath. This setup was maintained for approximately 6 hours, after which the thermocouple box was powered off, the distillation apparatus was removed, and 390 g of 23° C. distilled water was gradually added into the three-neck flask. The resulting mixture was left to stir at 40 rpm for 10 hours until the moment of collection. Approximately 1250 g of a viscous, light-amber material was collected and measured to have a concentration of 73.5 brix.

For the synthesis of the second component, 949.00 g of glucose monohydrate, 288.00 g of pure mannose from wood, 28.94 g distilled water, and 1.15 g of 2-pyridinesulfonic acid were added to a three-liter, three-neck round bottom flask with one center 29/42 ground joint flanked by two 24/40 ground joints. The remainder of the second component's synthesis followed the same procedure and methods as those of the first until the moment of collection. Approximately 1250 g of a viscous, dark-amber material was collected and measured to have a concentration of 73.3 brix.

The entirety of the first and second components were transferred into a suitably sized HDPE container and mixed thoroughly by hand until homogenous. The final syrup mixture was approximately 2.5 kg, dark-amber in color, viscous and was measured to have a concentration of approximately 73 brix.

Example 6: Synthesis of a Gluco-Galacto-Oligosaccharide Preparation

Kilogram scale production of the oligosaccharide preparation was performed in a three-liter reaction vessel using catalyst loadings, reaction times, and reaction temperatures found to be suitable for production at the 1 kg scale.

A 3 L three-neck flask was equipped with an overhead mixer connected via a 10 mm diameter glass stir-shaft to a 14 cm crescent-shaped mixing element. The mixing element was positioned with approximately 5 mm clearance from the walls of the flask. The flask was heated via a hemispherical electric heating mantle powered by a temperature control unit connected to a wand-type thermocouple probe inserted into the reaction flask. The thermocouple probe was placed to provide 5-10 mm clearance above the mixing element. The flask was charged with 576 grams of food-grade dextrose monohydrate and 577 grams of food-grade D-galactose monohydrate and heated to approximately 115° C. to obtain a molten sugar syrup. Once the syrup was obtained, the flask was fitted with a jacketed reflux condenser cooled to 4° C. by circulating chilled glycol/water and the temperature. 31 grams of Dowex Marathon C (moisture content 0.48 g H$_2$O/g resin) were added to the mixture to form a stirred suspension. The condenser was repositioned into distillation configuration and the suspension was heated to 145° C.

A mixing rate of approximately 80 RPM and a temperature of 145° C. was maintained for 3.8 hours, after which the set point on the temperature control unit was reduced to 80° C. and 119 mL of 60° C. deionized water was gradually added to the flask to obtain a dark amber syrup containing residual Dowex resin. The resulting suspension was further diluted to 60 Brix, cooled to room temperature and vacuum filtered through a 0.45 micron filter to remove the resin. 1,200 grams of light-amber syrup at 60 Brix concentration was obtained.

Example 7: Synthesis of a Gluco-Oligosaccharide Preparation

Kilogram scale production of the oligosaccharide preparation was performed in a three-liter reaction vessel using catalyst loadings, reaction times, and reaction temperatures found to be suitable for production at the 1 kg scale.

A 3 L three-neck flask was equipped with an overhead mixer connected via a 10 mm diameter glass stir-shaft to a 14 cm crescent-shaped mixing element. The mixing element was positioned with approximately 5 mm clearance from the walls of the flask. The flask was heated via a hemispherical electric heating mantle powered by a temperature control unit connected to a wand-type thermocouple probe inserted into the reaction flask. The thermocouple probe was placed to provide 5-10 mm clearance above the mixing element. The flask was gradually charged with 1,148 grams of food-grade dextrose monohydrate and heated to approximately 115° C. to obtain a molten sugar syrup. Once the syrup was obtained, the flask was fitted with a jacketed distillation condenser cooled to 4° C. by circulating chilled glycol/water. The reaction temperature was gradually increased to 145° C. Once the temperature was obtained and stable, 31 grams of Dowex Marathon C (moisture content 0.48 g H$_2$O/g resin) was added to the mixture and a mixing rate of approximately 80 RPM and a temperature of 145° C. was maintained for 3.8 hours.

After 3.8 hours, the set point on the temperature control unit was reduced to 80° C. and 119 mL of 60° C. deionized water was gradually added to the flask to obtain a dark amber syrup containing residual Dowex resin. The resulting suspension was further diluted to 60 Brix, cooled to room temperature and vacuum filtered through a 0.45 micron filter to remove the resin. 1,113 grams of dark-amber gluco-oligosaccharide syrup at 60 Brix concentration was obtained.

Example 8: Single-Pot Syntheses of Oligosaccharide Preparations

A single pot (single component) synthesis of the oligosaccharide from Example 3 was demonstrated at 300 gram scale in a one-liter reaction vessel using catalyst loadings, reaction times, and reaction temperatures found to be suitable for the single pot reaction.

272.30 g of food-grade D-glucose monohydrate from corn, 37.50 g of fodo grade D-mannose from wood, 15.60 g of food-grade D-lactose monohydrate, 3.96 g of distilled water and 0.270 g of 2-pyridinesulfonic acid (Sigma-Aldrich, St. Louis) were added to a one-liter, three-neck round bottom flask with one center 29/42 ground joint flanked by two 24/40 ground joints. A Teflon stirring blade was affixed to a 220 mm glass stir shaft using PTFE tape. The stir rod was secured through the center point using a Teflon bearing adapter and attached to an overhead high-torque mechanical mixer via flexible coupler. The flask was secured inside a hemispherical electric heating mantle operated by a temperature control unit via a J-type wand thermocouple inserted through a rubber septum in one of the side ports. The tip of the thermocouple was adjusted to reside within the reaction mixture with several mm clearance above the mixing element. A secondary temperature probe connected to an auxiliary temperature monitor was also inserted and secured by the same means. The second side port of the flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. Once a temperature control box reading between 120 C and 130 C was observed, the apparatus was switched from a reflux condenser to a distillation configuration with a round bottom collection flask placed in an ice bath. The mixture was maintained at 130° C. with continuous stirring for approximately 5 hours and 40 minutes, after which the heating mantle and distillation apparatus was removed. Approximately 40 g of 23° C. distilled water was gradually added into the three-neck flask. The resulting mixture was left to stir at 40 rpm for 10 hours until the moment of collection. Approximately 389 g of a viscous, dark-amber material was collected and measured to have a concentration of 67.0 brix. Consistency with the oligosaccharide preparation from Example 3 was confirmed by SEC chromatography and 2D $^1$H, $^{13}$C-HSQC NMR spectroscopy.

Example 9: Characterization of Oligosaccharide Preparations

The methods and procedures from Examples 1-8 were used to prepare replicate batches and blends of the oligosaccharides of Examples 1-7. The resulting materials were analyzed by HPLC Size Exclusion Chromatography (SEC) to characterize the molecular weight distribution, LC-MS/MS analysis to quantify the DP2 anhydrosugar content, and 2D $^1$H, $^{13}$C-HSQC NMR to fingerprint the molecular structure of the corresponding oligosaccharide preparations.

Example 9.1: eleven batches of the oligosaccharide preparation from Example 1 were prepared and blended into four separate lots to produce oligosaccharide preparation 9.1.

Example 9.2: seven batches of the oligosaccharide preparation from Example 2 were prepared and blended into two separate lots to produce oligosaccharide preparation 9.2.

Example 9.3: twelve batches of the oligosaccharide preparation from Example 3 were prepared and blended into five separate lots to produce oligosaccharide preparation 9.3.

Example 9.4: four batches of the oligosaccharide preparation from Example 4 were prepared and blended into a single lot to produce oligosaccharide preparation 9.4.

Example 9.5: four batches of the oligosaccharide preparation from Example 5 were prepared and blended into a single lot to produce oligosaccharide preparation 9.5.

Example 9.6: two batches of the oligosaccharide preparation from Example 6 were prepared and blended into a single lot to produce oligosaccharide preparation 9.6.

Example 9.7: two batches of the oligosaccharide preparation from Example 7 were prepared and blended into a single lot to produce oligosaccharide preparation 9.7.

In the batches of Examples 9.1-9.7, both multi-pot (multi-component) and single-pot variants of the respective synthetic schemes were employed.

Further structural variants of oligosaccharide preparations of Examples 1-7 were synthesized at 300 gram scale using the methods of Examples 1-7 but varying the starting sugar compositions, acid, acid loading, time, and reaction temperature. Oligosaccharide preparations were synthesized as follows:

Example 9.8: 300 grams of sucrose, 3 grams of phosphoric acid, and 27 grams of water were reacted at 125° C. for about one hour to obtain a dark brown oligosaccharide syrup that was then diluted to 60 Brix with distilled water.

Example 9.9: 270 grams of glucose, 30 grams of sucrose, 0.3 grams of phenylphosphonic acid, and 27 grams of water were reacted at 130° C. for between one to four hours to obtain a dark brown oligosaccharide syrup that was then diluted to 60 Brix with distilled water.

Example 9.10: 225 grams of glucose, 75 grams of lactose, 3 grams of butylphosphonic acid and 27 grams of water were reacted at 130° C. for between one to four hours to obtain a dark amber oligosaccharide syrup that was then diluted to 60 Brix with distilled water.

Example 9.11: 225 grams of glucose, 75 grams of lactose, 3 grams of phenylphosphonic acid and 27 grams of water were reacted at 130° C. for between one to five hours to obtain a dark amber oligosaccharide syrup that was then diluted to 60 Brix with distilled water.

Example 9.12: 270 grams of glucose, 30 grams of lactose, 3 grams of phenylphosphinic acid and 27 grams of water were reacted at 130° C. for between three to five hours to obtain a dark brown oligosaccharide syrup that was then diluted to 60 Brix with distilled water.

Example 9.13: 300 grams of glucose, 3 grams of phenylphosphinic acid, and 27 grams of water were reacted at 130° C. for one to three hours to obtain a dark amber oligosaccharide syrup that was then diluted to 60 Brix with distilled water.

Example 9.14: 300 grams of glucose, 2 grams of propionic acid, and 27 grams of water were reacted at 130° C. for one to four hours to obtain an amber oligosaccharide syrup that was then diluted to 60 Brix with distilled water.

Example 9.15: 300 grams of glucose, 0.15 grams of 8-hydroxy-5-quinolinesulfonic acid hydrate, and 27 grams of water were reacted at 130° C. for two to four hours to obtain an amber oligosaccharide syrup that was then diluted to 60 Brix with distilled water.

In the above reactions, all masses refer to the pure component masses, and the total mass of reactant water was inclusive of any carry-along water provided by the moisture content and/or water of hydration of the reactant sugars.

Characterization of Oligosaccharide Preparations:

The resulting materials were analyzed by HPLC Size Exclusion Chromatography (SEC) to characterize the molecular weight distribution, LC-MS/MS analysis to quantify the DP2 anhydrosugar content, and 2D $^1$H, $^{13}$C-HSQC NMR to fingerprint the molecular structure of the corresponding oligosaccharide preparations.

Polymer MW Analysis by HPLC:

The number average molecular weight (MWn) and weight-average molecular weight (MWw) of the oligosaccharide preparations of Examples 9.1-9.7 were determined by HPLC. SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight and standard methods from the art were used to determine the various distribution properties from the SEC chromatogram.

TABLE 2

Polymer molecular weight (MW) for oligosaccharide preparations with multiple lots

| Example | MWn (g/mol) | MWw (g/mol) |
|---|---|---|
| Ex. 9.1 | 719 ± 11 | 1,063 ± 23 |
| Ex. 9.2 | 808 ± 30 | 1,336 ± 122 |
| Ex. 9.3 | 757 ± 15 | 1,186 ± 49 |
| Ex. 9.4 | 761 | 1,196 |
| Ex. 9.5 | 755 | 1,177 |
| Ex. 9.6 | 505 | 709 |
| Ex. 9.7 | 762 ± 12 | 1,154 ± 14 |

Anhydro-DP2 Content Analysis by LC-MS/MS:

The anhydro DP2 content of oligosaccharide preparations was determined by LC-MS/MS using a Capcell Pak NH2 (Shiseido; 250×4.6 mm, 5 μm) column at a flowrate of 1 mL/min under isocratic conditions of water/acetonitrile 35/65. Prior to MS the flow was split 1:4 and a makeup flow of 50 μL 0.05% $NH_4OH$ was added to enhance ionization. For MS detection ESI probe was used in negative mode and MRM method allowed targeted analysis.

The anhydro DP2 contents of the oligosaccharide preparations was first determined relative to that of the oligosaccharide preparation of Example 9.7 as a reference composition. The absolute anhydro DP2 content of the reference oligosaccharide preparation of Example 9.7 was then determined by HPLC-MS/MS to be about 10% and the anhydro DP2 contents of the oligosaccharide preparations of Examples 9.1 to 9.6 were then obtained by calculation. The relative and absolute DP2 contents were determined as follows:

TABLE 3

Anhydro DP2 content for oligosaccharide preparations with multiple lots

| Example | Relative Anhydro DP2 Content Compared to Ex. 9.7 (% Relative to Ex 9.7) | Anhydro DP2 Content (g Anhydro DP2/g total DP2) |
|---|---|---|
| Ex. 9.1 | 53% | 5.3% |
| Ex. 9.2 | 14% | 1.4% |
| Ex. 9.3 | 57% | 5.7% |
| Ex. 9.4 | 53% | 5.3% |
| Ex. 9.5 | 33% | 3.3% |
| Ex. 9.6 | 50% | 5.0% |
| Ex. 9.7 | 100% | 10.0% |

Molecular Fingerprint by 2D $^1H$, $^{13}C$-HSQC NMR:

The molecular structures of the oligosaccharide preparations of Example 9 were characterized by 2D $^1H$, $^{13}C$-HSQC NMR spectroscopy. Samples were prepared by drying 125 mg (dry solids basis) of the oligosaccharide preparation at 40° C. and re-dissolving in D2O containing 0.1% acetone. NMR spectra were acquired at 300K on either a Bruker Avance NMR spectrometer operating at a proton frequency of 400 MHz or on a Bruker Avance III NMR spectrometer operating at a proton frequency of 600 MHz equipped with a cryogenically cooled 5 mm TCI probe. FIG. 1 provides an illustrative 2D $^1H$, $^{13}C$ HSQC NMR spectrum of the oligosaccharide preparation of Example 9.7.

The anomeric region of the $^1H$, $^{13}C$-HSQC spectrum, F2 ($\delta^1H$)=4.2-6.0 ppm and F1($\delta^{13}C$)=90-120 ppm, was used to fingerprint the linkage distribution of the oligosaccharide preparations. Each peak in the anomeric region was integrated and its relative abundance was determined relative to that of the total anomeric region. 2D $^1H$, $^{13}C$ HSQC fingerprinting was performed on the four lots of the oligosaccharide preparation of Example 9.1, resulting in the following relative abundances provided in Table 4.

TABLE 4

Relative abundance of 2D $^1H$, $^{13}C$ HSQC NMR peaks of oligosaccharide preparation of Example 9.1

| F2 (ppm) | F1 (ppm) | AUC (Average ± SEM) |
|---|---|---|
| 5.43 | 92.42 | 0.4% ± 0.3% |
| 5.44 | 102.07 | 0.4% ± 0.1% |
| 5.43 | 90.05 | 0.5% ± 0.2% |
| 5.40 | 100.22 | 1.6% ± 0.4% |
| 5.37 | 98.33 | 0.7% ± 0.4% |
| 5.35 | 99.70 | 2.7% ± 0.6% |
| 5.33 | 96.53 | 0.3% ± 0.2% |
| 5.24 | 100.86 | 0.5% ± 0.2% |
| 5.22 | 92.71 | 20.2% ± 3.9% |
| 5.21 | 102.45 | 0.5% ± 0.4% |
| 5.18 | 93.86 | 0.9% ± 0.4% |
| 5.17 | 96.01 | 0.4% ± 0.1% |
| 5.09 | 96.88 | 0.6% ± 0.3% |
| 5.03 | 108.49 | 0.4% ± 0.2% |
| 5.02 | 109.16 | 0.4% ± 0.4% |
| 4.98 | 99.19 | 0.6% ± 0.3% |
| 4.95 | 98.51 | 30.6% ± 4.1% |
| 4.86 | 98.53 | 0.7% ± 0.5% |
| 4.79 | 96.84 | 0.6% ± 0.3% |
| 4.71 | 103.48 | 2.5% ± 0.7% |
| 4.64 | 103.56 | 0.8% ± 0.4% |
| 4.63 | 102.49 | 0.7% ± 0.5% |
| 4.62 | 104.56 | 1.4% ± 0.4% |
| 4.57 | 97.07 | 1.6% ± 0.3% |
| 4.50 | 103.30 | 25.9% ± 2.2% |
| 4.45 | 103.56 | 2.4% ± 1.3% |

Example 10: Determination of the Anhydro Sugar Subunits of an Oligosaccharide Preparation The relative abundance of anhydro sugar subunits in the oligosaccharide preparations of Example 9 was determined by MALDI-MS on a Bruker Ultraflex instrument. Samples were dissolved in water to a concentration of 10 mg/ml, from which 5 μl were mixed with matrix solution (30 mg/ml DHB in 80% ethanol and water in a ratio 1:10). Plates were prepared by applying 1 μl of the analyte solution to the target plate and dried at ambient air. In some cases, samples were re-crystalized by applying 1 μl ethanol prior to MS analysis.

FIG. 2 provides an illustrative MALDI spectrum of an oligosaccharide preparation from Example 9. Anhydrosugar subunits are clearly observed as offset peaks shifted by −18 g/mol relative to its respective principal DP parent. Offset peaks are observed at all values of DP, indicating that anhydrosugar subunits are detected at all oligosaccharide sizes. The relative intensity of the anhydro subunit peak was determined to be about 10% of the total peak intensity for each DP.

Figure 14A:
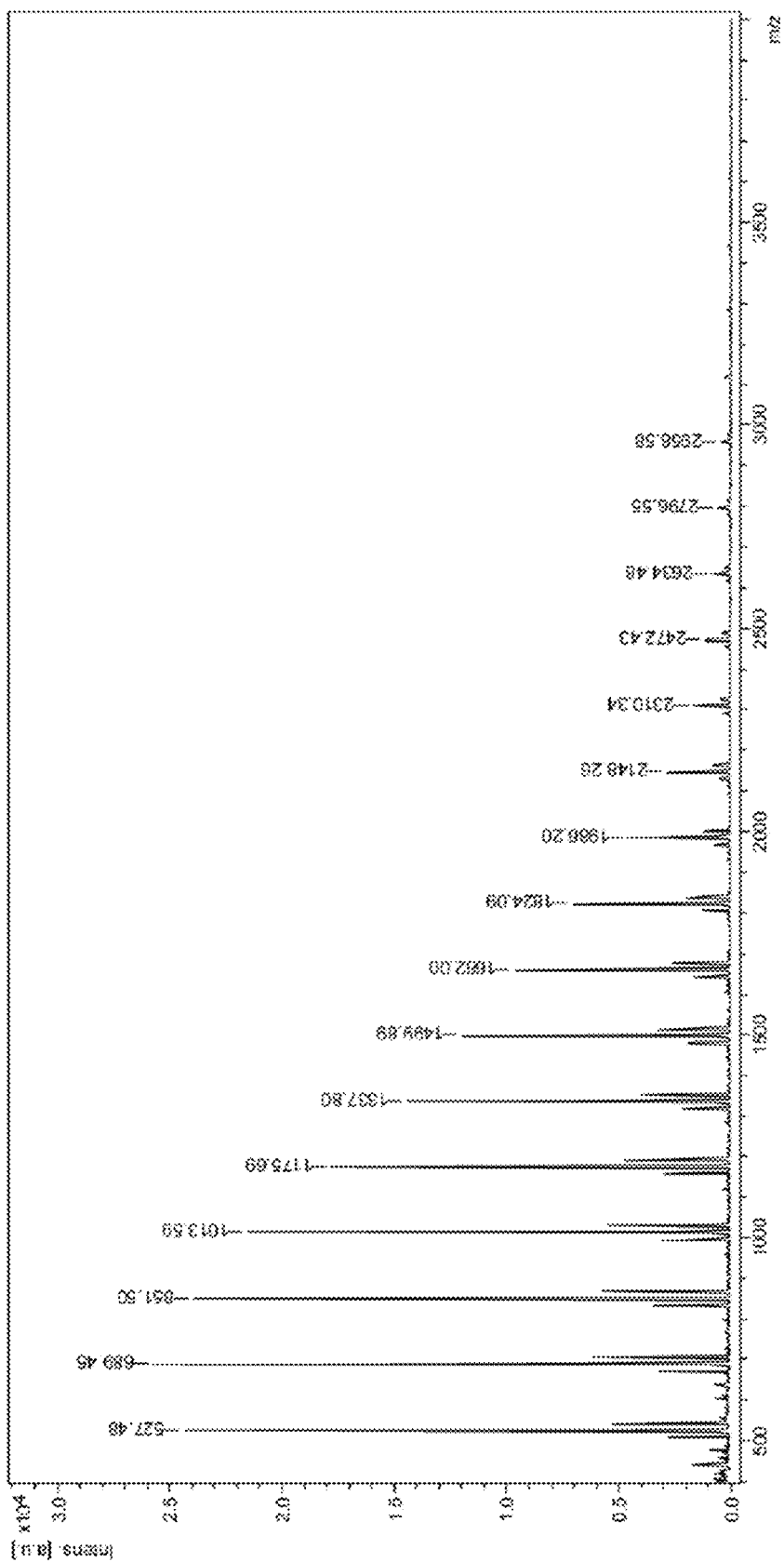
FIG. 14A illustrates a MALDI-MS spectrum of an oligosaccharide preparation from Example 2 that demonstrates the presence of anhydro-subunits.
Figure 14B:
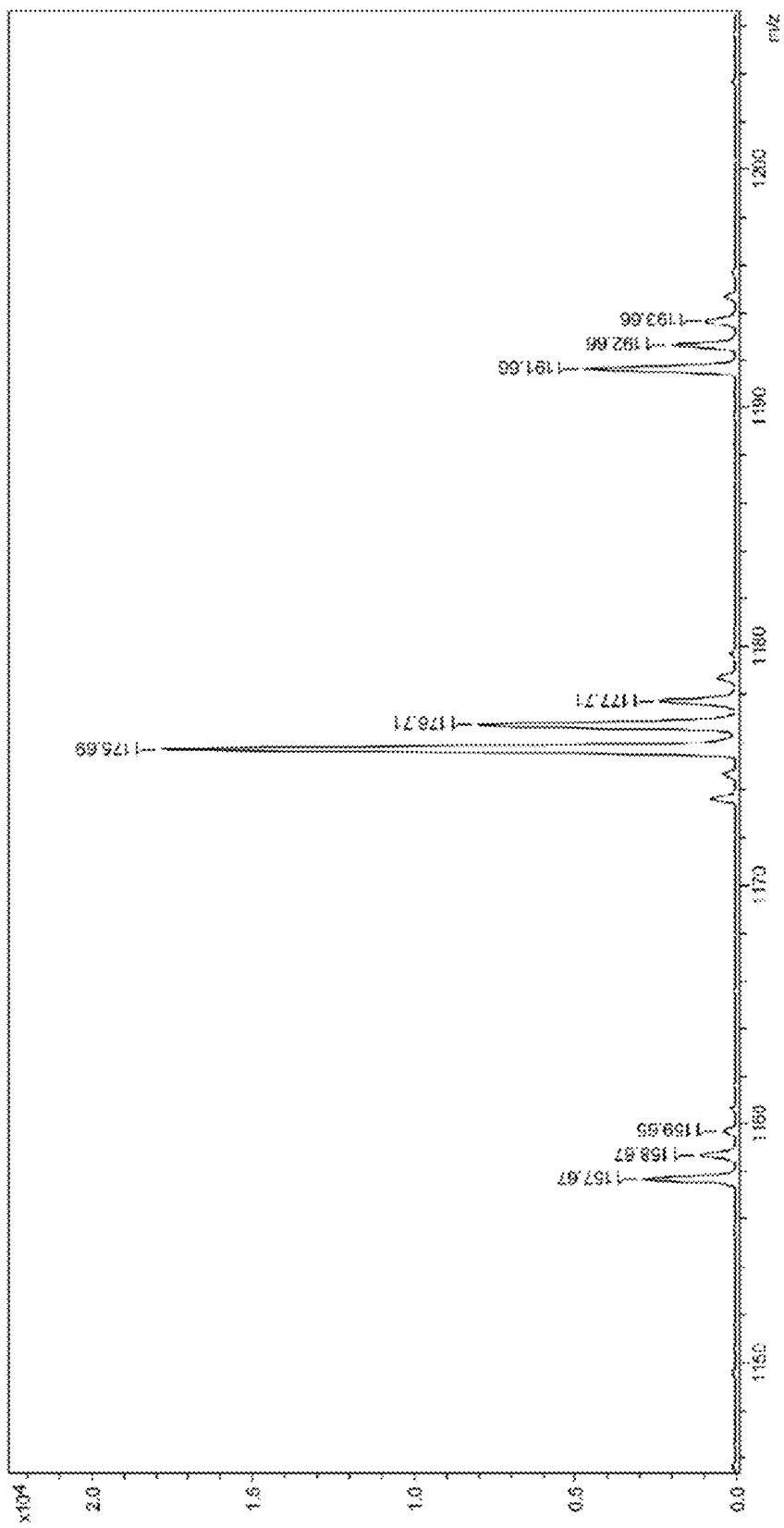
FIG. 14B illustrates an enlargement of a part of the MALDI-MS spectrum shown in FIG. 14A.
Figures 19A, 19B:
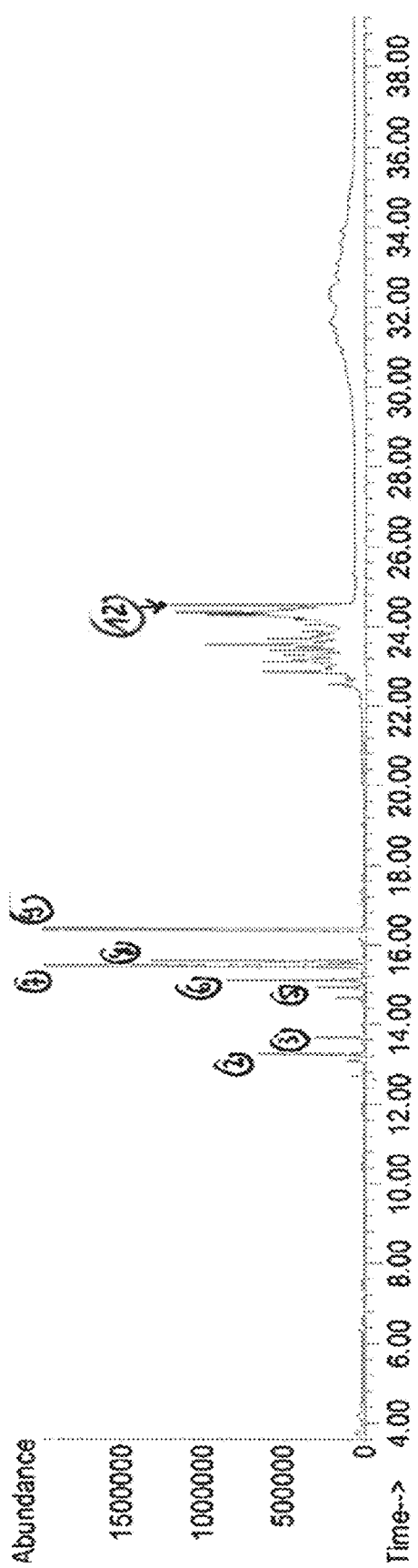
FIG. 19A illustrates GC-MS spectrum detection of the DP1, anhydro DP1, DP2 and anhydro DP2 fractions of an oligosaccharide preparation of Example 1.
FIG. 19B illustrates an enlargement of the DP2 and anhydro DP 2 fractions as shown in FIG. 19A.
Figure 21A:
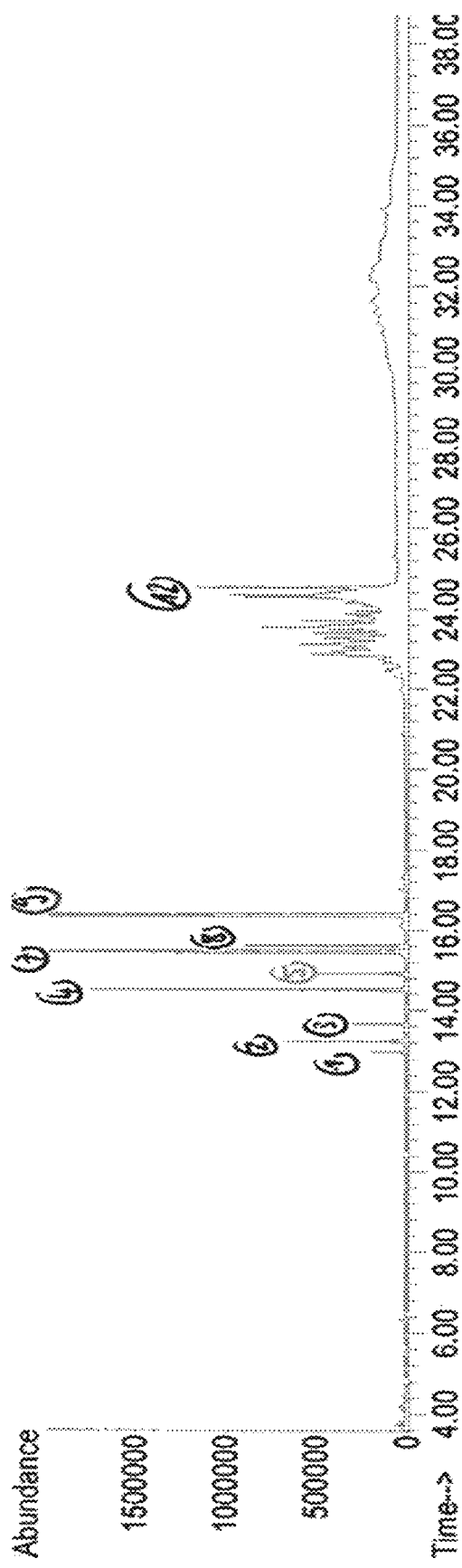
FIG. 21A illustrates GC-MS spectrum detection of the DP1, anhydro DP1, DP2 and anhydro DP2 fractions of an oligosaccharide preparation of Example 4.
Figure 21B:
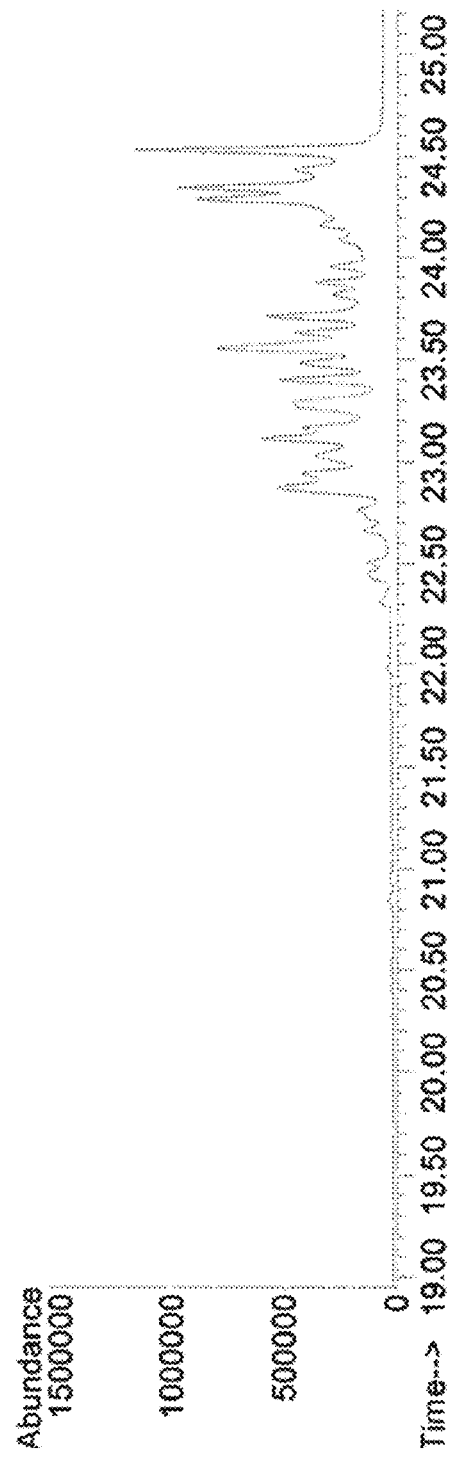
FIG. 21B illustrates an enlargement of the DP2 and anhydro DP 2 fractions as shown in FIG. 21A.
Figure 22A:
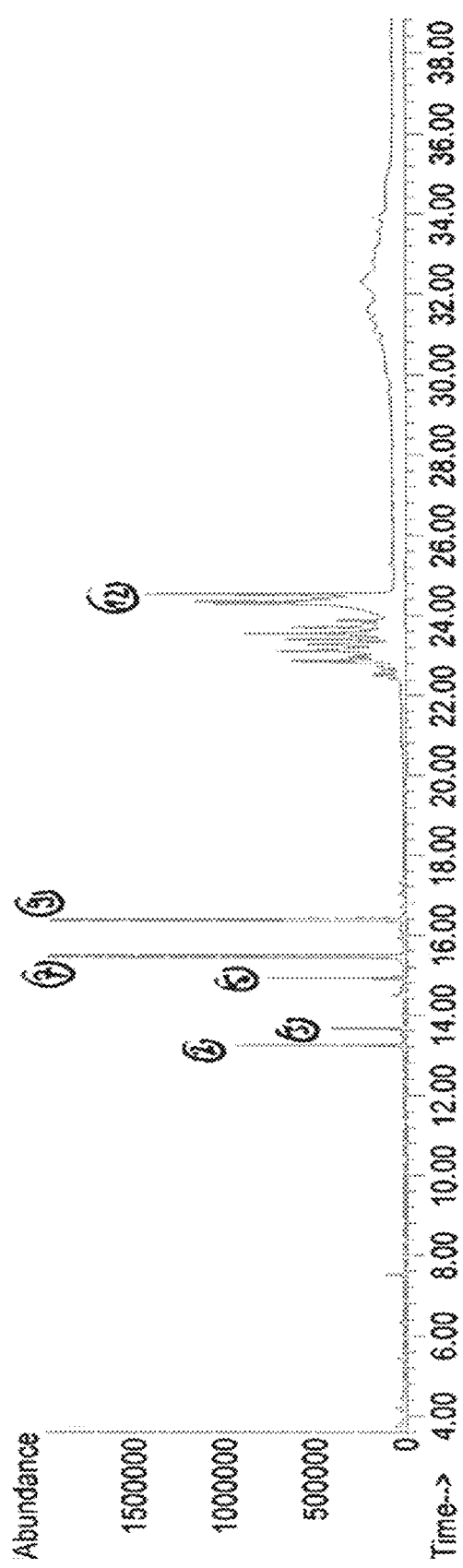
FIG. 22A illustrates GC-MS spectrum detection of the DP1, anhydro DP1, DP2 and anhydro DP2 fractions of an oligosaccharide preparation of Example 7.
Figure 22B:
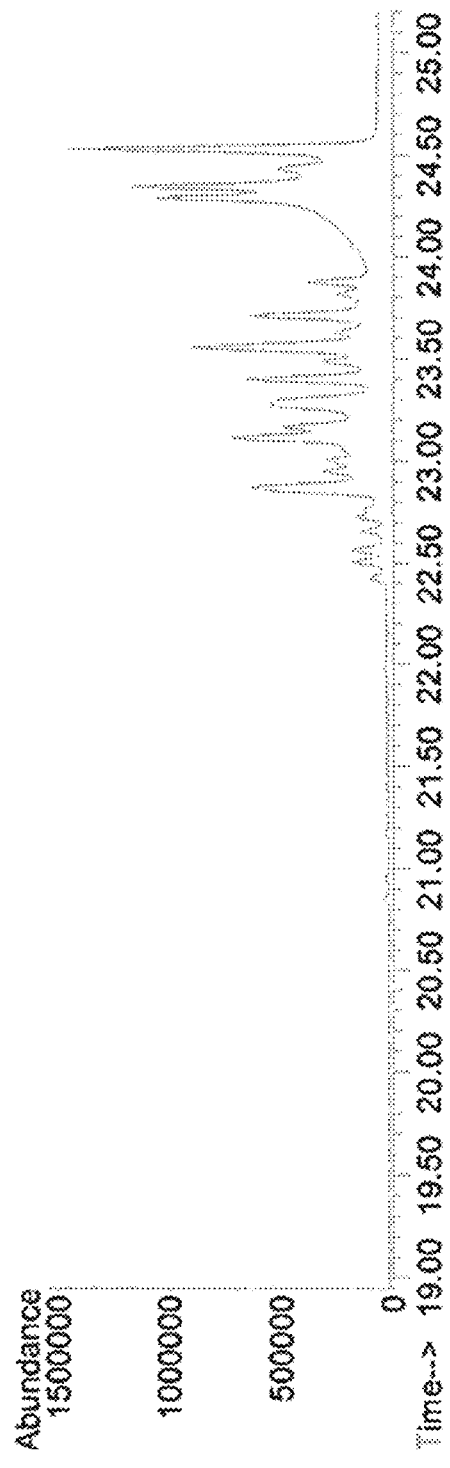
FIG. 22B illustrates an enlargement of the DP2 and anhydro DP 2 fractions as shown in FIG. 22A.

FIG. 14A and FIG. 14B illustrate MALDI spectra of an oligosaccharide preparation from Example 2. Anhydrosugar subunits are observed at every DP level with an relative intensity in the range of 5-10%.

Example 11: Characterization of the Anhydro Sub-Units of an Oligosaccharide Preparation The anhydrosugar subunits of the oligosaccharide preparations of Example 9 were characterized using a combination of LC-MS, GC-MS, LC-MS/MS, and NMR methods.

Figure 3:
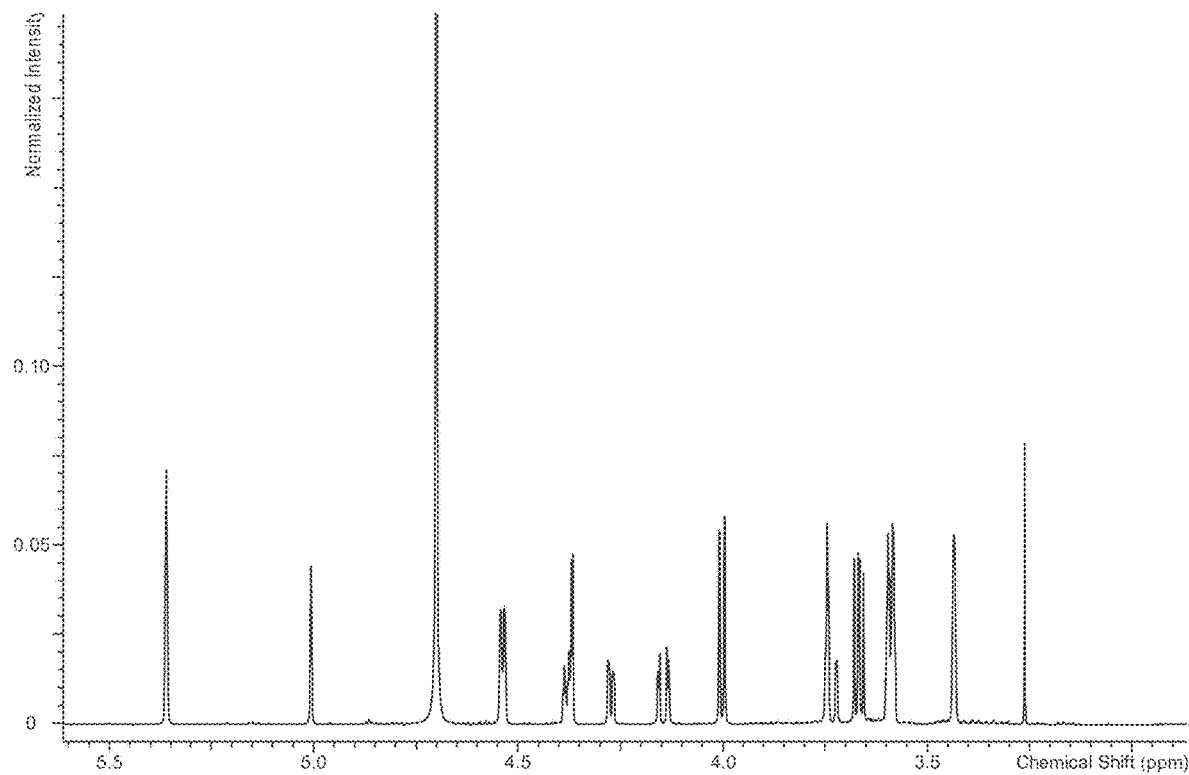
FIG. 3 illustrates a 1D $^1$H-proton NMR spectrum of an anhydro DP1 fraction isolated from an oligosaccharide of Example 9.
Figure 4:
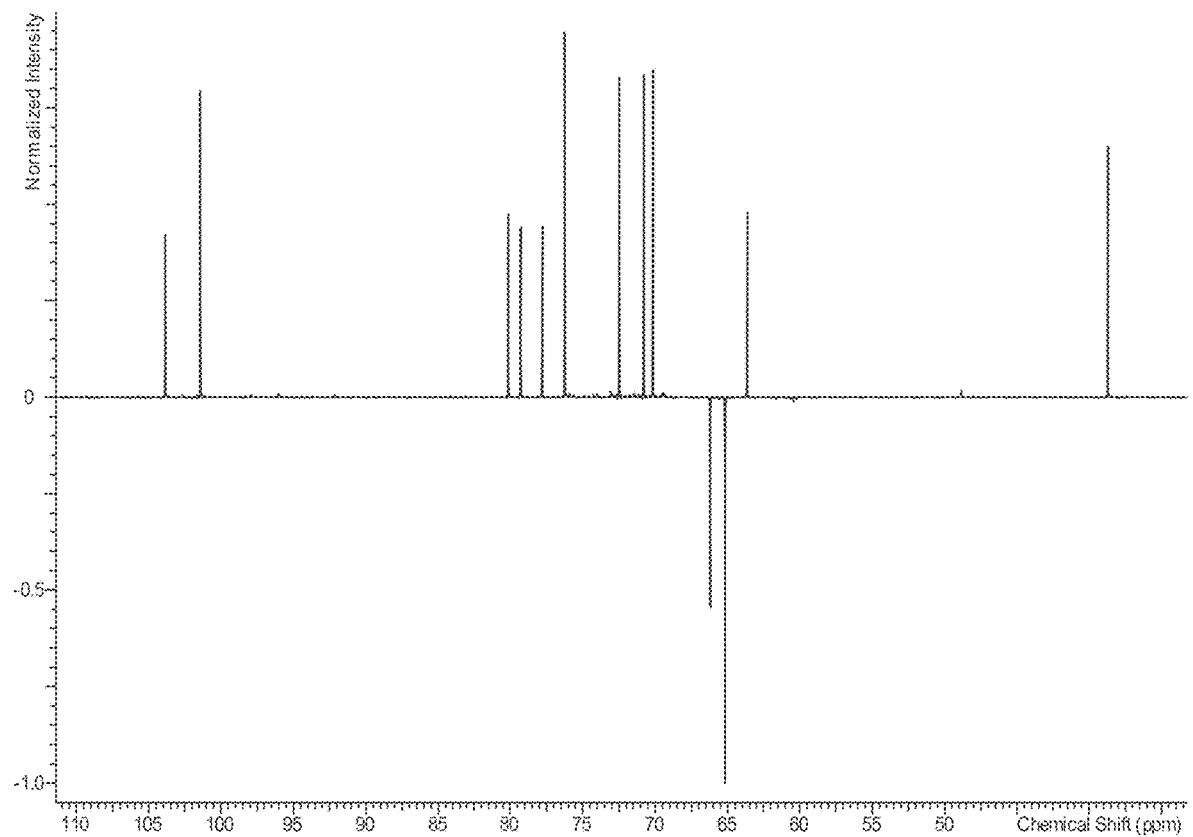
FIG. 4 illustrates a 1D APT $^{13}$C-NMR spectrum of an anhydro DP1 fraction isolated from an oligosaccharide of Example 9.

Characterization of Anhydro-DP1 Components:

The anhydro DP1 component of an oligosaccharide preparation from Example 9 was isolated by preparative liquid chromatography. The isolated anhydro-DP1 component was prepared for NMR by dissolving it in 0.75 mL of D20. FIG. 3 provides an illustrative 1D $^1$H-NMR spectrum of an anhydro DP1 fraction isolated from an oligosaccharide of Example 9 and FIG. 4 provides an illustrative APT $^{13}$C-NMR spectrum of the same isolated anhydro DP1 fraction. The NMR peak assignments are provided in Table 5 and FIG. 5.

TABLE 5

NMR peak assignments

| # | 1,6-anhydro-beta-D-glucofuranose | | 1,6-Anhydro-beta-D-glucopyranose | |
|---|---|---|---|---|
| | $^1$H (ppm) | $^{13}$C (ppm) | $^1$H (ppm) | $^{13}$C (ppm) |
| 1 | 5.33 | 101.9 | 5.01 | 104.4 |
| 2 | 3.40 | 70.6 | 4.37 | 79.8 |
| 3 | 3.56 (ov)$^a$ | 73.0 | 4.27 | 78.3 |
| 4 | 3.56 (ov)$^a$ | 71.3 | 4.38 | 80.6 |
| 5 | 4.50 | 76.7 | 3.74 | 64.1 |
| 6 | 3.97, 3.64 | 65.7 | 4.14, 3.72 | 66.7 |

$^a$Ov stands for overlapped signal

The ratio of 1,6-anhydro-beta-D-glucofuranose to 1,6-Anhydro-beta-D-glucopyranose was determined by NMR to be 2:1.

Example 12: Characterization of the Anhydro Sub-Units of an Oligosaccharide Preparation The anhydrosugar subunits of the oligosaccharide preparations of Example 9 were characterized using a combination of LC-MS, GC-MS, LC-MS/MS, and NMR methods.
Characterization of the Anhydro-DP2 Components The anhydro DP2 content of the oligosaccharide preparations of Example 9 were determined by GC-MS and LC-MS/MS analysis. Gas chromatography was performed using a 30 m×0.25 mm fused silica column containing HP-5MS stationary phase, with 21.57 psi constant pressure Helium as the carrier gas. Aliquots were pre-derivatized by acetylation by dissolving 20 mg of sample in 0.5 mL pyridine with 0.5 mL acetic anhydride for 30 minutes at 60° C. 1 uL samples were injected at 300° C. with an oven temperature program starting at 70° C. and ramping by 10° C. per minute to 315° C. Detection was performed on an Agilent 5975C MSD with an electron energy of 70 eV.

Figure 6:
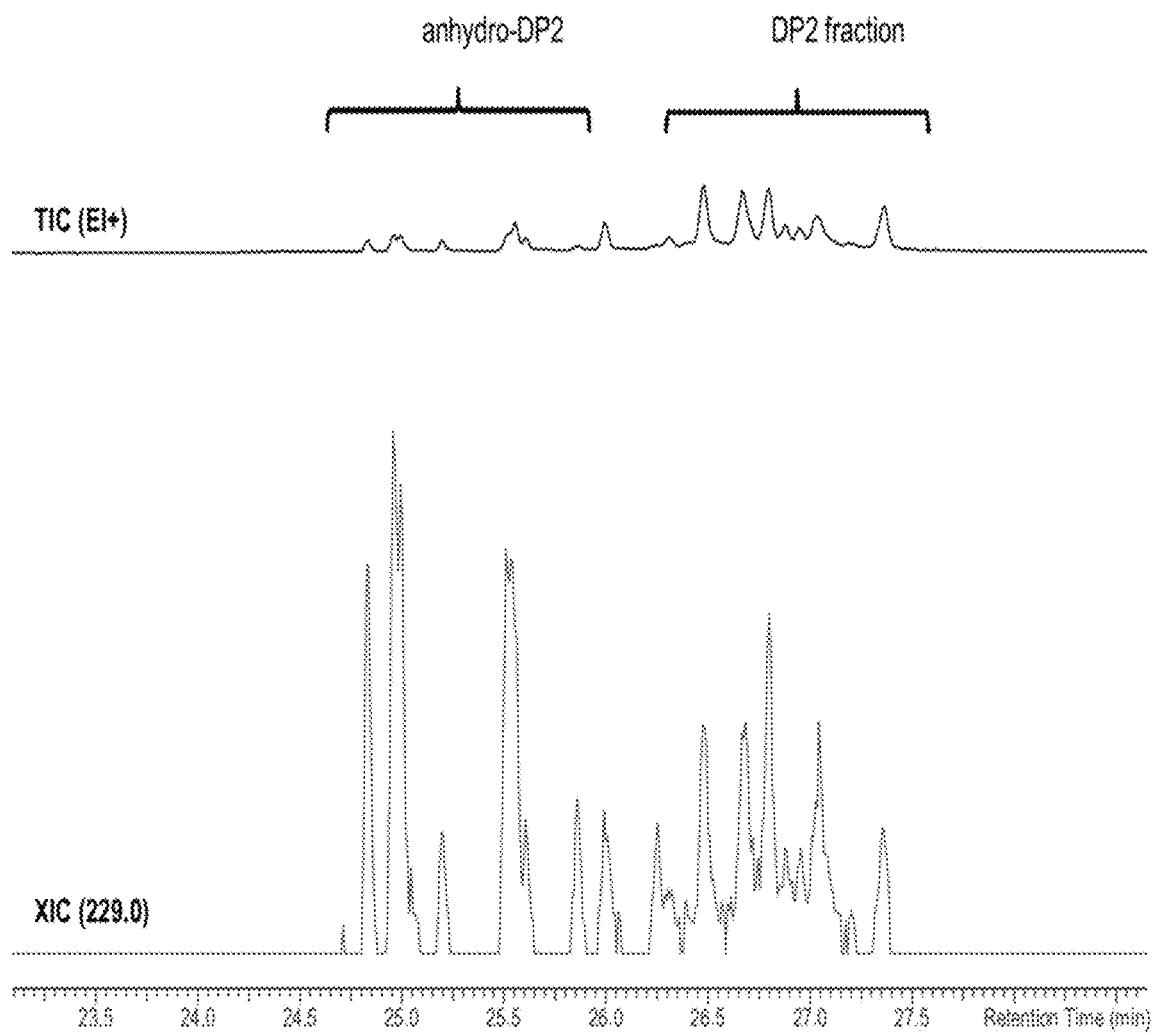
FIG. 6 illustrates an enlargement of the GC-MS chromatogram (TIC and XIC (m/z 229) plots) for the oligosaccharide preparation of Example 9.7 following derivatization.

FIG. 6 illustrates an enlargement of the GC-MS chromatogram for the oligosaccharide preparation of Example 9.7. The TIC and XIC (m/z 229) plots demonstrate that the anhydro-DP2 components elute before the DP2 components.

FIGS. 19A-19B, 20A-20B, 21A-21B, and 22A-22B illustrate the presence of the DP1, anhydro DP1, DP2 and anhydro DP2 fractions as detected by GC-MS in an oligosaccharide preparation of Example 1, Example 3, Example 4, and Example 7, respectively. As shown in FIGS. 19A-19B, 20A-20B, 21A-21B, and 22A-22B, anhydro DP1 and DP1 fractions have a retention time of from about 12-17 minutes, and anhydro DP2 and DP2 fractions have a retention time of about from 22-25 minutes.

Figure 28:
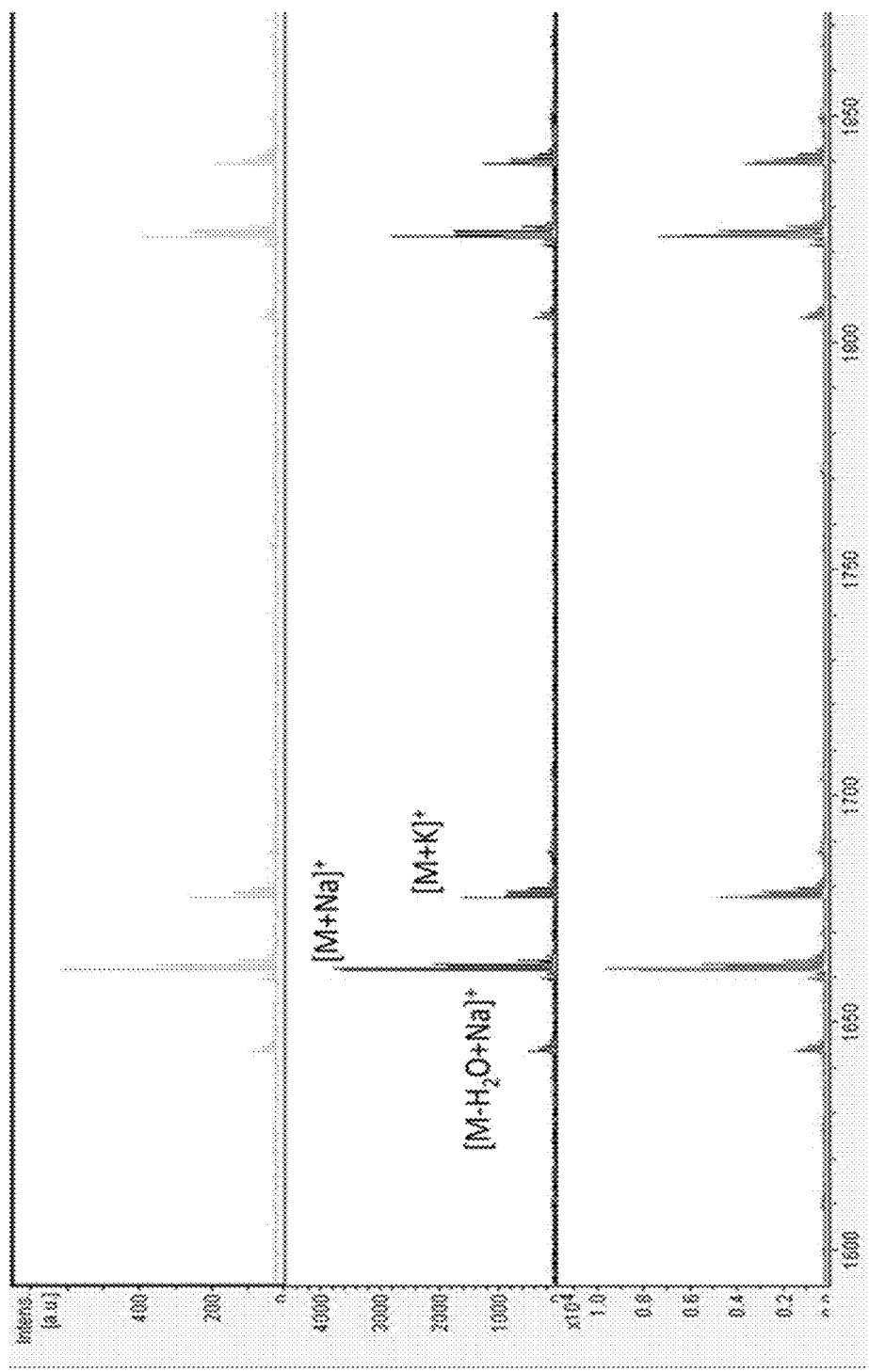
FIG. 28 illustrates MALDI-MS spectra comparing the oligosaccharide preparation from Example 9 at different laser energies.

FIG. 28 illustrates MALDI-MS spectra comparing the oligosaccharide preparation from Example 9 at different laser energies. Relative abundancy of signals were nearly unchanged, demonstrating that no loss of water is introduced by the laser ionisation. Hence, proving the presence of anhydro-sugar subunits in the oligosaccharide preparation.

Example 13: Comparative Example

Figure 7:
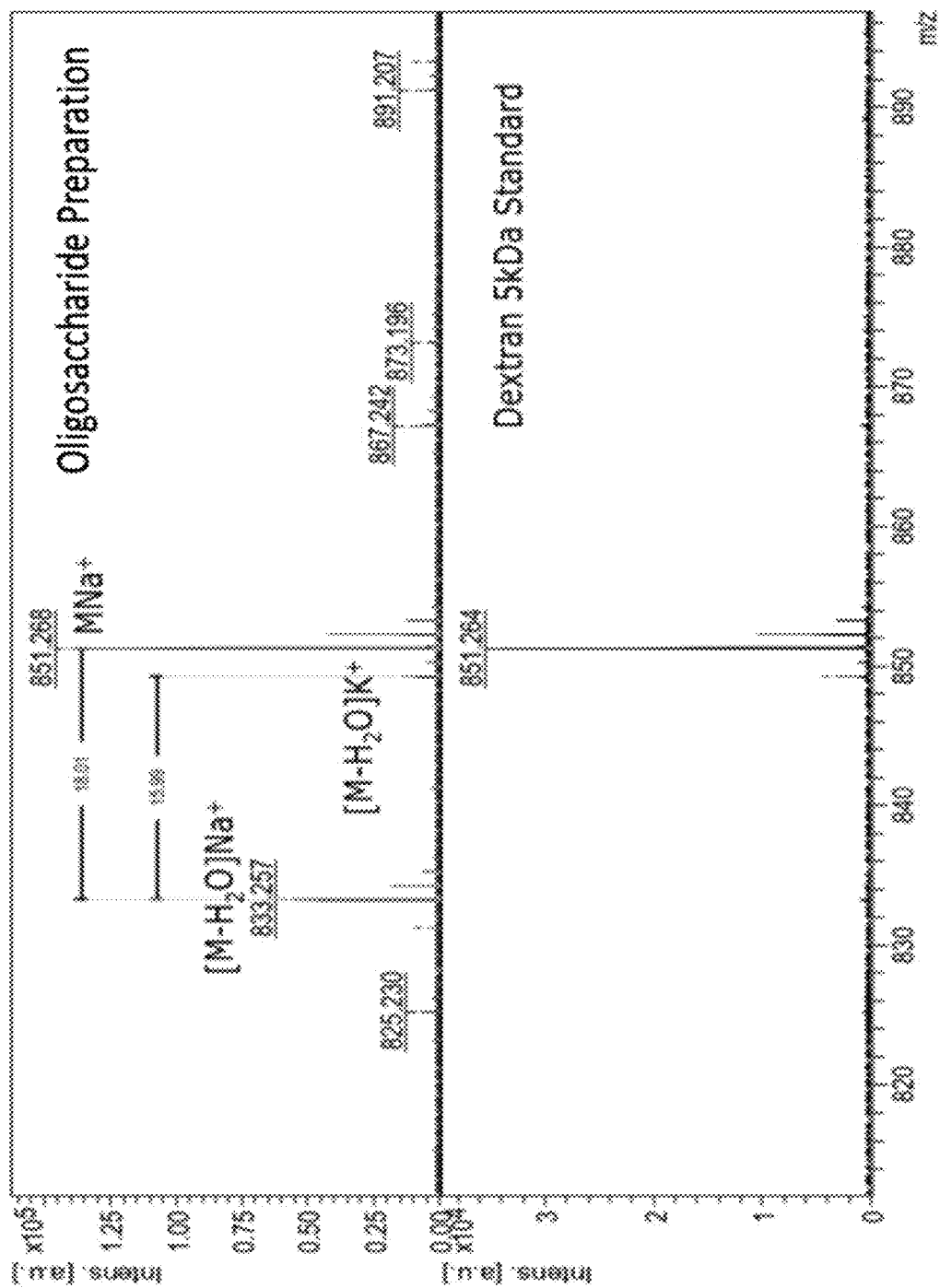
FIG. 7 illustrates MALDI-MS spectra comparing the oligosaccharide preparation from Example 9 versus a conventional dextran.

A commercial 5 kDa dextran was analyzed by MALDI-MS for the presence of anhydrosugar subunits. FIG. 7 illustrates the clear presence of the offset peak shifted −18 g/mol from the principal DP peak (Na+ adduct at 851.268 g/mol). By contrast the dextran sample was found to be essentially free of anhydro sugar subunits.

Example 14: Quantification of the Anhydro DP Component by LC-MS/MS

Figure 8:
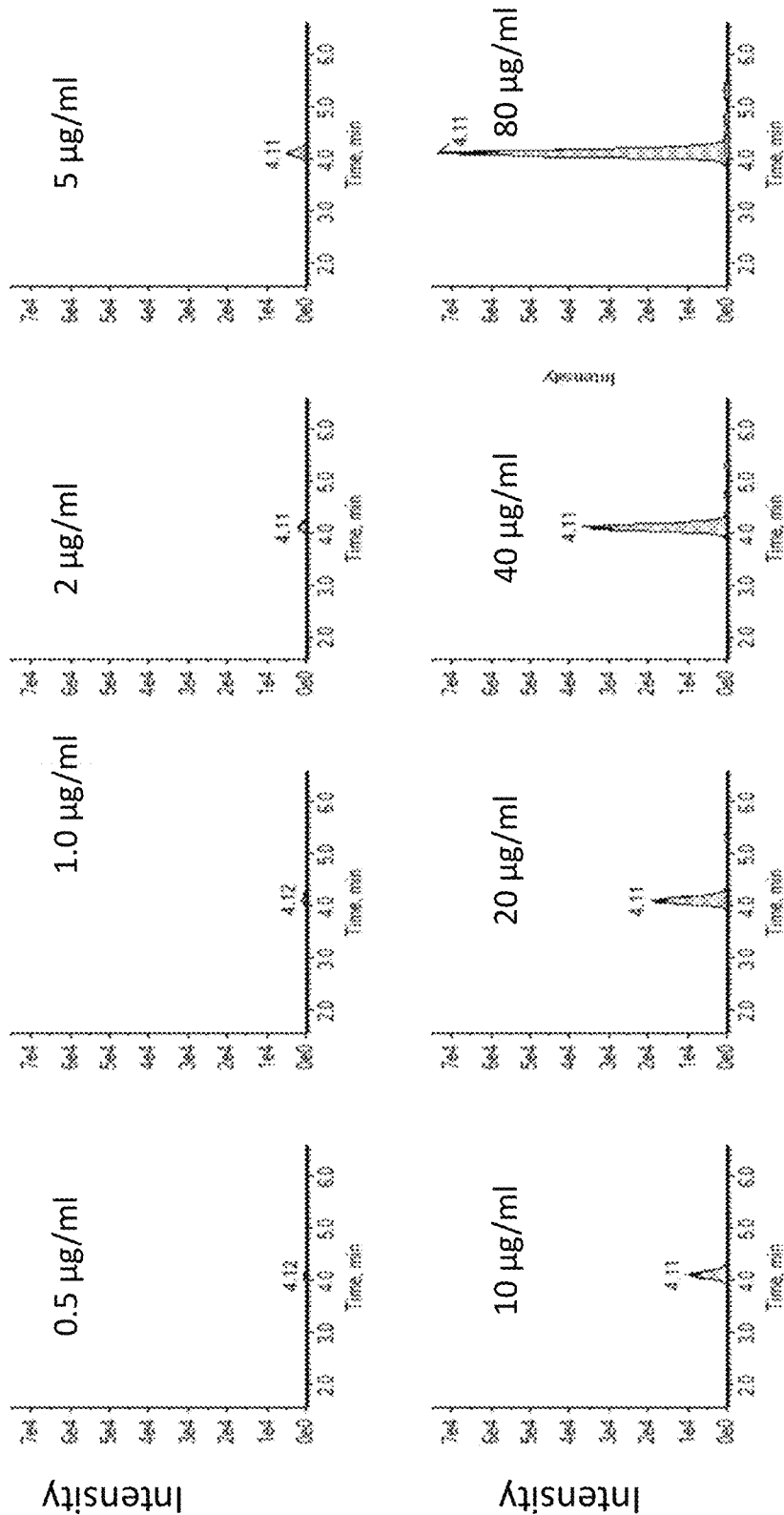
FIG. 8 illustrates LC-MS/MS detection of the anhydro DP2 species at concentration of 1-80 µg/mL of an oligosaccharide preparation in water.
Figure 9:
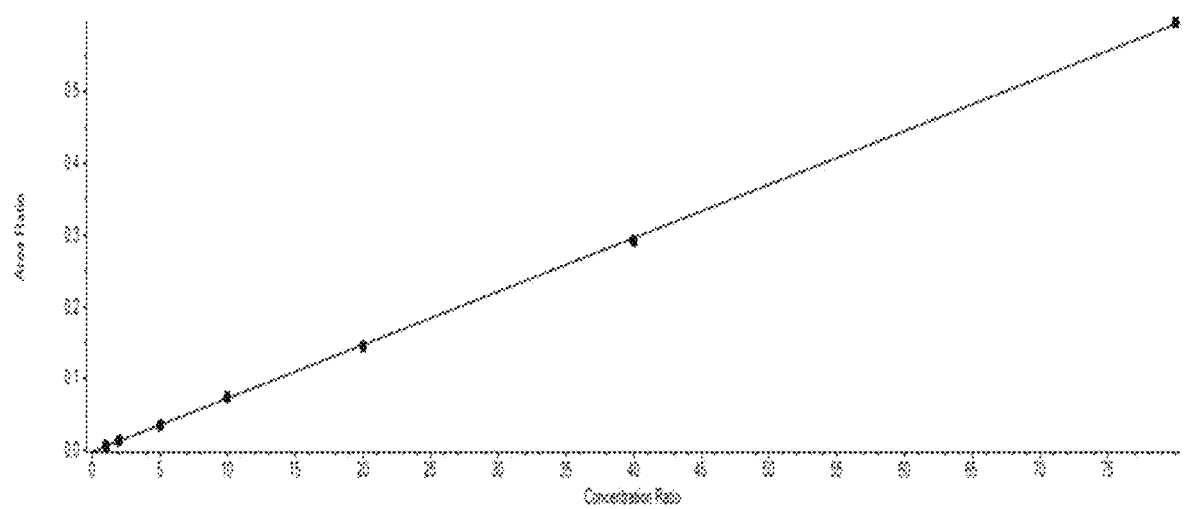
FIG. 9 illustrates a linear calibration curve resulting from the LC-MS/MS detection of FIG. 8.

Samples were dissolved in water and separated using a Capcell Pak NH2 (Shiseido; 250×4. 6 mm, 5 µm) column at a flowrate of 1 mL/min under isocratic conditions of water/acetonitrile 35/65. In some cases, following chromatographic separation, 50 µL 0.05% NH$_4$OH was added to enhance ionization. The anhydro DP2 content was determined by MS/MS detection. For MS detection ESI probe was used in negative mode and MRM method allowed targeted analysis. FIG. 8 illustrates detection of an oligosaccharide preparation from Example 9 over a concentration range of 1-80 µg/mL in water, with a linear calibration curve (shown in FIG. 9) from the area under the LC-MS/MS chromatogram to concentration.

FIGS. 15A-15C, 16A-16C, 17A-17C, and 18A-18C illustrate the presence of the anhydro DP2, anhydro DP1, and DP2 species detected by LC-MS/MS in an oligosaccharide preparation of Example 1, Example 3, Example 4, and Example 7, respectively.

Example 15: Preparation of Feed Comprising Oligosaccharide Preparations

Poultry and swine diets were prepared to demonstrate the incorporation of oligosaccharide preparations into the diet. Control feeds exhibiting a variety of ingredient compositions and corresponding treated feeds obtained by augmenting the respective control feeds with the oligosaccharide preparations of Example 9 were prepared as follows:

Example Feed 15.1: Control Feed 15.1 (CTR) was prepared using 62% corn meal and 32% soybean meal. Treated Feed 15.1 (TRT) was prepared by augmenting the control feed 15.1 (CTR) with 500 mg/kg of an oligosaccharide preparation from Example 9. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.2: Control Feed 15.2 (CTR) was prepared using 62% corn meal, 3% soybean concentrate, and 26% soybean meal. Treated Feed 15.2 (TRT) was prepared by augmenting the control feed 15.2 (CTR) with 500 mg/kg of an oligosaccharide preparation from Example 9. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.3: Control Feed 15.3 (CTR) was prepared using 52% corn meal, 6% corn starch, 5% soybean concentrate, 26% soybean meal, and a titanium oxide microtracer. Treated Feed 15.3 (TRT) was prepared by augmenting the control feed 15.3 (CTR) with 500 mg/kg of an oligosaccharide preparation. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.4: Control Feed 15.4 (CTR) was prepared using 55% corn meal and 39% soybean meal. Treated Feed 15.4 (TRT) was prepared by augmenting the control feed 15.4 (CTR) with 1,000 mg/kg of an oligosaccharide preparation. For the treated diet, the oligosaccharide preparation was provided in a powder form by drying the oligosaccharide onto ground rice hulls as a carrier and adding the powder to the mixer using a micro-ingredient balance prior to pelleting.

Example Feed 15.5: Control Feed 15.5 (CTR) was prepared using 62% corn meal, 3% soybean concentrate, and 26% soybean meal. Treated Feed 15.5 (TRT) was prepared by augmenting the control feed 15.5 (CTR) with 500 mg/kg of an oligosaccharide preparation from Example 9. For the treated diet, the oligosaccharide preparation was provided in a powder form and adding the powder to the mixer using a micro-ingredient balance prior to pelleting.

Example Feed 15.6: Control Feed 15.6 (CTR) was a commercial U.S. corn-soy starter poultry feed. Treated Feed 15.6 (TRT) was a commercial U.S. corn-soy starter poultry feed containing 500 ppm of an oligosaccharide preparation. For the treated diet, the oligosaccharide preparation was provided in a powder form and adding the powder to the mixer using a micro-ingredient balance prior to pelleting.

Example Feed 15.7: Control Feed 15.7 (CTR) was a research corn-soy poultry feed with the following diet composition: corn meal 62.39%, soybean meal 31.80%, calcium carbonate 0.15%, bicalcic-phosphate 2.2%, sodium chloride 0.15%, DL-Methionine 0.15%, L-Lysine 0.10%, Soya Oil 2.00%, vitamin-mineral premix 1.00%, and coccidiostat 0.06%. Treated Feed 15.7 (TRT) was obtained by supplementing the control feed 15.7 (CTR) with 1000 ppm of the oligosaccharide preparation of Example 9.1. For the treated diet, the oligosaccharide preparation was provided as 60% syrup in water and was applied by spraying the syrup onto the feed post pelleting.

Example Feed 15.8: Control Feed 15.8 (CTR) was a research corn-soy poultry feed with the following composition: wheat meal 48.45%, soybean meal 32.00%, rye 12%, calcium carbonate 0.20%, bicalcic phosphate 2.00%, sodium chloride 0.20%, DL-methionine 0.15%, soya oil 4.00%, vitamin-mineral premix 1.00%. Treated Feed 15.7 (TRT) was obtained by supplementing the control feed 15.7 (CTR) with 1000 ppm of the oligosaccharide preparation of Example 9.3. For the treated diet, the oligosaccharide preparation was provided as 60% syrup in water and was applied by spraying the syrup onto the feed post pelleting.

As would be understood by one skilled in the art, the 15.1-15.6 also contained industry standard levels of fat, vitamins, minerals, amino acids, other micronutrients and feed enzymes. In some cases the feeds contained a cocciodiostat, but were free in all cases of antibiotic growth promoters. The feeds were provided as either mash, pelletized, or crumbled diets, according to standard practices.

Example 16: Synthesis of an Oligosaccharide Preparation with a Monotonically Decreasing DP Distribution 330 grams of D-glucose monohydrate and 0.3 grams of (+)-Camphor-10-sulfonic acid were added to a one-liter, three-neck flask with overhead mechanical mixing provided by high-torque mechanical mixer through a flex coupling. The flask was secured inside a hemispherical electric heating mantle operated by a temperature control unit via a wand thermocouple inserted into the reaction mixture. The tip of the thermocouple was adjusted to reside within the reaction mixture with several mm clearance above the mixing element. The flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction temperature was increased to between 120° C. and 130° C., the apparatus was switched from a reflux condenser to a distillation configuration with a round bottom receiving flask placed in an ice bath. The reaction was maintained at 130° C. with 120 RPM mixing for sixty minutes and the mass of condensate collected in the receiving flask was recorded as a function time at 10 minute intervals. The reaction was quenched by adding distilled water and removing the heat. After the product mixture cooled to room temperature, an aliquot of the product syrup was diluted to about 1 Brix as determined by refractive index. The diluted aliquot was microfiltered using a 0.2 micron syringe filter and analyzed by HPLC size exclusion chromatography (SEC). SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight. The DP equilibrium constant was determined to be K=3.3 and the DP distribution was found to be monotonically decreasing. FIG. 10 clearly illustrates the shape of the DP distribution as determined by HPLC-SEC.

Example 17: Synthesis of an Oligosaccharide Preparation with a Non-Monotonic DP Distribution 330 grams of D-glucose monohydrate and 0.3 grams of (+)-Camphor-10-sulfonic acid were added to a one-liter, three-neck flask with overhead mechanical mixing provided by high-torque mechanical mixer through a flex coupling. The flask was secured inside a hemispherical electric heating mantle operated by a temperature control unit via a wand thermocouple inserted into the reaction mixture. The tip of the thermocouple was adjusted to reside within the reaction mixture with several mm clearance above the mixing element. The flask was equipped with a reflux condenser cooled by a water-glycol mixture maintained below 4° C. by a recirculating bath chiller.

The reaction mixture was gradually heated to 135° C. with continuous mixing with a stir rate of 80-100 rpm. When the reaction temperature was increased to 130° C., the apparatus was switched from a reflux condenser to a distillation configuration with a round bottom receiving flask placed in an ice bath. The reaction was maintained at 135° C. with 120 RPM mixing for thirty-five minutes. The reaction was quenched by adding distilled water and removing the heat. After the product mixture cooled to room temperature, an aliquot of the product syrup was diluted to about 1 Brix as determined by refractive index. The diluted aliquot was microfiltered using a 0.2 micron syringe filter and analyzed by HPLC size exclusion chromatography (SEC). SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight. The DP distribution was found to be non-monotonically decreasing. FIG. 11 clearly illustrates that the DP3 content is greater than the DP2 content and that the DP4 and DP5 contents are essentially equal.

Example 18: Fed-Batch Synthesis of an Oligosaccharide Preparation 330 grams of D-glucose monohydrate and 0.3 grams of 2-Pyridinesulfonic acid were added to a one-liter, three-neck flask with overhead mechanical mixing provided by high-torque mechanical mixer through a flex coupling. The flask was secured inside a hemispherical electric heating mantle operated by a temperature control unit via a wand thermocouple inserted into the reaction mixture. The tip of the thermocouple was adjusted to reside within the reaction mixture with several mm clearance above the mixing element. The flask was equipped with a reflux condenser cooled by a water-glycol mixture maintained below 4° C. by a recirculating bath chiller.

The reaction mixture was gradually heated to 130° C. with continuous mixing with a stir rate of 80-100 rpm. When the reaction temperature was increased to between 120° C. and 130° C., the apparatus was switched from a reflux condenser to a distillation configuration with a round bottom receiving flask placed in an ice bath. The reaction was maintained at 130° C. with 120 RPM and the mass of condensate collected in the receiving flask was recorded as a function time at 20 minute intervals. After 210 minutes, an additional 110 grams of D-glucose monohydrate were added to the reaction. After 420 minutes, the reaction was quenched by adding distilled water and removing the heat. After the product mixture cooled to room temperature, an aliquot of the product syrup was diluted to about 1 Brix as determined by refractive index. The diluted aliquot was microfiltered using a 0.2 micron syringe filter and analyzed by HPLC size exclusion chromatography (SEC). SEC analysis was performed on an Agilent 1100 series HPLC with refractive index detection using an Agilent PL aquagel-OH 20 column at 40° C. with distilled water at 0.45 mL/min as the mobile phase. Retention-time to MW calibration was performed using standard solutions with known molecular weight. The DP equilibrium constant was determined to be K=0.8 and the DP distribution was found to be monotonically decreasing.

Example 19: Growth Performance of Commercial Broiler Chickens Fed an Oligosaccharide Preparation Broiler chickens were grown on the diets of Example 15.6 to determine the effect of the oligosaccharide preparation on the growth performance of the animals. Specifically, commercial corn-soymeal poultry feeds containing dried distillers grains with solubles (DDGS), a coccidiostat, and a standard micronutrient blend, were manufactured according to industry practices and a three phase feeding program. By proximate analysis, the feed compositions were determined as shown in Table 6.

TABLE 6

Feed Composition

| Component | Starter | Grower | Withdrawal | Method |
|---|---|---|---|---|
| Moisture | 13.0% | 13.0% | 12.9% | AOAC 930.15 (drafted oven) |
| Crude Protein (CP) | 24.1% | 21.5% | 19.6% | AOAC 992.15; AOAC 990.03 |
| Fat (EE) | 3.2% | 3.8% | 3.9% | AOAC 920.39 (ether extraction) |
| Crude Fiber (CF) | 2.7% | 2.4% | 2.4% | AOAC 962.09 (hydrolysis) |
| Ash (AR) | 5.2% | 4.3% | 4.3% | AOAC 942.05 (muffle furnace) |
| NFE, by difference | 51.9% | 55.1% | 56.9% | Calculated: 1-CP-EE-CF-AR |
| Total | 100.0% | 100.0% | 100.0% | |

Control (CTR) and treated (TRT) diets were prepared for each phase as described in Example 15.6, where the treat diets were prepared by augmenting the control diet with one pound per treated short ton using the oligosaccharide preparation of Example 9.7. In total, about 50 short tons of each diet were manufactured.

Day-of-hatch Hubbard M99×Cobb 500 straight run chicks were obtained from a commercial poultry hatchery and placed randomly into 36 ft×40 ft pens constructed into a tunnel-ventilated, dirt-floor poultry house. Approximately 30,000 birds were placed in total, with an equal number of birds in each pen. The house bedding consisted of built-up litter top-dressed with fresh wood shavings. A standard commercial environmental and lighting program were employed. Animals and housing facilities were inspected daily, including recording the general health status, feed consumption, water supply and temperature of the facility. Any mortalities were recorded daily.

Birds in odd numbered pens were fed the treated diet (i.e., containing the feed additive at 2 lbs/ton inclusion), and birds in the even numbered pens received the control diet. All diets were provided ad libitum via automatic feeders in each pen, and on feeder trays from day one until day 7. Water was provided ad libitum from a nipple drinking line.

The starter phase took place from day 0 to day 13, the grower phase from day 14 to day 27, and the withdrawal phase from day 28 through the end of the study, day 31. Bird weights by pen were recorded on days 0 and 31. The total mass of consumed feed was recorded for each pen. Weight gain and FCR were then determined for each pen according to standard industry practices.

On day 31, six male birds were randomly selected from each pen for blood and cecal sampling. The live weight of each sampled bird was recorded. A blood sample was collected via wing puncture into vacutainer tubes and frozen following coagulation and serum separation. Each sampled bird was then euthanized via cervical dislocation followed by extraction of the ceca using standard veterinary methods. Following dissection, cecal contents were transferred to 15 mL conical tubes, the weight of the cecal contents was recorded, and the contents were flash frozen to −80 degrees Celsius.

From the weights of the sampled birds, the treatment group exhibited an 11 point increase in body weight, significant at $P<0.05$ (by ANOVA).

Example 20: Replicate Batches Scale-Up for Manufacturing

The production scale of oligosaccharide preparations was increased to that of a 720 L overhead-stirred tank reactor. Twelve batch reactions using a scaled-up procedure derived from those of Example 9.2 were performed at the 720 L scale. The resulting oligosaccharide preparations were characterized against pre-determined QC acceptance criteria to perform batch qualification and to assess the process stability. Residual catalyst in the final product was determined for batches using the procedure of Example 26.

For the twelve batches, process conditions such as temperature, reaction time, and reaction pressure were varied intentionally in a range around the nominal conditions of Example 9.2 to assess the sensitivities of the resulting product to reasonable variations in the process conditions that might be expected in a typical manufacturing environment. For select batches, an in situ viscosity probe was used to monitor the time dependence of the viscosity of the reactor contents. In certain batches, the reaction stopping time employed an in-process control (IPC) based on the continuous viscosity measurement. Material amounts, including the dispensed quantities of reactants, distillation water, and evolved condensate were measured either by mass via load cells on the reactor and auxiliary tanks or volumetric flow and time.

The resulting oligosaccharide syrup appearance of all the batches was determined by visual inspection as a caramel syrup. The total dissolved solids content was determined by Karl-Fisher titration, the residual monomer content, MWn and MWw were determined by HPLC/GPC chromatography, the pH was determined by calibrated pH meter and the anhydro-DP2 content was determined by LC-MS/MS. As shown in Table 7, the following batch characterization data were obtained (N/R="data not reported"):

TABLE 7

Characterization of Oligosaccharide Preparations

| Batch | wt % DS | pH | Residual Catalyst | wt % DP1 | MWn | MWw | Anhydro DP2 Content (g Anhydro DP2/ g total DP2) |
|---|---|---|---|---|---|---|---|
| 27.1 | 66.4 | N/D | N/R | 17.5 | 777 | 1218 | 0.84% |
| 27.2 | 68.8 | 3.3 | N/R | 17.9 | 735 | 1091 | 0.91% |
| 27.3 | 69.4 | 3.1 | 0.095 | 14.8 | 807 | 1276 | N/R |
| 27.4 | 71.0 | N/D | 0.068 | 15.5 | 793 | 1241 | 1.04% |
| 27.5 | 70.9 | 3.2 | 0.057 | 15.8 | 777 | 1196 | 1.15% |
| 27.6 | 70.9 | 3.3 | N/R | 16.3 | 773 | 1170 | N/R |
| 27.7 | 70.7 | 3.0 | N/R | 15.7 | 783 | 1226 | 1.13% |
| 27.8 | 70.5 | 3.9 | N/R | 16.1 | 785 | 1182 | 1.09% |
| 27.9 | 71.1 | 4.1 | N/R | 17.1 | 761 | 1169 | 1.09% |
| 27.10 | 70.4 | 4.1 | N/R | 16.3 | 778 | 1193 | 1.15% |
| 27.11 | 70.5 | 4.7 | N/R | 18.6 | 696 | 995 | 1.33% |
| 27.12 | 70.9 | 3.9 | N/R | 16.7 | 769 | 1194 | 1.12% |

Approximately 6 metric tons of 70 wt % syrup were produced in total. Batches were segregated prior to QC analysis and measured against the following acceptance criteria: total dissolved solids between 68-72 wt %, residual monomer content not greater than 18 wt % versus total carbohydrates, caramel syrup appearance, and residual catalyst not greater than 0.1 wt % on a final syrup basis. For example, batches 27.3, 27.4, and 27.5 were accepted based on these criteria, while batch 27.11 was identified for retesting and/or rejection.

Example 21: pH Adjustment of an Oligosaccharide Preparation

The pH of the oligosaccharide preparation of Example 9.2 at 50 wt % solids content was determined in triplicate by diluting 5.00±0.05-gram aliquots of the oligosaccharide preparation with 1.80±0.02 mL of deionized water and mixing by vortex agitation to obtain a uniform concentration. The pH of each aliquot was measured with a calibrated pH meter (VWR, Symphony B30PCI) to obtain an average reading of 2.4 pH units.

To 1.2 kg of the oligosaccharide preparation of Example 9.2 was added 6.53 mL of 1.0 molar aqueous sodium hydroxide solution. The resulting mixture was mixed vigorously to achieve a uniform pH-adjusted syrup. The pH of the resulting adjusted syrup at 50 wt % solids content was then determined in triplicate as described above to obtain an average of 4.1 pH units.

The pH adjustment procedure was repeated for replicate batch syntheses at various scales, but with certain variations in the procedure by which the base was provided to the product oligosaccharide composition. For one batch, the pH adjustment was performed as the final step of the reaction, prior to the dilution of reaction water. In another batch, the pH adjustment was performed concurrently with the dilution step by first dissolving the required amount of base in the dilution water; the base and dilution water were therefore added together to quench the reaction a single step to produce a final syrup at the desired pH. In another batch, the base was provided as food-grade sodium hydroxide pellets. In another batch, 10 ppm of a food-grade silicone emulsion (Dow Xiameter AFE-0100) was added to the reaction prior to dilution and pH adjustment.

Example 22: Preparation of a Glass Powder Formulation of an Oligosaccharide Preparation Approximately 50 grams of the oligosaccharide preparation of Example 9.1 was dispensed onto a drying tray and placed in a forced-air convection heater at 60° C. to produce a caramel colored brittle glass. The glass was removed from the drying tray and ground with a shear rotary mill to yield a light-orange colored flowable powder. The particle size of the powder was determined by sieving to be between 100 and 2000 microns, with 90% of the mass below 1350 microns. The true density of the coarse milled powder was determined by Helium Pyncnometry to be 1.3063 g/mL. The resulting powder was observed to be flowable.

The formulation procedure was repeated using a hammer mill to obtain a fine powder with 90% of the mass of the powder exhibiting a particle size below 196 microns. The true density of the fine milled powder was determined to be 1.5263 g/mL. The resulting powder was neither stable nor flowable.

DSC measurements were performed on the powders using two temperature cycling programs. In the first program, temperature was ramped to 160° C. from 0° C. at a rate of 5° C./min, then annealed back to 0° C. at a rate of −5° C./min, followed by a final heating back to 160° C. In the second program, the temperature was ramped to 50° C. from −50° C. at a rate of 5° C./min, annealed to −60° C. at a rate of −5° C./min and then heated to 60° C. at a rate of 5° C./min. The powder was observed to exhibit a glass transition temperature of between 20 and 40° C., dependent on the residual water content of the solid between 5 and 10 wt % moisture.

The milling formulation process was repeated for each of the oligosaccharide preparations of Example 9.2, Example 9.3, Example 9.4, and Example 9.5. The powders readily re-dissolved in water and alcohol-water mixtures, but were insoluble in acetone, methanol, and anhydrous ethanol.

Example 23: Preparation of a Carrier-Loaded Powder Formulation

Equal masses of a 70 wt % aqueous syrup of the oligosaccharide preparation of Example 9.2 and diatomaceous earth were combined at room temperature to yield a stable, flowable powder. The resulting powder comprised about 35 wt % adsorbed oligosaccharide (dry solids basis) and about 50 wt % carrier. The particle size distribution of the powder was measured by sieving. 10% by weight of the powder exhibited a particle size below 290 micrometers, 50% by weight of the powder exhibited a particle size below 511 micrometers, and 90% by weight of the powder exhibited a particle size below 886 micrometers. The powder was stable to segregation and cohesion, as determined using standard aeration and compressibility tests. The true density of the resulting powder was measured by Helium pyncnometry to be 1.8541 g/mL.

The carrier loading formulation was repeated using feed-grade silica to yield a stable, flowable powder with a loading of at least 50 wt % oligosaccharide preparation (dry solids basis) with respect to the final powder. The true density of the resulting powder was measured to be 1.5562 g/mL.

Example 24: Preparation of an Extruded Solid Form

A solid extruded product was prepared by blending 20% of the oligosaccharide preparation of Example 9.2 with semolina and formulated the mixture through a jacketed twin-screw dye extruder to form a flowable powder with a particle size between 0.2 mm and 3.0 mm, with 90% of the mass below 2 mm particle size. The resulting powder was observed to be free-flowing and stable.

Example 25: Preparation of Stable Powder Formulations

The solid formulations, including those of Examples 22-24, were assessed to determine their stability and hygroscopicity. The powders of Examples 23 and 24 were observed to be stable to segregation and agglomeration, while the coarse milled powder of Example 22 was observed to be unstable with respect to segregation.

Sample of each powder formulation to be tested were placed in a sealed climate chambers at 50% relative humidity and 65% relative humidity for up to two-weeks exposure at 25° C. Of the forms tested, several exhibited little or no mass gain upon exposure to humidity and remained flowable after the two-week exposure period. The fine-milled powder of Example 22 was found to be unstable with exposure to humidity.

Example 26: Determination of Residual Catalyst in Oligosaccharide Preparations The residual acid catalyst content of oligosaccharides preparations was determined by Ion Chromatography. Between 80 and 100 milligrams of a powder formulation of the oligosaccharide preparation (obtained for example as described in Example 22) were dissolved in exactly 1.00 milliliter and centrifuged to remove particulates if necessary. The resulting solution was analyzed by ion chromatography at 30° C. using a Thermo Dionex ICS-3000 System equipped with conductivity detection, a 4×250 mm Ion Pac AS19A column, an Ion Pac AS19G 50 4×50 mm pre-column and a continuously regenerated CR-ATC anion trap column using KOH in water as the eluent. Elution was conducted at 10 mM KOH for the first ten minutes after injection followed by a gradient elution increasing linearly to 55 mM KOH at 25 minutes, then decreasing to 10 mM KOH at 26 minutes, and remaining at 10 mM KOH until the end of the program.

For the oligosaccharide preparation of Example 9.2, the concentration of residual catalyst was determined by reference to a standard calibration curve generated using an authentic sample of (+)-camphor-10-sulfonic acid. A representative batch of the oligosaccharide preparation of Example 9.2 was analyzed and the residual catalyst concentration was determined to be 0.62 mg per gram of 70 wt % syrup.

Example 27: Qualification of the Residual Catalyst Concentration for Batch Acceptance The residual catalyst determination of Example 26 was compared against a batch acceptance criterion to determine suitability of the batch for further use. The acceptance limit for the concentration of residual catalyst in the product oligosaccharide preparation was preestablished to be <1.0 mg per gram product syrup. The measured value of the residual catalyst was 0.62 mg per gram of product syrup. Therefore, the acceptance criterion was met for the tested batch and the batch was accepted for further use.

Example 28: Extraction of Feed Samples

Diets prepared according to the procedures of Example 15 were processed by extraction. Feed samples were ground with a mill. Five grams of the resulting milled feed were weighted into a 50 mL volumetric flask and hot water (approx. 80° C.) was added. After shaking, the mixture was incubated in an ultrasonic water bath at 80° C. for 30 minutes. After cooling, the solution was centrifuged for 20 min at 3000×g and the supernatant was filtered through a 1.2 μm filter followed by a 0.45 μm filter (and in some cases by a 0.22 μm filter). The resulting filtered solutions were evaporated to dryness with a rotary evaporator.

In some cases, the extraction was performed using 50 wt % ethanol in water as an alternative extraction solvent. In some cases, the filtration step was performed using a 5,000 Dalton molecular-weight cutoff membrane filter.

Example 29: Enzymatic Processing of Feed Extracts

The feed extracts of Example 28 were subjected to one or more enzymatic hydrolysis steps to digest oligosaccharides naturally present in the feed. A mixture of α-Amylase and amyloglycosidases were used to digest α(1,4) linkages of gluco-oligosaccharides and starch. Invertase and α-galactosidase were used to remove sucrose, raffinose, and other common fiber saccharides.

Enzyme solutions were prepared as follows: Amyloglucosidase (*A. niger*) 36000 U/g solution at 800 U/mL in ammonium acetate buffer (ammonium acetate 0.2 M pH 5 containing 0.5 mM MgCl2 and 200 mM CaCl2), α-Amylase (Porcine Pancreas) 100000 U/g Megazyme: solution at 800 U/mL in ammonium acetate, Invertase from Backer's yeast (*S. cerevisiae*) 300 U/mg Sigma: solution at 600 U/mL in ammonium acetate buffer, α-Galactosidase from *A. niger* Megazyme 1000 U/mL.

The dry feed extracts of Example 16 were re-suspended in 10 mL ammonium acetate buffer. 50 μl of α-amylase (4 U/mL final), 50 μl of amyloglucosidase (4 U/mL final), 50 μl of invertase (3 U/mL final) were added. 20 μl α-galactosidase (2 U/mL final) was added optionally. The solution was incubated for 4 hours at 60° C. The digested extract was then filtered through an ultrafiltration filter (Vivaspin Turbo 4, 5000 MWCO, Sartorius) before being evaporated to dryness on a nitrogen evaporation system. In variations of the enzymatic digestion, one or more of the above enzymes were used in combinations and the digestion period was varied between 4 hours to overnight digestion. The enzyme concentrations were varied up to twice the above loadings, and the full enzymatic digestion procedure was repeated multiple times in sequence on the same feed.

TABLE 8

List of Feed Samples for Extraction and Digestion

|  | Matrix | Extraction solvent | Filtration | Enzyme digestion |
|---|---|---|---|---|
| 1 | Blank feed | Water | 0.22 μM | — |
| 2 | Anhydro-Oligomers feed 1000 mg/kg | Water | 0.22 μM | — |
| 3 | Blank Feed | ethanol/water 50/50 | 0.22 μM | — |
| 4 | Anhydro-Oligomers feed 1000 mg/kg | ethanol/water 50/50 | 0.22 μM | — |
| 5 | Anhydro-Oligomers | Water | 0.22 μM | a + b (4 h 60° C.) |
| 6 | Blank feed | Water | 0.22 μM | a + b (4 h 60° C.) |
| 7 | Anhydro-Oligomers feed 1000 mg/kg | Water | 0.22 μM | a + b (4 h 60° C.) |
| 10 | Blank feed | ethanol/water 50/50 | 0.22 μM | — |
| 11 | Anhydro-Oligomers feed 1000 mg/kg | ethanol/water 50/50 | 0.22 μM | — |
| 12 | Anhydro-Oligomers feed 1000 mg/kg | Water | 0.45 μM | a + b (4 h 60° C.) |
| 13 | Anhydro-Oligomers feed 1000 mg/kg | Water | 0.22 μM | a + b (4 h 60° C.) |
| 14 | Blank starter feed A | Water | 0.45 μM | a + b (4 h 60° C.) |
| 15 | Anhydro-Oligomers starter feed B 2000 mg/kg | Water | 0.45 μM | a + b (4 h 60° C.) |
| 16 | Blank feed | Water | 0.45 μM | a + b + c (4 h 60° C.) |
| 17 | Anhydro-Oligomers feed 1000 mg/kg | Water | 0.45 μM | a + b + c (4 h 60° C.) |
| 18 | Rice spelt/ Anhydro-Oligomers | Water | 0.45 μM | — |
| 19 | Rice spelt/ Anhydro-Oligomers | ethanol/water 50/50 | 0.45 μM | — |
| 20 | Blank feed | Water | 0.45 μM | a + b + c (4 h 60° C.) |
| 21 | Anhydro-Oligomers feed 1000 mg/kg | Water | 0.45 μM | a + b + c (4 h 60° C.) |
| 22 | Grower feed C (blank) | Water | 0.45 μM |  |
| 23 | Grower feed D (Anhydro-Oligomers 2000 mg/kg) | Water | 0.45 μM |  |
| 24 | Pre starter feed A (blank) | Water | 0.45 μM |  |
| 25 | Pre starter feed D (Anhydro-Oligomers 1000 mg/kg) | Water | 0.45 μM |  |
| 26 | Grower feed C (blank) | Water | 0.45 μM | a + b + c + d (4 h 60° C.) |
| 27 | Grower feed D (Anhydro-Oligomers 2000 mg/kg) | Water | 0.45 μM | a + b + c + d (4 h 60° C.) |
| 28 | Pre starter feed A (blank) | Water | 0.45 μM | a + b + c + d (4 h 60° C.) |
| 29 | Pre starter feed D (Anhydro-Oligomers 1000 mg/kg) | Water | 0.45 μM | a + b + c + d (4 h 60° C.) |
| 30 | Maize | Water | 0.45 μM | — |
| 31 | Wheat | Water | 0.45 μM | — |
| 32 | Soy | Water | 0.45 μM | — |
| 33 | Maize | Water | 0.45 μM | a + b + c + d (4 h 60° C.) |
| 34 | Wheat | Water | 0.45 μM | a + b + c + d (4 h 60° C.) |

TABLE 8-continued

List of Feed Samples for Extraction and Digestion

| | Matrix | Extraction solvent | Filtration | Enzyme digestion |
|---|---|---|---|---|
| 35 | Soy | Water | 0.45 μM | a + b + c + d (4 h 60° C.) |
| 41 | Blank Feed | Water | 0.45 μM | |
| 42 | Anhydro-Oligomers feed 1000 mg/kg | Water | 0.45 μM | |
| 43 | Blank feed | Water | ultra 5000 MWCO | a + b + c X2 (overnight 60° C.) |
| 44 | Anhydro-Oligomers feed 1000 mg/kg | Water | ultra 5000 MWCO | a + b + c X2 (overnight 60° C.) |

Anhydro-Oligomers refer to anhydro-subunit containing oligosaccharides.

Blank feeds refer to nutritional compositions without added anhydro-oligomers.

Enzyme a=Amyloglucosidase (*A. niger*) 36000 U/g Megazyme

Enzyme b=α-Amylase (Porcine Pancreas) 100000 U/g Megazyme

Enzyme c=Invertase from Baker's yeast (*S. cerevisiae*) 300 U/mg Sigma

Enzyme d=α-Galactosidase from *A. niger* 620 U/mg Megazyme

Example 30: Detection of Oligosaccharide Preparations in Feed

The Control and Treated diets according to Example 15 were assayed to detect the absence or presence of oligosaccharide preparations. After diet manufacture, 1 kg samples were drawn from the final feed. The extractable solids content of the feed was obtained by water extraction using the procedure of Example 28. The resulting extracts were analyzed for the presence of anhydro-DP species by LC-MS/MS according to the procedure of Example 14.

Figure 24:
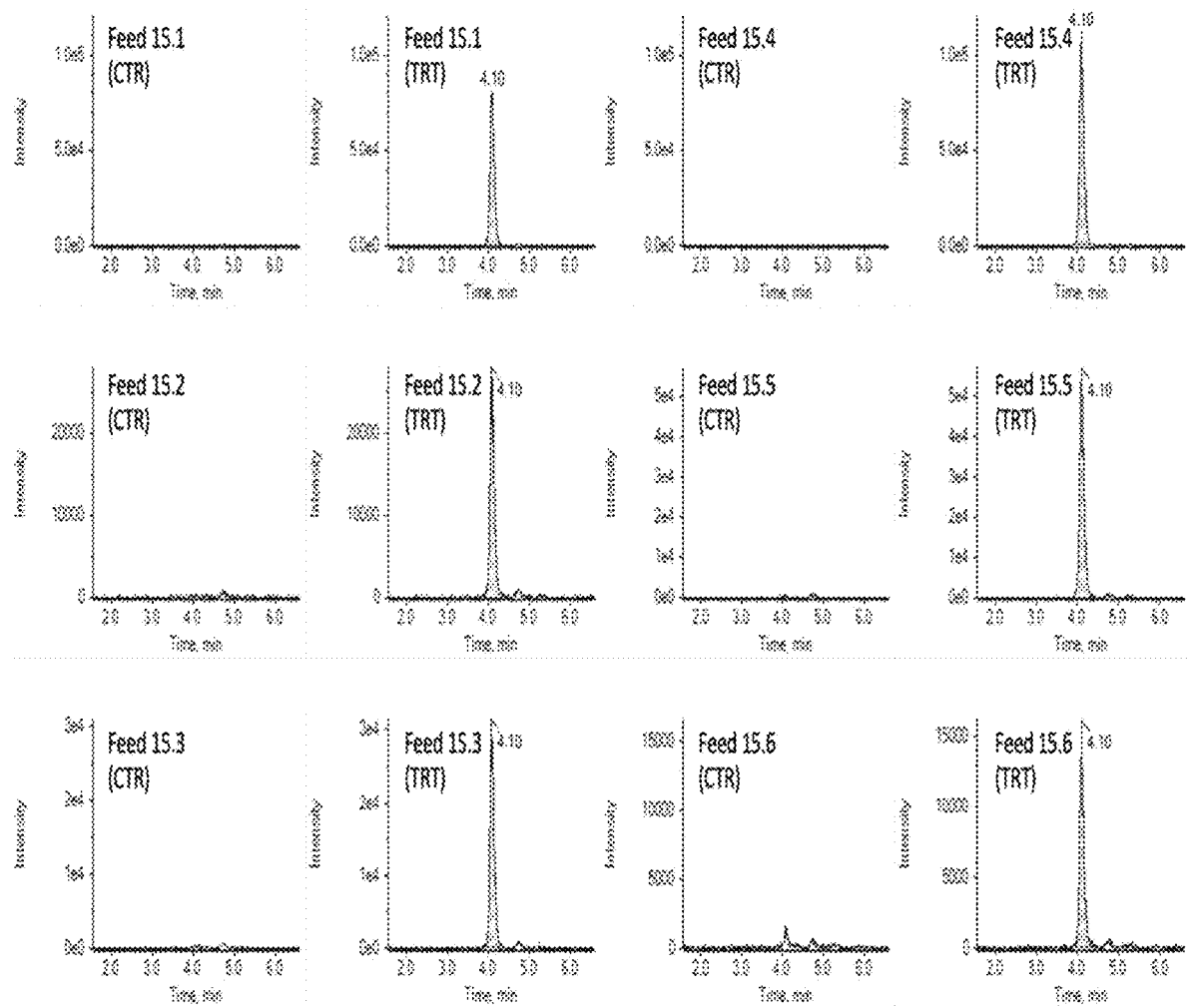
FIG. 24 illustrates the quantification of the anhdro-DP2 content of various control and treated diet compositions.

FIG. 24 shows the absence of anhydro-DP2 species in the control feeds of Examples 15.1(CTR)-15.6(CTR) versus the presence of anhydro-DP2 species in the treated feeds of Examples 15.1(TRT)-15.6(TRT). Integration of the resulting LC-MS/MS chromatograms was used to determine the presence of the oligosaccharide compositions of Example 9 in the final feed. Specifically, feeds were determined to contain the respective oligosaccharide preparation if the area under the anhydro-DP2 peak exceeded the limit of detection (or any other suitable threshold established in the method).

Example 31: Quantification of Oligosaccharide Preparations in Feed

The Control and Treated diets according to Example 15 were assayed to determine the concentration of oligosaccharide preparations in the final feed. After diet manufacture, 1 kg samples were drawn from the final feed. The extractable solids content of the feed was obtained by water extraction using the procedure of Example 28. The resulting extracts were analyzed for the presence of anhydro-DP species by LC-MS/MS according to the procedure of Example 14 and the area of the anhydro-DP2 peak was compared against a standard calibration curve to determine the concentration of the oligosaccharide preparation in the feed (Table 9).

TABLE 9

Concentration of Oligosaccharide Preparation in Feed

| Feed | Oligosaccharide Content (ppm) in Control Feed | Oligosaccharide Content (ppm) in Treated Feed |
|---|---|---|
| Example 15.1 | Not detected | 1642 |
| Example 15.2 | Not detected | 953 |
| Example 15.3 | Not detected | 1912 |
| Example 15.4 | Not detected | 549 |
| Example 15.5 | Not detected | 406 |
| Example 15.6 | Trace | 401 |

Example 32: NMR Characterization of Anhydro-Subunit Containing Gluco-Oligosaccharides Gluco-oligosaccharide preparations comprising anhydro-subunits were characterized by i) the degree of polymerization and ii) the glycosidic linkage distribution of the glucose units.

The relative molar abundances of α-(1,1)-α, α-(1,1)-β, β-(1,1)-β, α-(1,2), β-(1,2), α-(1,3), β-(1,3), α-(1,4), β-(1,4), α-(1,6), and β-(1,6) linkages were identified by NMR spectroscopy. For the determination of the linkage distribution, J-RES and $^1$H, $^{13}$C-HSQC were used. For some samples, the HSQC method showed a superior performance. For each analysis, approximately 50 mg of freeze-dried product were dissolved in D20 and transferred to a 5 mm NMR tube. Any residual catalyst or solids were removed by filtration. NMR experiments were performed on a Bruker Avance III NMR spectrometer operating at 600 MHz proton corresponding to 150 MHz carbon Larmor frequency. The instrument was equipped with a cryogenically cooled 5 mm TCI probe. All experiments are carried out at 298 K. $^1$HNMR spectra were recorded and calibrated in deuterated water (4.75 ppm). $^{13}$C NMR spectra are calibrated with acetone (30.9 ppm). Data were acquired using TopSpin 3.5 and processed with ACD/Labs running on a personal computer.

Figure 25:
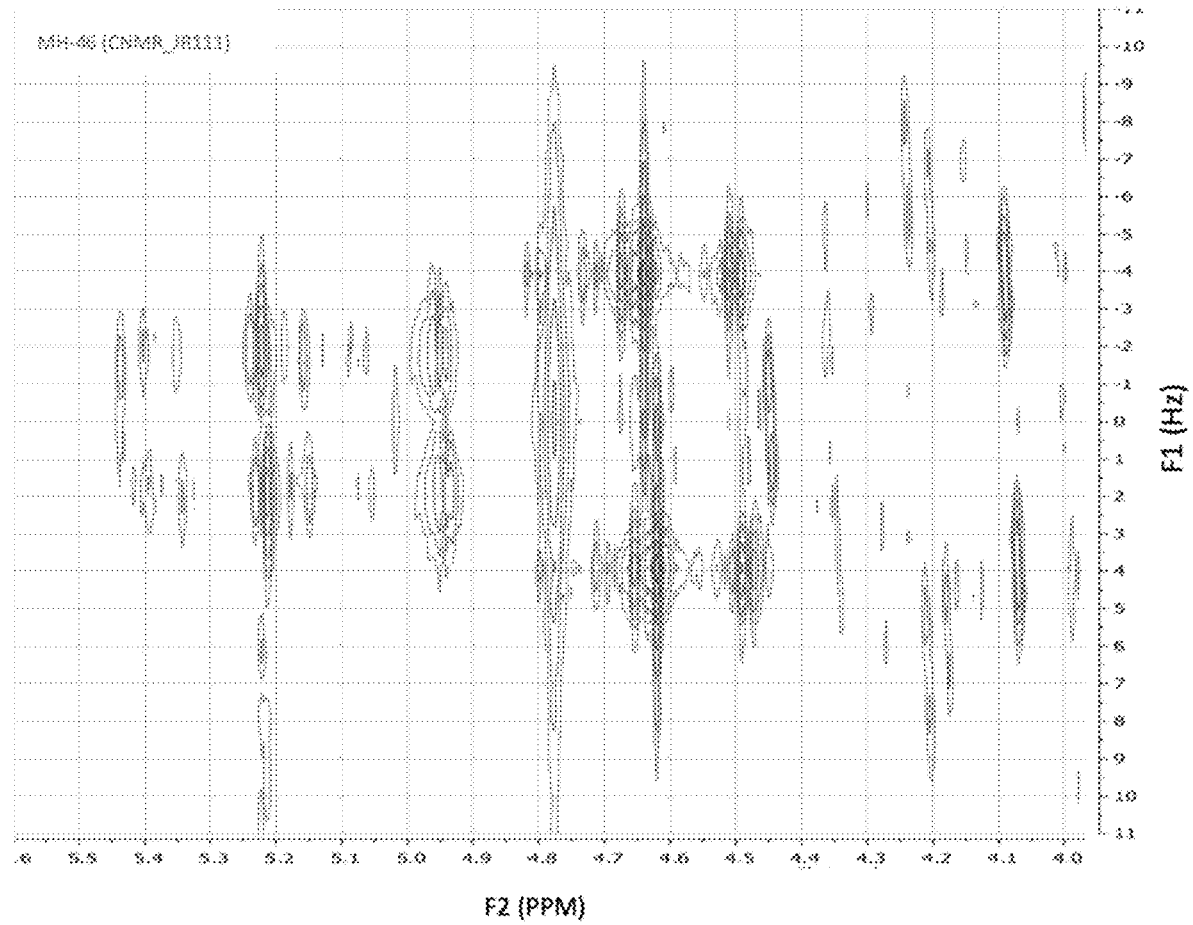
FIG. 25 illustrates a 2D-1H JRES NMR spectrum of an anhydro-subunit containing gluco-oligosaccharides sample.

FIG. 25 provides a representative 2D-1H JRES NMR spectrum of an anhydro-subunit containing gluco-oligosaccharide sample with solvent pre-saturation.

Figure 26:
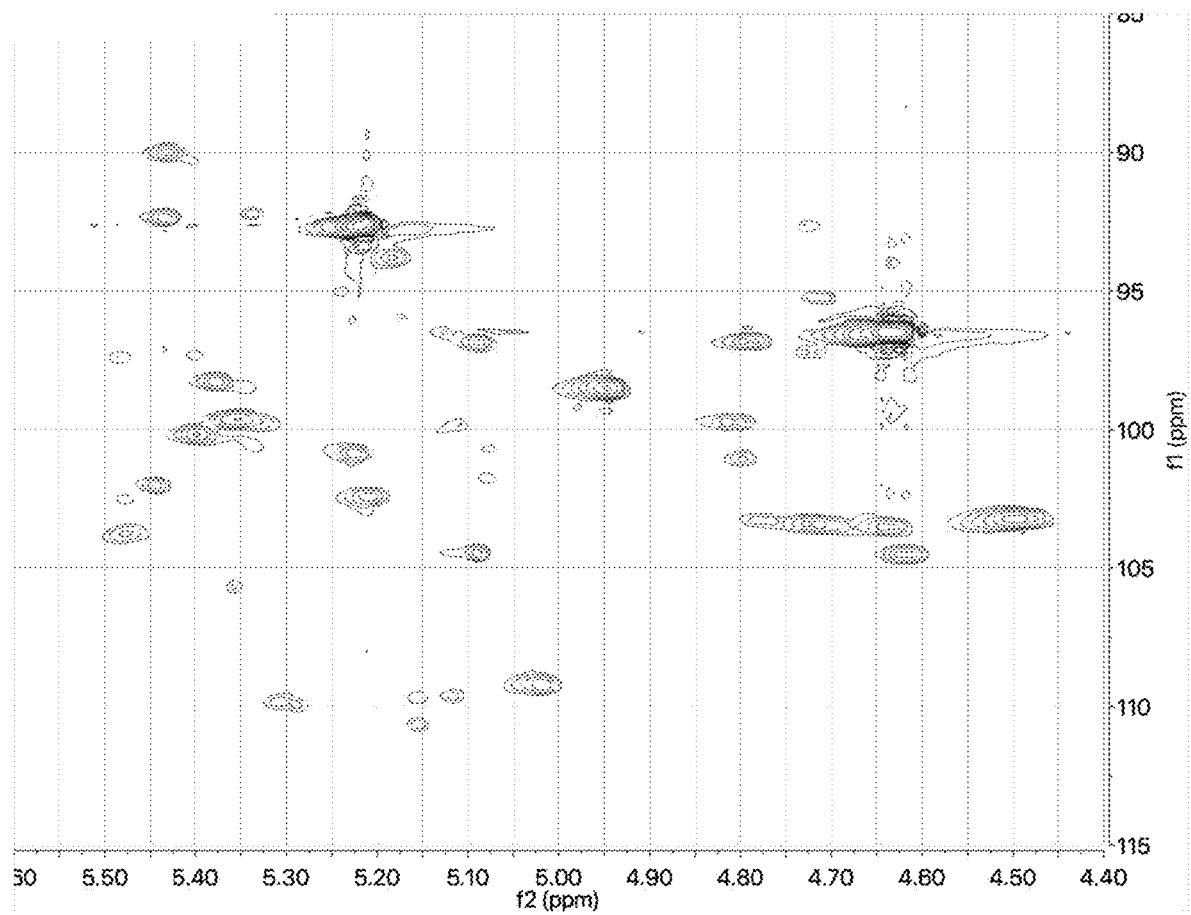
FIG. 26 is a representative $^1H$, $^{13}C$-HSQC NMR spectrum of an anhydro-subunit containing gluco-oligosaccharides sample with relevant resonances and assignments used for linkage distribution.
Figure 27:
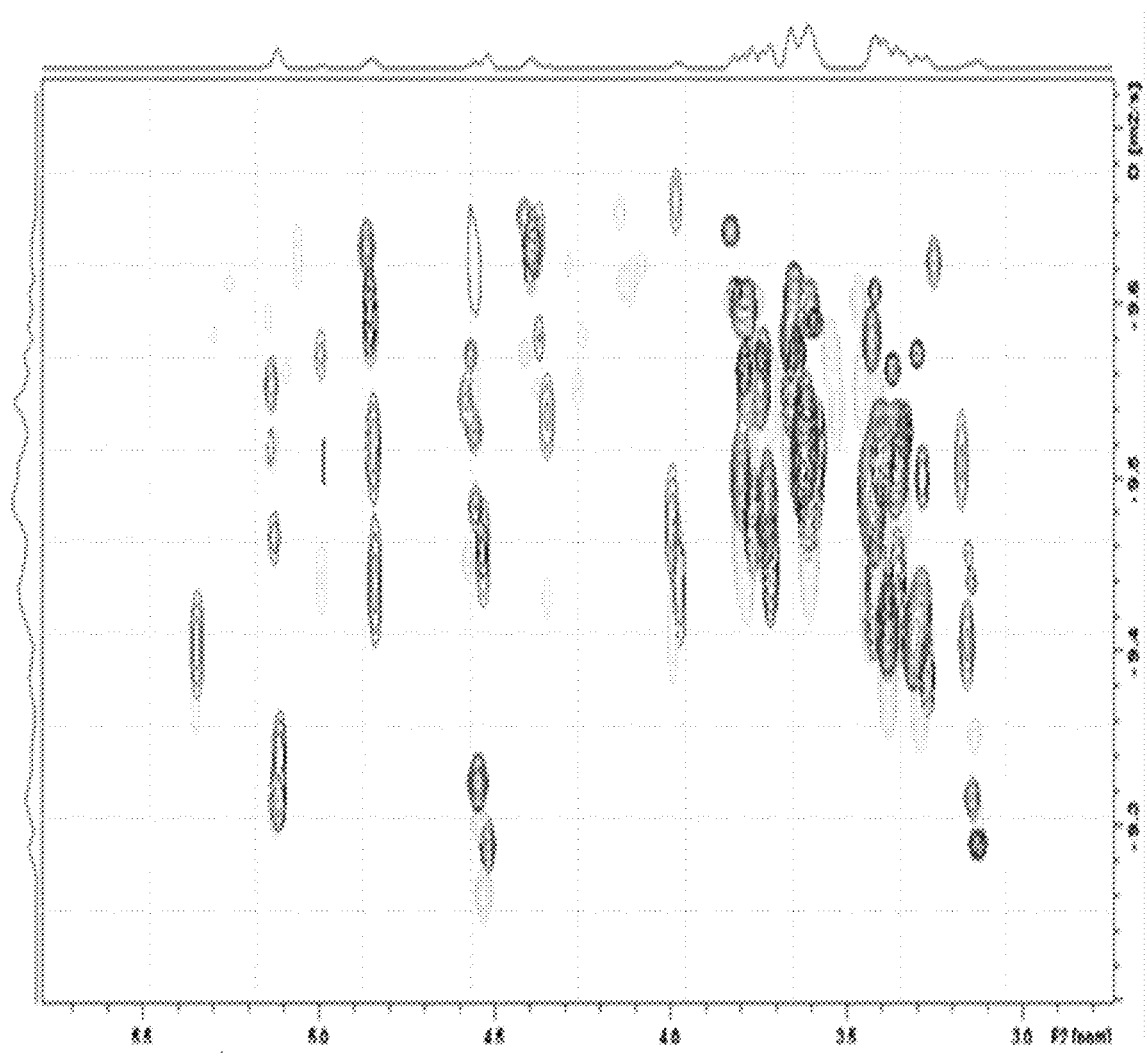
FIG. 27 illustrates an overlay of 1H DOSY spectra of three anhydro-subunit containing oligosaccharides.

FIG. 26 provides a representative 1H, 13C-HSQC NMR spectrum of an anhydro-subunit containing gluco-oligosaccharides sample FIG. 27 illustrates an overlay of $^1$H DOSY spectra of three anhydro-subunit containing oligosaccharides. Diffusion-Ordered NMR Spectroscopy (DOSY) was performed to separate the NMR signals of different species according to diffusion coefficient and thus MW homologues. Signals at the upper part of the DOSY spectra in FIG. 27 correspond to slow diffusing species, while faster diffusing species appear below.

Example 33: Formulation of a Syrup Product

The oligosaccharide preparation of Example 9.7 was pH adjusted to a pH of 4.2 with food grade sodium hydroxide according to the procedure of Example 21. The resulting syrup was packaged into a 20 liter carboy with a tamper-resistant cap. Immediately prior to sealing the container, a 500 gram sample was taken and subjected to quality testing. The total solids content of the syrup was confirmed to be greater than 70 wt %, per the methods of FCC APPENDIX X: Carbohydrates (Starches, Sugars, and Related Substances): TOTAL SOLIDS. The reducing sugar content was confirmed to be less than 50% as D-glucose on a dry weight basis according to the method of FCC APPENDIX X: Carbohydrates (Starches, Sugars, and Related Substances): REDUCING SUGARS ASSAY. Sulfated ash was confirmed to be less than 1% on a dry weight basis using the method of FCC APPENDIX II: Physical Tests and Determinations: C. OTHERS: RESIDUE ON IGNITION (Sulfated Ash) Method II (for Liquids). The sulfur dioxide content was confirmed below 40 mg/kg using an optimized Monier Williams method. The lead content was confirmed to be below 1 mg/kg using the method of AOAC International Official Method 2013.06. The total aerobic plate count was confirmed to be below 1000 cfu/g using the methods of CMMEF Chapter 7. Total yeast and mold was confirmed below 100 cfu/g using the method of AACC International Approved Method 42-50. Coliforms were confirmed below 10 MPN/g using the method of the FDA BAM Chapter 4. *E. coli* was confirmed below 3 MPN/g using the method of FDA BAM Chapter 4. *Salmonella* was confirmed to be not detected per a 25 gram sample according to the method of FDA BAM Chapter 5. *Staphylococcus aureus* was confirmed to be below 10 cfu/g using the method of FDA BAM Chapter 12. Color was confirmed by visual inspection to be caramel.

The container was sealed, the remaining retention sample was frozen and stored for future reference, and a certificate of analysis was issued for the resulting lot.

Example 34: Preparation of Treated Drinking Water

Drinking water containing 250 ppm of the oligosaccharide preparation of Example 9.7 was prepared as follows. 37 mL of the oligosaccharide syrup of Example 33 and 40 grams of potassium sorbate were added gradually to 50 gallons of potable tap water in a 55 gallon blue-poly drum. The solution was mixed manually using a paddle for 10 minutes at room temperature.

The method was repeated without the incorporation of potassium sorbate.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein can be employed in practicing the invention. It is therefore contemplated that the invention shall also cover any such alternatives, modifications, variations or equivalents.

What is claimed is:

1. A method of manufacturing a synthetic oligosaccharide composition, the method comprising:
    (a) heating an aqueous composition that comprises at least one feed sugar and a catalyst to a pre-determined temperature for a period of time sufficient to induce polymerization of said at least one feed sugar; to thereby produce a batch of a synthetic oligosaccharide preparation;
    wherein said batch comprises at least 1 kg of said synthetic oligosaccharide preparation; and wherein said synthetic oligosaccharide preparation comprises at least n fractions of oligosaccharides each having a distinct degree of polymerization selected from 1 (DP1 fraction) to n (DPn fraction), wherein n is an integer greater than or equal to 3; and wherein each fraction of said synthetic oligosaccharide preparation comprises from about 0.5% to about 15% anhydro-subunit containing oligosaccharides by relative abundance as measured by mass spectrometry;
    (b) measuring a level of said catalyst in the produced batch of the synthetic oligosaccharide preparation;
    (c) determining whether the measured catalyst level in the produced batch is less than 1 wt. % corresponding to a pre-determined acceptance criterion; and
    (d) formulating at least a portion of said batch of said synthetic oligosaccharide preparation only if the measured catalyst level in the produced batch meets said pre-determined acceptance criterion.

2. The method of claim 1, wherein said formulating comprises adjusting the pH of said synthetic oligosaccharide preparation, producing a powder form of said synthetic oligosaccharide preparation, producing a solid form of said synthetic oligosaccharide preparation, packaging said synthetic oligosaccharide preparation, labeling said synthetic oligosaccharide preparation, releasing said synthetic oligosaccharide preparation into commerce, or offering for sale or selling said synthetic oligosaccharide preparation.

3. The method of claim 2, wherein said catalyst is selected from the group consisting of: (+)-camphor-10-sulfonic acid; 2-pyridinesulfonic acid; 3-pyridinesulfonic acid; 8-hydroxy-5-quinolinesulfonic acid hydrate; α-hydroxy-2-pyridinemethanesulfonic acid; (β)-camphor-10-sulfonic acid; butylphosphonic acid; diphenylphosphinic acid; hexylphosphonic acid; methylphosphonic acid; phenylphosphinic acid; phenylphosphonic acid; tert-butylphosphonic acid; SS)-VAPOL hydrogenphosphate; 6-quinolinesulfonic acid, 3-(1-pyridinio)-1-propanesulfonate; 2-(2-pyridinyl)ethanesulfonic acid; 3-(2-pyridyl)-5,6-diphenyl-1,2,4-triazine-p,p'-disulfonic acid monosodium salt hydrate; 1,1'-binaphthyl-2, 2'-diyl-hydrogenphosphate; bis(4-methoxyphenyl) phosphinic acid; phenyl(3,5-xylyl)phosphinic acid; L-cysteic acid monohydrate; poly(styrene sulfonic acid-co-divinylbenzene); lysine; Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; and Tryptophan.

4. The method of claim 3, wherein said catalyst is selected from the group consisting of: Ethanedisulfonic acid; Ethanesulfonic acid; Isethionic acid; Homocysteic acid; HEPBS (N-(2-Hydroxyethyl)piperazine-N'-(4-butanesulfonic acid)); HEPES (4-(2-hydroxyethyl)-1-piperazineethanesulfonic acid); 2-Hydroxy-3-morpholinopropanesulfonic acid; 2-(N-morpholino)ethanesulfonic acid; Methanesulfonic acid; Methaniazide; Naphthalene-1-sulfonic acid; Naphthalene-2-sulfonic acid; Perfluorobutanesulfonic acid; 6-sulfoquinovose; Triflic acid; 2-aminoethanesulfonic acid; Benzoic acid; Chloroacetic acid; Trifluoroacetic acid; Caproic acid; Enanthic acid; Caprylic acid; Pelargonic acid; Lauric acid; Pamitic acid; Stearic acid; Arachidic acid; Aspartic acid; Glutamic acid; Serine; Threonine; Glutamine; Cysteine; Glycine; Proline; Alanine; Valine; Isoleucine; Leucine; Methionine; Phenylalanine; Tyrosine; and Tryptophan.

5. The method of claim 4, wherein said heating comprises heating said aqueous composition for a time sufficient for said aqueous composition to reach equilibrium, wherein equilibrium is determined by a relative standard deviation of a series of Km of less than 15%, 10%, or 5%, and wherein $$Km = \frac{[DP_m][H_2O]}{[DP_{m-1}][DP1]},$$

m is an integer larger than 1 and less than or equal to n, a series of Km comprises at least 5 Km numbers, $[H_2O]$ represents the molar water concentration, and [DP1], $[DP_{m-i}]$, and [DPm] represent the molar concentrations of oligosaccharides in the DP1, $DPm_{-i}$, and DPm fractions respectively.

6. The method of claim 5, wherein said heating comprises heating said aqueous composition for at least 30 minutes, 1 hour, 2 hours, 3 hours, 4 hours, 5 hours, 6 hours, 7 hour, 8 hours, 9 hours, or 10 hours.

7. The method of claim 1, wherein said feed sugar comprises functionalized or modified sugars.

8. A method of manufacturing a synthetic oligosaccharide composition, the method comprising:
(a) heating an aqueous composition that comprises at least one feed sugar and a catalyst to a pre-determined temperature for a period of time sufficient to induce polymerization of said at least one feed sugar; to thereby produce a batch of a synthetic oligosaccharide preparation; wherein said batch comprises at least 1 kg of said synthetic oligosaccharide preparation; and wherein said synthetic oligosaccharide preparation comprises at least n fractions of oligosaccharides each having a distinct degree of polymerization selected from 1 (DP1 fraction) to n (DPn fraction), wherein n is an integer greater than or equal to 3; and wherein each fraction of said synthetic oligosaccharide preparation comprises from 0.5% to 15% anhydro-subunit containing oligosaccharides by relative abundance as measured by mass spectrometry;
(b) measuring a level of said catalyst in said produced batch of said synthetic oligosaccharide preparation; and
(c) formulating at least a portion of said batch of said synthetic oligosaccharide preparation only if the measured level of said catalyst in said produced batch of said synthetic oligosaccharide preparation is equal to or less than 0.1 wt. % of said batch;
to thereby produce a synthetic oligosaccharide composition.

9. The method of claim 8, wherein said formulating comprises adjusting the pH of said synthetic oligosaccharide preparation, producing a powder form of said synthetic oligosaccharide preparation, producing a solid form of said synthetic oligosaccharide preparation, packaging said synthetic oligosaccharide preparation, labeling said synthetic oligosaccharide preparation, releasing said synthetic oligosaccharide preparation into commerce, or offering for sale or selling said synthetic oligosaccharide preparation.

* * * * *